US008283127B2

(12) United States Patent
Pfleger et al.

(10) Patent No.: US 8,283,127 B2
(45) Date of Patent: Oct. 9, 2012

(54) DETECTION SYSTEM AND USES THEREFOR

(75) Inventors: Kevin D. Pfleger, Nedlands (AU); Ruth M. Seeber, Tuart Hill (AU); Heng Boon See, Yokine (AU); Karin A. Eidne, Cottesloe (AU)

(73) Assignee: Dimerix Bioscience Pty Ltd., Nedlands (AU)

( * ) Notice: Subject to any disclaimer, the term of this patent is extended or adjusted under 35 U.S.C. 154(b) by 617 days.

(21) Appl. No.: 12/442,899

(22) PCT Filed: Nov. 9, 2007

(86) PCT No.: PCT/AU2007/001722
§ 371 (c)(1),
(2), (4) Date: Jul. 29, 2009

(87) PCT Pub. No.: WO2008/055313
PCT Pub. Date: May 15, 2008

(65) Prior Publication Data
US 2010/0021457 A1     Jan. 28, 2010

(30) Foreign Application Priority Data

Nov. 10, 2006 (AU) ............................ 2006906292

(51) Int. Cl.
*G01N 33/53* (2006.01)
*G01N 31/00* (2006.01)
(52) U.S. Cl. ......... 435/7.21; 435/4; 435/7.1; 435/287.9; 436/501; 436/518; 530/300; 530/350
(58) Field of Classification Search .................. None
See application file for complete search history.

(56) References Cited

U.S. PATENT DOCUMENTS

| | | |
|---|---|---|
| 4,391,904 A | 7/1983 | Litman et al. |
| 4,671,958 A | 6/1987 | Rodwell et al. |
| 4,751,180 A | 6/1988 | Cousens et al. |
| 4,925,673 A | 5/1990 | Steiner et al. |
| 4,935,233 A | 6/1990 | Bell et al. |
| 5,013,556 A | 5/1991 | Woodle et al. |
| 5,891,646 A | 4/1999 | Barak et al. |
| 6,110,693 A | 8/2000 | Barak et al. |
| 6,800,445 B2 | 10/2004 | Palmer et al. |
| 6,893,827 B1 | 5/2005 | Palmer et al. |
| 7,049,076 B2 | 5/2006 | Lee et al. |

FOREIGN PATENT DOCUMENTS

| | | |
|---|---|---|
| WO | WO-2005/031309 A2 | 4/2005 |
| WO | WO-2005/050182 A1 | 6/2005 |

OTHER PUBLICATIONS

Abdalla et al., AT1-receptor heterodimers show enhanced G-protein activation and altered receptor sequestration, Nature 407:94-8 (2000).
Abdalla et al., Increased AT(1) receptor heterodimers in preeclampsia mediate enhanced angiotensin II responsiveness, Nat. Med. 7:1003-9 (2001).
Adams et al., New biarsenical ligands and tetracysteine motifs for protein labeling in vitro and in vivo: synthesis and biological applications, J. Am. Chem. Soc. 124:6063-76 (2002).
Agnati et al., Existence and theoretical aspects of homomeric and heteromeric dopamine receptor complexes and their relevance for neurological disease, Neuromolecular Med. 7(1-2):61-78 (2005). [Abstract only provided.].
Angers et al. Detection of beta 2-adrenergic receptor dimerization in living cells using bioluminescence resonance energy transfer (BRET), Proc. Natl. Acad. Sci. USA 97:3684-9 (2000).
Angers et al., Biochemical and biophysical demonstration of GPCR oligomerization in mammalian cells, Life Sci. 68:2243-50 (2001).
Auerbach et al., The post-genomic era of interactive proteomics: facts and perspectives. Proteomics 2:611-23 (2002).
Ayoub et al., Monitoring of ligand-independent dimerization and ligand-induced conformational changes of melatonin receptors in living cells by bioluminescence resonance energy transfer, J. Biol. Chem. 277:21522-8 (2002).
Ayoub et al., Preferential formation of MT1/MT2 melatonin receptor heterodimers with distinct ligand interaction properties compared with MT2 homodimers, Mol. Pharmacol. 66:312-21 (2004).
Babcock et al., Ligand-independent dimerization of CXCR4, a principal HIV-1 coreceptor, J. Biol. Chem. 278:3378-85 (2003).
Bai, Dimerization of G-protein-coupled receptors: roles in signal transduction, Cell Signal 16:175-86 (2004).
Baumann et al., Hypocretins (orexins): clinical impact of the discovery of a neurotransmitter, Sleep Med. Rev. 9:253-68 (2005).
Berglund et al., Neuropeptide Y Y4 receptor homodimers dissociate upon agonist stimulation, J. Pharmacol. Exp. Ther. 307:1120-6 (2003).
Berthouze et al., Constitutive dimerization of human serotonin 5-HT4 receptors in living cells, FEBS Lett. 579:2973-80 (2005).
Bouvier, Oligomerization of G-protein-coupled transmitter receptors, Nat. Rev. Neurosci. 2:274-86 (2001).
Breit et al., Hetero-oligomerization between beta2- and beta3-adrenergic receptors generates a beta-adrenergic signaling unit with distinct functional properties, J. Biol. Chem. 279:28756-65 (2004).
Breit et al., Simultaneous activation of the delta opioid receptor (deltaOR)/sensory neuron-specific receptor-4 (SNSR-4) hetero-oligomer by the mixed bivalent agonist bovine adrenal medulla peptide 22 activates SNSR-4 but inhibits deltaOR signaling, Mol. Pharmacol. 70:686-96 (2006).
Breitweiser, G protein-coupled receptor oligomerization: implications for G protein activation and cell signaling, Circ. Res. 94:17-27 (2004).

(Continued)

*Primary Examiner* — Lisa Cook
(74) *Attorney, Agent, or Firm* — Marshall, Gerstein & Borun LLP

(57) ABSTRACT

A system for the detection of molecular associations, the system comprising: i) a first agent, comprising a first interacting group coupled to a first reporter component; ii) a second agent, comprising a second interacting group coupled to a second reporter component; iii) a third agent, comprising a third interacting group; iv) a modulator; and v) a detector; wherein proximity of the first and second reporter components generates a signal capable of detection by the detector; and wherein the modulator modulates the association of the second interacting group with the third interacting group; such that monitoring the signal generated by proximity of the first and second reporter components by the detector constitutes monitoring the association of the first and third agents.

12 Claims, 25 Drawing Sheets

OTHER PUBLICATIONS

Brisbare-Roch et al., Promotion of sleep by targeting the orexin system in rats, dogs and humans, Nat. Med. 13:150-5 (2007).
Bruchez et al., Semiconductor nanocrystals as fluorescent biological labels, Science 281:2013-6 (1998).
Bulenger et al., Emerging role of homo- and heterodimerization in G-protein-coupled receptor biosynthesis and maturation, Trends Pharmacol. Sci., 26:131-7 (2005).
Campbell et al., A monomeric red fluorescent protein, Proc. Natl. Acad. Sci. USA 99:7877-82 (2002).
Canals et al., Adenosine A2A-dopamine D2 receptor-receptor heteromerization: qualitative and quantitative assessment by fluorescence and bioluminescence energy transfer, J. Biol. Chem. 278:46741-9 (2003).
Carrillo et al., Dimers of class A G protein-coupled receptors function via agonist-mediated trans-activation of associated G proteins, J. Biol. Chem. 278:42578-87 (2003).
Chen et al., Heterodimerization and cross-desensitization between the mu-opioid receptor and the chemokine CCR5 receptor, Eur. J. Pharmacol. 483:175-86 (2004).
Cheng et al., Agonist-dependent dissociation of oligomeric complexes of G protein-coupled cholecystokinin receptors demonstrated in living cells using bioluminescence resonance energy transfer, J. Biol. Chem. 276:48040-7 (2001).
Chinenov et al., Close encounters of many kinds: Fos-Jun interactions that mediate transcription regulatory specificity, Oncogene 20:2438-2452 (2001).
Ciruela et al., Presynaptic control of striatal glutamatergic neurotransmission by adenosine $A_1$-$A_{2A}$ receptor heteromers, J. Neurosci. 26:2080-7 (2006).
De et al., An improved bioluminescence resonance energy transfer strategy for imaging intracellular events in single cells and living subjects, Cancer Res. 67:7175-83 (2007).
De Wet et al., Firefly luciferase gene: structure and expression in mammalian cells, Mol. Cell Biol. 7:725-37 (1987).
Devost, Homo- and hetero-dimeric complex formations of the human oxytocin receptor, J. Neuroendocrinol. 16:372-7 (2004).
Eidne et al., Applications of novel resonance energy transfer techniques to study dynamic hormone receptor interactions in living cells, Trends Endocrinol. Metab. 13:415-21 (2002).
El-Asmar et al., Evidence for negative binding cooperativity within CCR5-CCR2b heterodimers, Mol. Pharmacol. 67:460-9 (2005).
Ellis et al., Orexin-1 receptor-cannabinoid CB1 receptor heterodimerization results in both ligand-dependent and -independent coordinated alterations of receptor localization and function, J. Biol. Chem. 281:38812-24 (2006).
Fradkov et al., Far-red fluorescent tag for protein labelling, Biochem. J. 368:17-21 (2002).
Fuxe et al., Adenosine A2A and dopamine D2 heteromeric receptor complexes and their function, J. Mol. Neurosci. 26:209-20 (2005). [Abstract only provided.]
Gary et al, The thyrotropin-releasing hormone (TRH) hypothesis of homeostatic regulation: implications for TRH-based therapeutics, J. Pharmacol. Exp. Ther. 305:410-16 (2003).
George et al., G-protein-coupled receptor oligomerization and its potential for drug discovery, Nat. Rev. Drug Discov. 1:808-20 (2002).
Gomes et al., A role for heterodimerization of mu and delta opiate receptors in enhancing morphine analgesia, Proc. Natl. Acad. Sci. USA 101:5135-9 (2004).
Gomes et al., Oligomerization of opioid receptors. Methods 27:358-65 (2002).
Grant et al., Agonist-dependent dissociation of human somatostatin receptor 2 dimers: a role in receptor trafficking. J. Biol. Chem. 279:36179-83 (2004).
Greer et al., Imaging of light emission from the expression of luciferases in living cells and organisms: a review. Luminescence 17:43-74 (2002).
Gregan et al., Ligand-dependent differences in the internalization of endothelin A and endothelin B receptor heterodimers. J..Biol. Chem. 279:27679-87 (2004).
Griffin et al., Specific covalent labeling of recombinant protein molecules inside live cells, Science 281:269-272 (1998).
Gupta et al., Targeting opioid receptor heterodimers: strategies for screening and drug development. AAPS J. 8:E153-9 (2006).
Gurskaya et al., GFP-like chromoproteins as a source of far-red fluorescent proteins, FEBS Lett. 407:16-20 (2001).
Hamdan et al., High-throughput screening of G protein-coupled receptor antagonists using a bioluminescence resonance energy transfer 1-based beta-arrestin2 recruitment assay, J. Biomol. Screen. 10:463-75 (2005).
Hansen et al., Functional consequences of 7TM receptor dimerization, Eur. J. Pharm. Sci. 23:301-17 (2004).
Hansen et al., Oligomerization of wild type and nonfunctional mutant angiotensin II type I receptors inhibits galphaq protein signaling but not ERK activation, J. Biol. Chem. 279:24108-15 (2004).
Hanyaloglu et al., Homo- and hetero-oligomerization of thyrotropin-releasing hormone (TRH) receptor subtypes. Differential regulation of beta-arrestins 1 and 2, J. Biol. Chem. 277:50422-30 (2002).
Harikumar et al., Constitutive formation of oligomeric complexes between family B G protein-coupled vasoactive intestinal polypeptide and secretin receptors, Mol. Pharmacol. 69:363-73 (2006).
Harrison et al., Current methods used to investigate G protein coupled receptor oligomerisation. J. Pharmacol. Toxicol. Methods 54:26-35 (2006).
Hastings, Chemistries and colors of bioluminescent reactions: a review, Gene 173:5-11 (1996).
Haynes et al., A selective orexin-1 receptor antagonist reduces food consumption in male and female rats, Regul. Pept. 96:45-51 (2000).
Hebert et al., Detecting and imaging protein-protein interactions during G protein-mediated signal transduction in vivo and in situ by using fluorescence-based techniques. Cell Biochem. Biophys. 45(1):85-109 (2006).
Heding et al., The rat gonadotropin-releasing hormone receptor internalizes via a beta-arrestin-independent, but dynamin-dependent, pathway: addition of a carboxyl-terminal tail confers beta-arrestin dependency, Endocrinology 141:299-306 (2000).
Heim et al., Wavelength mutations and posttranslational autoxidation of green fluorescent protein, Proc. Natl. Acad. Sci. USA 91:12501-4 (1994).
Hernanz-Falcon et al., Identification of amino acid residues crucial for chemokine receptor dimerization, Nat. Immunol. 5:216-23 (2004).
Herrick-Davis et al., Biochemical and biophysical characterization of serotonin 5-HT2C receptor homodimers on the plasma membrane of living cells, Biochem. 43:13963-71 (2004).
Herrick-Davis et al., Inhibition of serotonin 5-hydroxytryptamine2c receptor function through heterodimerization: receptor dimers bind two molecules of ligand and one G-protein, J. Biol. Chem. 280:40144-51 (2005).
Herrick-Davis et al., Serotonin 5-HT2C receptor homodimer biogenesis in the endoplasmic reticulum: real-time visualization with confocal fluorescence resonance energy transfer, J. Biol. Chem. 281:27109-16 (2006).
Hilairet et al., Hypersensitization of the Orexin 1 receptor by the CB1 receptor: evidence for cross-talk blocked by the specific CB1 antagonist, SR141716, J. Biol. Chem. 278:23731-23737 (2003).
Hirose et al., N-acyl 6,7-dimethoxy-1,2,3,4-tetrahydroisoquinoline: the first orexin-2 receptor selective non-peptidic antagonist, Bioorg. Med. Chem. Lett. 13:4497-9 (2003).
Houghton et al., Mouse monoclonal IgG3 antibody detecting GD3 ganglioside: a phase I trial in patients with malignant melanoma, Proc. Natl. Acad. Sci. USA 82:1242-6 (1985).
Hu et al., Simultaneous visualization of multiple protein interactions in living cells using multicolor fluorescence complementation analysis, Nat. Biotechnol. 21:539-45 (2003).
Huang et al., Angiotensin II type 1 and bradykinin B2 receptors expressed in early stage epithelial cells derived from human embryonic stem cells, J. Cell Physiol. 211:816-25 (2007).
Huttenrauch et al., G protein-coupled receptor kinases promote phosphorylation and beta-arrestin-mediated internalization of CCR5 homo- and hetero-oligomers, J. Biol. Chem. 280:37503-15 (2005).

Inouye et al., The use of Renilla luciferase, Oplophorus luciferase, and apoaequorin as bioluminescent reporter protein in the presence of coelenterazine analogues as substrate, Biochem. Biophys. Res. Commun. 233:349-53 (1997).

International Preliminary Report on Patentability for corresponding International Application No. PCT/AU2007/001722, dated May 12, 2009.

International Search Report and Written Opinion for corresponding International Application No. PCT/AU2007/001722, dated Jan. 15, 2008.

Ishihara et al., Molecular basis of the cell specificity of cytokine action, Biochim. Biophys. Acta. 1592:281-96 (2002).

Ishii et al., Effects of the state of the succinimido-ring on the fluorescence and structural properties of pyrene maleimide-labeled alpha alpha-tropomyosin, Biophys. J. 50:75-89 (1986).

James et al., A rigorous experimental framework for detecting protein oligomerization using bioluminescence resonance energy transfer, Nat. Methods 3:1001-6 (2006).

Jensen et al., Probing intermolecular protein-protein interactions in the calcium-sensing receptor homodimer using bioluminescence resonance energy transfer (BRET), Eur. J. Biochem. 269:5076-87 (2002).

Jordan et al., G-protein-coupled receptor heterodimerization modulates receptor function, Nature 399:697-700 (1999).

Kamiya et al., Oligomerization of adenosine A2A and dopamine D2 receptors in living cells, Biochem. Biophys. Res. Commun. 306:544-9 (2003).

Kok et al., Altered setting of the pituitary-thyroid ensemble in hypocretin-deficient narcoleptic men, Am. J. Physiol. Endocrinol. Metabol. 288:892-9 (2005).

Kreider et al., Immunohistochemical localization of TRH in rat CNS: comparison with RIA studies, Peptides 6:997-1000 (1985).

Kroeger et al., Constitutive and agonist-dependent homo-oligomerization of the thyrotropin-releasing hormone receptor. Detection in living cells using bioluminescence resonance energy transfer, J. Biol. Chem. 276:12736-43 (2001).

Kroeger et al., G-protein coupled receptor oligomerization in neuroendocrine pathways, Front Neuroendocrinol. 24:254-78 (2003).

Lang et al., Structure-activity studies of orexin a and orexin B at the human orexin 1 and orexin 2 receptors led to orexin 2 receptor selective and orexin 1 receptor preferring ligands, J. Med. Chem. 47:1153-1160 (2004).

Langmead et al., Characterisation of the binding of [3H]-SB-674042, a novel nonpeptide antagonist, to the human orexin-1 receptor, Br. J. Pharmacol. 141:340-6 (2004).

Lefevre et al., Texas Res-X and rhodamine Red-X, new derivatives of sulforhodamine 101 and lissamine rhodamine B with improved labeling and fluorescence properties, Bioconjug. Chem. 7:482-9 (1996).

Levi et al., Bisdeoxycoelenterazine derivatives for improvement of bioluminescence resonance energy transfer assays, J. Am. Chem. Soc. 129:11900-1 (2007).

Levoye et al., Do orphan G-protein-coupled receptors have ligand-independent functions? New insights from receptor heterodimers. EMBO J. 7:1094-8 (2006).

Levoye et al., The orphan GPR50 receptor specifically inhibits MT1 melatonin receptor function through heterodimerization. EMBO J. 25:3012-23 (2006).

Loening et al., Consensus guided mutagenesis of Renilla luciferase yields enhanced stability and light output, Protein Eng. Des. Sel. 19:391-400 (2006).

Loening et al., Red-shifted Renilla reniformis luciferase variants for imaging in living subjects, Nat. Methods 4:641-3 (2007).

Lorenz et al., Isolation and expression of a cDNA encoding Renilla reniformis luciferase. Proc. Natl. Acad Sci. USA 88:4438-42 (1991).

Masse et al., A prospective longitudinal study of platelet angiotensin II receptors for the prediction of preeclampsia, Clin. Biochem. 31:251-255 (1998).

Matz et al., Fluorescent proteins from nonbioluminescent Anthozoa species, Nat. Biotechnol. 17:969-73 (1999).

McAtee et al., Novel substituted 4-phenyl-[1,3]dioxanes: potent and selective orexin receptor 2 (OX(2)R) antagonists, Bioorg. Med. Chem. Lett. 14:4225-9 (2004).

Mellado et al., Chemokine receptor homo- or heterodimerization activates distinct signaling pathways, EMBO J. 20:2497-507 (2001).

Mercier et al., Quantitative assessment of beta 1- and beta 2-adrenergic receptor homo- and heterodimerization by bioluminescence resonance energy transfer, J. Biol. Chem. 277:44925-31 (2002).

Merrifield, Solid-phase peptide synthesis. I. The synthesis of a tetrapeptide, J. Am. Chem. Soc. 85:2149-54 (1964).

Milligan et al., GPCR dimerisation, Life Sci., 74:181-8 (2003).

Milligan et al., G protein-coupled receptor fusion proteins in drug discovery, Curr. Pharm. Des. 10:1989-2001 (2004).

Milligan et al., Methods to monitor the quaternary structure of G protein-coupled receptors, FEBS J. 272:2914-25 (2005).

Milligan et al., Oligomeric structure of the alpha1b-adrenoceptor: comparisons with rhodopsin, Vision Res. 46:4434-41 (2006).

Milligan et al., Selectivity in the oligomerisation of G protein-coupled receptors, Semin. Cell Dev. Biol. 15:263-8 (2004).

Milligan et al., The role of GPCR dimerisation/oligomerisation in receptor signalling, Ernst Schering Found. Symp. Proc., pp. 145-61 (2006). [Abstract only provided.]

Milligan et al., The specificity and molecular basis of alpha1-adrenoceptor and CXCR chemokine receptor dimerization. J. Mol. Neurosci. 26(2-3):161-8 (2005). [Abstract only provided.]

Milligan, Applications of bioluminescence- and fluorescence resonance energy transfer to drug discovery at G protein-coupled receptors, Eur. J. Pharm. Sci. 21:397-405 (2004).

Milligan, G protein-coupled receptor dimerization: function and ligand pharmacology, Mol. Pharmacol. 66:1-7 (2004).

Milligan, G-protein-coupled receptor heterodimers: pharmacology, function and relevance to drug discovery, Drug Discov. Today 11:541-9 (2006).

Milligan, Oligomerisation of G-protein-coupled receptors, J. Cell Sci. 114:1265-71 (2001).

Murphy et al., Genetic construction, expression, and melanoma-selective cytotoxicity of a diphtheria toxin-related alpha-melanocyte-stimulating hormone fusion protein, Proc. Natl. Acad. Sci. USA 83:8258-62 (1986).

Nagai et al., A variant of yellow fluorescent protein with fast and efficient maturation for cell-biological applications, Nat. Biotechnol. 20:87-90 (2002).

Nishino et al., Effects of thyrotropin-releasing hormone and its analogs on daytime sleepiness and cataplexy in canine narcolepsy, J. Neurosci. 17:6401-8 (1997).

Okabe et al., 'Green mice' as a source of ubiquitous green cells, FEBS Lett. 407:313-9 (1997).

Overton et al., Use of fluorescence resonance energy transfer to analyze oligomerization of G-protein-coupled receptors expressed in yeast, Methods 27:324-32 (2002).

Paulmurugan et al., Monitoring protein-protein interactions using split synthetic renilla luciferase protein-fragment-assisted complementation, Anal. Chem. 75:1584-9 (2003).

Percherancier et al., Bioluminescence resonance energy transfer reveals ligand-induced conformational changes in CXCR4 homo- and heterodimers, J. Biol. Chem. 280:9895-903 (2005).

Pfleger et al., Bioluminescence resonance energy transfer (BRET) for the real-time detection of protein-protein interactions, Nat. Protoc. 1:337-45 (2006).

Pfleger et al., Extended bioluminescence resonance energy transfer (eBRET) for monitoring prolonged protein-protein interactions in live cells, Cell Signal. 18:1664-70 (2006).

Pfleger et al., Illuminating insights into protein-protein interactions using bioluminescence resonance energy transfer (BRET), Nat. Methods 3:165-74 (2006).

Pfleger et al., Monitoring the formation of dynamic G-protein-coupled receptor-protein complexes in living cells, Biochem. J. 385:625-37 (2005).

Pfleger et al., New technologies: bioluminescence resonance energy transfer (BRET) for the detection of real time interactions involving G-protein coupled receptors, Pituitary 6:141-51 (2003).

Pouliot et al., Platelet angiotensin II binding sites and early detection of preeclampsia, Obstet. Gynecol. 91:591-95 (1998).

Prinster et al., Heterodimerization of g protein-coupled receptors: specificity and functional significance. Pharmacol. Rev. 57(3):289-98 (2005).

Quitterer et al., AT1 receptor heterodimers and angiotensin II responsiveness in preeclampsia, Semin. Nephrol. 24:115-9 (2004).

Ramsay et al., Homo- and hetero-oligomeric interactions between G-protein-coupled receptors in living cells monitored by two variants of bioluminescence resonance energy transfer (BRET): hetero-oligomers between receptor subtypes form more efficiently than between less closely related sequences, Biochem. J. 365:429-40 (2002).

Renming et al., Antiepileptic effects of CNK-602A, a novel thyrotropin-releasing hormone analog, on absence-like and tonic seizures of spontaneously epileptic rats, Eur. J. Pharmacol. 223:185-92 (1992).

Riehl et al., Chronic oral administration of CG-3703, a thyrotropin releasing hormone analog, increases wake and decreases cataplexy in canine narcolepsy, Neuropsychopharmacol. 23:34-45 (2000).

Rios et al., G-protein-coupled receptor dimerization: modulation of receptor function, Pharmacol. Ther. 92:71-87 (2001).

Rios et al., Interactions between delta opioid receptors and alpha-adrenoceptors, Clin. Exp. Pharmacol. Physiol. 31:833-6 (2004).

Rios et al., mu opioid and CB1 cannabinoid receptor interactions: reciprocal inhibition of receptor signaling and neuritogenesis, Br. J. Pharmacol. 148:387-95 (2006).

Robert et al., Mechanisms of cell-surface rerouting of an endoplasmic reticulum-retained mutant of the vasopressin V1b/V3 receptor by a pharmacological chaperone, J. Biol. Chem. 280:42198-206 (2005).

Rocheville et al., Receptors for dopamine and somatostatin: formation of hetero-oligomers with enhanced functional activity, Science 288:154-7 (2000).

Roda et al., Bioluminescence and chemiluminescence in drug screening, Anal. Bioanal. Chem. 377:826-33 (2003).

Rodgers et al., SB-334867, a selective orexin-1 receptor antagonist, enhances behavioural satiety and blocks the hyperphagic effect of orexin-A in rats, Eur. J. Neurosci. 13:1444-52 (2001).

Rodriguez-Frade et al., Blocking HIV-1 infection via CCR5 and CXCR4 receptors by acting in trans on the CCR2 chemokine receptor, EMBO J. 23:66-76 (2004).

Sakurai et al., Orexins and orexin receptors: a family of hypothalamic neuropeptides and G protein-coupled receptors that regulate feeding behavior, Cell 92:573-85 (1998).

Sakurai, Roles of orexin/hypocretin in regulation of sleep/wakefulness and energy homeostasis, Sleep Med. Rev. 9:231-41 (2005).

Salahpour et al., Homodimerization of the beta2-adrenergic receptor as a prerequisite for cell surface targeting, J. Biol. Chem. 279:33390-7 (2004).

Shah, Role of the renin-angiotensin system in the pathogenesis of preeclampsia, Am. J. Physiol. Renal Physiol. 288:F614-625 (2005).

Shaner et al., A guide to choosing fluorescent proteins, Nat. Methods 2:905-9 (2005).

Shimomura, Membrane permeability of coelenterazine analogues measured with fish eggs, Biochem. J. 326:297-8 (1997).

Small et al., Alpha(2A)- and alpha(2C)-adrenergic receptors form homo- and heterodimers: the heterodimeric state impairs agonist-promoted GRK phosphorylation and beta-arrestin recruitment, Biochemistry 45:4760-7 (2006).

Song et al., Regulated dimerization of the thyrotropin-releasing hormone receptor affects receptor trafficking but not signaling, Mol. Endocrinol.19:2859-70 (2005).

Springael et al., Allosteric modulation of binding properties between units of chemokine receptor homo- and hetero-oligomers, Mol. Pharmacol. 69:1652-61 (2006).

Springael et al., Dimerization of chemokine receptors and its functional consequences, Cytokine Growth Factor Rev. 16:611-23 (2005).

Starr-Spires et al., HIV-1 entry and entry inhibitors as therapeutic agents, Clin. Lab. Med. 22:681-701 (2002).

Storez et al., Homo- and hetero-oligomerization of beta-arrestins in living cells, J. Biol. Chem. 280:40210-5 (2005).

Stranick et al., Identification of transcription factor binding sites important in the regulation of the human interleukin-5 gene, J. Biol. Chem. 272:16453-65 (1997).

Tateyama et al., Ligand-induced rearrangement of the dimeric metabotropic glutamate receptor 1 alpha, Nat. Struct. Mol. Biol. 11:637-42 (2004).

Terrillon et al., Heterodimerization of V1a and V2 vasopressin receptors determines the interaction with beta-arrestin and their trafficking patterns, Proc. Natl. Acad. Sci. USA 101:1548-53 (2004).

Terrillon et al., Oxytocin and vasopressin V1a and V2 receptors form constitutive homo- and heterodimers during biosynthesis, Mol. Endocrinol. 17:677-91 (2003).

Terrillon et al., Receptor activity-independent recruitment of betaarrestin2 reveals specific signalling modes, EMBO J. 23:3950-61 (2004).

Terrillon et al., Roles of G-protein-coupled receptor dimerization, EMBO Rep. 5:30-4 (2004).

Thevenin et al., Oligomerization of the fifth transmembrane domain from the adenosine A2A receptor, Protein Sci. 14:2177-86 (2005).

Torvinen et al., Adenosine A2A receptor and dopamine D3 receptor interactions: evidence of functional A2A/D3 heteromeric complexes, Mol. Pharmacol. 67:400-7 (2005).

Toth et al., Regulation of CXCR4 receptor dimerization by the chemokine SDF-1 alpha and the HIV-1 coat protein gp120: a fluorescence resonance energy transfer (FRET) study, J. Pharmacol. Exp. Ther. 310:8-17 (2004).

Tsien, The green fluorescent protein. Annu. Rev. Biochem. 67:509-44 (1998).

Verhaegent et al., Recombinant Gaussia luciferase. Overexpression, purification, and analytical application of a bioluminescent reporter for DNA hybridization, Anal. Chem. 74:4378-85 (2002).

Waldhoer et al., A heterodimer-selective agonist shows in vivo relevance of G protein-coupled receptor dimers, Proc. Natl. Acad. Sci. USA 102:9050-5 (2005).

Wang et al., Constitutive association of cell surface CCR5 and CXCR4 in the presence of CD4, J. Cell Biochem. 93:753-60 (2004).

Wang et al., Activation of the granulocyte-macrophage colony-stimulating factor promoter in T cells requires cooperative binding of Elf-1 and AP-1 transcription factors, Mol. Cell Biol. 14:1153-9 (1994).

Wang et al., Dimerization of CXCR4 in living malignant cells: control of cell migration by a synthetic peptide that reduces homologous CXCR4 interactions, Mol. Cancer Ther. 5:2474-83 (2006).

Wang et al., Opioid receptor homo- and heterodimerization in living cells by quantitative bioluminescence resonance energy transfer, Mol. Pharmacol. 67:2173-84 (2005).

Wang et al., The orexinergic synaptic innervation of serotonin- and orexin 1-receptor-containing neurons in the dorsal raphe nucleus, Regul. Pept. 126:35-42 (2005).

Wilson et al., The CXCR1 and CXCR2 receptors form constitutive homo- and heterodimers selectively and with equal apparent affinities, J. Biol. Chem. 280:28663-74 (2005).

Wolberger, Multiprotein-DNA complexes in transcriptional regulation, Annu. Rev. Biophys. Biomol. Struct. 28:29-56 (1999).

Wu et al., Resonance energy transfer: methods and applications, Anal Biochem. 218:1-13 (1994). [Abstract only provided.].

Xu et al., A bioluminescence resonance energy transfer (BRET) system: application to interacting circadian clock proteins, Proc. Natl. Acad. Sci. USA 96:151-6 (1999).

Yayama et al., Angiotensin-converting enzyme inhibitor enhances liver regeneration following partial hepatectomy: involvement of bradykinin B2 and angiotensin AT1 receptors, Biol. Pharm. Bull. 30:591-4 (2007).

Zacharias et al., Partitioning of lipid-modified monomeric GFPs into membrane microdomains of live cells, Science 296:913-6 (2002).

Zernicka-Goetz et al., Following cell fate in the living mouse embryo, Development 124:1133-7 (1997).

Zhang et al., Creating new fluorescent probes for cell biology, Nat. Rev. Mol. Cell. Biol. 3:906-18 (2002).

DETECTION SYSTEM AND USES THEREFOR

The application is a 371 of PCT/AU07/01722 filed Nov. 9, 2007 and Australian application number 2006906292 filed Nov. 10, 2006.

FIELD OF THE INVENTION

The present invention relates to a system for detecting molecular associations. The present invention has particular application to detecting the association of different molecules, and thus detecting the formation of hetero-dimers and/or -oligomers.

BACKGROUND ART

The background to the invention will be discussed in the context of the association of proteins. However, the scope of the invention should not be understood to be limited thereto.

Proteins do not act in isolation in a cell, but in stable or transitory complexes, with protein-protein interactions being key determinants of protein function (Auerbach et al., (2002), *Proteomics,* 2, 611-623). Furthermore, proteins and protein complexes interact with other cellular components like DNA, RNA and small molecules. Understanding both the individual proteins involved in these interactions and their interactions are important for a better understanding of biological processes.

Several tools exist for demonstrating protein-protein interactions either in vitro, coimmunoprecipitation with the potential for cross-linking at the cell surface, or in vivo, including for example the resonance energy transfer (RET) technologies of fluorescence RET (FRET) and bioluminescence RET (BRET).

The interaction of G-protein coupled receptors (GPCRs) represents an excellent example of the physiological and potential pharmacological relevance of the association of proteins, and in particular the relevance of hetero-dimers and/or -oligomers. As Milligan (Milligan, (2006), *Drug Discovery Today,* 11, 541-549) observes, homo-dimerisation and -oligomerisation have limited implications for the drug discovery industry, while "differential pharmacology, function and regulation of GCPR hetero-dimers and -oligomers suggest means to selectively target GPCRs in different tissues and hint that the mechanism of function of several pharmacological agents might be different in vivo than anticipated from simple ligand screening programmes that rely on heterologous expression of a single GPCR".

Coimmunoprecipitation has been used to identify GPCR heterodimers (Jordan B A & Devi L A (1999) G-protein-coupled receptor heterodimerization modulates receptor function *Nature* 399, 697-700). However, coimmunoprecipitation does not enable the distinction between constitutive and random associations. In particular, there is concern that artefactual aggregation occurs following cell lysis and solubilization (Kroeger K M et al. (2003) G-protein coupled receptor oligomerization in neuroendocrine pathways. *Front. Neuroendocrinol.* 24, 254-278). Further, coimmunoprecipitation is not amenable to automation or high throughput screening.

Fluorescence resonance energy transfer (FRET) is capable of detecting in vivo protein-protein interactions (Forster, (1948), *Ann. Phys.* 2, 57-75). This technique became particularly attractive and applicable to assays in living cells when the green fluorescent protein (GFP) and its mutant variants with different spectral characteristics were cloned. This allowed the genetic attachment of GFP and its variants to any target protein by fusing the encoding DNA sequences (Heim et al., (1994), *PNAS. USA.* 91, 12501-12504). FRET is able to monitor interactions that occur anywhere inside the cell. FRET can be determined in any cell type (mammalian, yeast, bacterial etc.) or cell-free system. It can be detected by fluorescence spectroscopy, fluorescence microscopy and fluorescence activated cell sorting (FACS).

Bioluminescence resonance energy transfer (BRET) is another technique that has been developed to study in vivo protein-protein interactions (Xu et al., (1999), *PNAS. USA,* 96, 151-156; Eidne et al., (2002), *Trends Endocrin. Metabol.* 13, 415-421). Like FRET, BRET allows detection within living cells or cell-free systems and is not restricted to a particular cellular compartment.

It is difficult to differentiate background signal from signals resulting from constitutive interactions using FRET or BRET to assess direct interactions between labelled proteins. Furthermore, interaction affinity does not relate directly to signal intensity as RET is dependent upon the relative orientation of and distance between the energy donor and acceptor.

'Saturation' BRET [Mercier J F, Salahpour A, Angers S, Breit A & Bouvier M (2002) Quantitative assessment of beta 1- and beta 2-adrenergic receptor homo- and heterodimerization by bioluminescence resonance energy transfer. J Biol Chem 277, 44925-44931.] has been suggested as a method to differentiate background and constitutive signals, however, this requires expression of increasing concentrations of acceptor-labelled protein relative to donor-labelled protein in order to generate saturation curves and is by no means high throughput.

The preceding discussion is intended only to facilitate an understanding of the invention. It should not be construed as in any way limiting the scope or application of the following description of the invention, nor should it be construed as an admission that any of the information discussed was within the common general knowledge of the person skilled in the appropriate art at the priority date.

DISCLOSURE OF THE INVENTION

The inventors have developed a detection system capable of overcoming or at least alleviating some of the problems identified in analysis of protein associations.

Most importantly, the system of the invention is capable of identifying potentially constitutive associations arising between different molecules (i.e., heterodimers) as well as those arising from multiple copies of the same molecule (i.e., oligomers), utilising a signal that is dependent upon external modulation, thereby enabling the ability to distinguish between constitutive associations and random associations.

In a first aspect of the invention, there is provided a system for the detection of the molecular associations, the system comprising:
   i). a first agent, comprising a first interacting group coupled to a first reporter component;
   ii). a second agent, comprising a second interacting group coupled to a second reporter component;
   iii). a third agent, comprising a third interacting group;
   iv). a modulator; and
   v). a detector;
wherein proximity of the first and second reporter components generates a signal capable of detection by the detector; and wherein the modulator modulates the association of the second interacting group with the third interacting group; such that monitoring the signal generated by proximity of the first and second reporter components by the detector constitutes monitoring the association of the first and third agents.

The system may further comprise a reporter component initiator, wherein proximity of the first and second reporter components generates a signal capable of detection by the detector only in the presence of the reporter component initiator.

In a second aspect of the invention, there is provided a method for the detection of the molecular associations, the method comprising the steps of:
i). Providing a first agent, comprising a first interacting group coupled to a first reporter component;
ii). Providing a second agent, comprising a second interacting group coupled to a second reporter component;
iii). Providing a third agent, comprising a third interacting group;
iv). Providing a modulator;
wherein; proximity of the first and second reporter components generates a signal; and wherein the modulator modulates the association of the second interacting group with the third interacting group; then
v). Detecting and/or monitoring any signal generated by proximity of the first and second reporter components.
such that monitoring the signal generated by proximity of the first and second reporter components by the detector constitutes monitoring the association of the first and third agents.

Before the step of detecting and/or monitoring any signal generated by proximity of the first and second reporter components, the method may further comprise the step of providing a reporter component initiator, wherein proximity of the first and second reporter components generates a signal capable of detection by the detector only in the presence of the reporter component initiator.

In one form of the invention, the steps of providing a reporter component initiator; and providing a modulator; occur after the steps of providing the first, second and third agents.

In a particularly advantageous form of the invention, the first, second and third agents are provided by way of co-expression in a cell, to which the modulator is introduced.

In a third aspect, the present invention provides a method for determining whether and/or the extent to which a test compound interacts with a second protein when the second protein is associated with a first protein, the method comprising the steps of:
a). contacting said test compound with a system comprising:
i). a first agent, comprising the first protein coupled to a first reporter component;
ii). a second agent, comprising an interacting group coupled to a second reporter component;
iii). a third agent, comprising the second protein;
wherein proximity of the first and second reporter components generates a signal; and wherein the modulator modulates the association of the interacting group with the second protein;
b). determining the signal as a determination of whether and/or the extent to which said test compound interacts with a second protein when the second protein is associated with a first protein.

In one embodiment, the second protein is a receptor, and the third aspect of the invention comprises a method for determining whether a test compound is an agonist of the second protein when the second protein is associated with the first protein, and the step of determining the signal as a determination of whether and/or the extent to which said test compound interacts with a second protein when the second protein is associated with a first protein more specifically comprises the step of detecting an increase in the signal as a determination of whether and/or the extent to which the test compound is an agonist of the second protein when the second protein is associated with the first protein.

The first protein may also be a receptor.

In one embodiment, the second protein is a receptor, and the third aspect of the invention comprises a method for determining whether and/or the extent to which a test compound is an antagonist or partial agonist of the second protein when the second protein is associated with the first protein, the method comprising the steps of:
a). contacting said test compound with a system comprising:
i). a first agent, comprising the first protein coupled to a first reporter component;
ii). a second agent, comprising an interacting group coupled to a second reporter component;
iii). a third agent, comprising the second protein;
iv). an agonist of the second protein;
wherein proximity of the first and second reporter components generates a signal; and wherein the modulator modulates the association of the interacting group with the second protein;
b). detecting a decrease in the signal as a determination of whether and/or the extent to which the test compound is an antagonist or partial agonist of the second protein when the second protein is associated with the first protein.

The first protein may also be a receptor.

In one embodiment, the second protein is a constitutively active receptor, and the third aspect of the invention comprises a method for determining whether and/or the extent to which a test compound is an inverse agonist of the second protein when the second protein is associated with the first protein, and the step of determining the signal as a determination of whether and/or the extent to which said test compound interacts with a second protein when the second protein is associated with a first protein more specifically comprises the step of detecting a decrease in the signal as a determination of whether the test compound is an inverse agonist of the second protein when the second protein is associated with the first protein.

In one embodiment, where the first and second proteins are both receptors, present invention comprises a method for screening a test compound for first protein/second protein hetero-dimer/-oligomer selective activity, the method comprising the steps of:
a) determining whether, and/or the extent to which, the test compound interacts with the second protein while the second protein is associated with the first protein; and
b) if the test compound interacts with the second protein while the second protein is associated with the first protein, determining whether, or the extent to which the test compound interacts with the second protein in the absence of the first protein;
such that a test compound that exhibits greater affinity and/or potency and/or efficacy when interacting with the second protein while the second protein is associated with the first protein is selective for the first protein/second protein hetero-dimer/-oligomer.

In one embodiment, where the first and second proteins are both receptors, present invention comprises a method for screening a test compound for first protein/second protein hetero-dimer/-oligomer selective antagonism or partial agonism, the method comprising the steps of:
a) determining whether, and/or the extent to which, the test compound is an antagonist or partial agonist of the first protein/second protein hetero-dimer/-oligomer, by contacting said test compound with a system comprising:

i). a first agent, comprising the first protein coupled to a first reporter component;

ii). a second agent, comprising an interacting group coupled to a second reporter component;

iii). a third agent, comprising the second protein;

iv). an agonist of the first protein, the second protein and/or the first protein/second protein hetero-dimer/-oligomer;

wherein proximity of the first and second reporter components generates a signal; and wherein the modulator modulates the association of the interacting group with the second protein;

b). detecting a decrease in the signal as a determination of whether and/or the extent to which the test compound is an antagonist or partial agonist of the first protein/second protein hetero-dimer/-oligomer;

c) if the test compound is an antagonist or partial agonist of the first protein/second protein hetero-dimer/-oligomer, determining whether, or the extent to which the test compound interacts with the second protein in the absence of the first protein and the first protein in the absence of the second protein; such that a test compound that exhibits greater agonistic or partial agonistic properties when interacting with the first protein/second protein hetero-dimer/-oligomer is selective for the first protein/second protein hetero-dimer/-oligomer.

In one embodiment, where the first and second proteins are both receptors, there is provided a method for screening a test compound for first protein/second protein hetero-dimer/-oligomer selective antagonism or partial agonism, the method comprising the steps of:

a) determining whether, and/or the extent to which, the test compound is an antagonist or partial agonist of the first protein/second protein hetero-dimer/-oligomer, by contacting said test compound with a system comprising:

i). a first agent, comprising the second protein coupled to a first reporter component;

ii). a second agent, comprising an interacting group coupled to a second reporter component;

iii). a third agent, comprising the first protein;

iv). an agonist of the second protein, the first protein and/or the first protein/second protein hetero-dimer/-oligomer;

wherein proximity of the first and second reporter components generates a signal; and wherein the modulator modulates the association of the interacting group with the first protein;

b). detecting a decrease in the signal as a determination of whether and/or the extent to which the test compound is an antagonist or partial agonist of the first protein/second protein hetero-dimer/-oligomer;

c) if the test compound is an antagonist or partial agonist of the first protein/second protein hetero-dimer/-oligomer, determining whether, or the extent to which the test compound is an antagonist or partial agonist of the first protein in the absence of the second protein and the second protein in the absence of the first protein; such that a test compound that exhibits greater antagonistic or partial agonistic properties when interacting with the first protein/second protein hetero-dimer/-oligomer is selective for the first protein/second protein hetero-dimer/-oligomer.

In one embodiment, where the first and second proteins are both receptors, there is provided a method for screening a test compound for first protein/second protein hetero-dimer/-oligomer selective inverse agonism, the method comprising the steps of:

a) determining whether, and/or the extent to which, the test compound is an inverse agonist of the first protein/second protein hetero-dimer/-oligomer, by contacting said test compound with a system comprising:

i). a first agent, comprising the first protein coupled to a first reporter component;

ii). a second agent, comprising an interacting group coupled to a second reporter component;

iii). a third agent, comprising a constitutively active second protein;

wherein proximity of the first and second reporter components generates a signal; and wherein the modulator modulates the association of the interacting group with the second protein;

b) detecting a decrease in the signal as a determination of whether and/or the extent to which the test compound is an inverse agonist of the first protein/second protein hetero-dimer/-oligomer;

c) if the test compound is an inverse agonist of the first protein/second protein hetero-dimer/-oligomer, determining whether, or the extent to which the test compound is an inverse agonist of the first protein in the absence of the second protein and the second protein in the absence of the first protein; such that a test compound that exhibits greater inverse agonistic properties when interacting with the first protein/second protein hetero-dimer/-oligomer is selective for the first protein/second protein hetero-dimer/-oligomer.

In one embodiment, where the first and second proteins are both receptors, there is provided a method for screening a test compound for first protein/second protein hetero-dimer/-oligomer selective inverse agonism, the method comprising the steps of:

a) determining whether, and/or the extent to which, the test compound is an inverse agonist of the first protein/second protein hetero-dimer/-oligomer, by contacting said test compound with a system comprising:

i). a first agent, comprising the second protein coupled to a first reporter component;

ii). a second agent, comprising an interacting group coupled to a second reporter component;

iii). a third agent, comprising a constitutively first protein;

wherein proximity of the first and second reporter components generates a signal; and wherein the modulator modulates the association of the interacting group with the first protein;

b) detecting a decrease in the signal as a determination of whether and/or the extent to which the test compound is an inverse agonist of the first protein/second protein hetero-dimer/-oligomer;

c) if the test compound is an inverse agonist of the first protein/second protein hetero-dimer/-oligomer, determining whether, or the extent to which the test compound is an inverse agonist of the second protein in the absence of the first protein and the first protein in the absence of the second protein; such that a test compound that exhibits greater inverse agonistic properties when interacting with the first protein/second protein hetero-dimer/-oligomer is selective for the first protein/second protein hetero-dimer/-oligomer.

In a fourth aspect of the invention, there is provided a kit for the detection of the molecular associations, the kit comprising:

i). a first agent, comprising a first interacting group coupled to a first reporter component;

ii). a second agent, comprising a second interacting group coupled to a second reporter component;

iii). a third agent, comprising a third interacting group;

iv). a modulator; and wherein proximity of the first and second reporter components generates a signal capable of detection; and wherein the modulator modulates the association of the second interacting group with the third interacting group.

In one form of the invention, the kit further comprises a reporter component initiator, and proximity of the first and second reporter components generates a signal capable of detection only in the presence of the reporter component initiator.

In one form of the invention, the modulator increases the propensity of the second interacting group to associate with the third interacting group, such that detection of the signal generated by proximity of the first and second reporter components by the detector constitutes detection of the association of the first and third agents.

It should be understood that the modulator may interact with either the first, second or third interacting groups, or simultaneously with both first and third interacting groups, or simultaneously with second and third interacting groups, to modulate the association of the second interacting group with the third interacting group.

In an alternate form of the invention, the modulator decreases the propensity of the second interacting group to associate with the third interacting group, such that detection of a reduction of the signal generated by proximity of the first and second reporter components by the detector constitutes detection of the dissociation of the first and third agents.

In a highly advantageous form of the invention, the first interacting group differs from the third interacting group. Thus, in this form, detection of the signal generated by the proximity of the first and second reporter components constitutes detection of the hetero-dimerisation and/or -oligomerisation of the first and third interacting groups.

In a preferred form of the invention, the third agent does not comprise a component capable of generating a signal that substantially interferes with and/or contributes to the signal generated by the proximity of the first and second reporter components. Thus, in this form, detection of the signal generated by the proximity of the first and second reporter components is facilitated.

In some systems, such as where the first and third interacting groups are expressed at low levels, and/or where the selected combination of the first and second reporter components generates a weak signal, facilitation of the detection of the signal in accordance with the preferred form of the invention described above may render an assay viable or, even more advantageously, amenable to high throughput screening.

In a preferred form of the invention, the third agent is selected from the group: receptors, ion channels, enzymes, carriers, transporters, integral membrane proteins, cytoskeletal proteins, adhesion molecules, signalling proteins, scaffolding proteins, accessory proteins, trafficking proteins, transcription factors, nuclear co-factors and nucleic acid molecules, as defined below.

In a preferred form of the invention, the modulator is a ligand or an enzyme.

In a preferred form of the invention, the third agent is produced by expression in a cell. Where the third agent is produced by expression in a cell, the method of the invention may be carried out in whole cells, cellular fractions or in a cell-free system.

In a particularly advantageous embodiment of the invention, the first and third interacting groups are provided in the form of receptors, and the modulator is provided in the form of a ligand that modulates the receptor of the third interacting group, such that modulation of the signal generated by proximity of the first and second reporter components by the modulator is indicative of association of the receptors of the first and third interacting groups.

In a fifth aspect of the invention, there is provided a method for screening a test compound for selective activity against a heterodimer of a first protein and a second protein, the method comprising the steps of:

a) contacting said test compound at increasing concentrations with a system comprising:
  i). a first agent, comprising the first protein coupled to a first reporter component;
  ii). a second agent, comprising an interacting group coupled to a second reporter component;
  iii). a third agent, comprising the second protein;
  wherein proximity of the first and second reporter components generates a signal; and wherein the modulator modulates the association of the interacting group with the second protein;

b). determining signal as a determination of whether said test compound modulates said association of the interacting group with the second protein at each concentration to produce a dose-response curve;

c). determining the Hill slope of the dose-response curve, wherein, a Hill slope in excess of 1 indicates interaction of the test compound with the hetero-dimer.

In a sixth aspect of the invention, there is provided a first protein-second protein hetero-dimer/-oligomer identified by any one of the systems, methods or kits of the invention.

In a seventh aspect of the invention, there is provided a hetero-dimeric or hetero-oligomeric receptor, comprising at least one first receptor subunit associated with at least one second receptor subunit, identified by any one of the systems, methods or kits of the invention.

In an eighth aspect of the invention, there is provided a method for the treatment of a patient suffering from a first receptor-related ailment by administering a therapeutically effective amount of a second receptor agonist, inverse agonist or antagonist, wherein the first and second receptors form a hetero-dimer/-oligomer identified by any one of the systems, methods or kits of the invention.

In one embodiment, the second receptor agonist, inverse agonist or antagonist is co-administered with a first receptor agonist, inverse agonist or antagonist.

In a ninth aspect of the invention, there is provided a method for the treatment of a patient suffering from a second receptor-related ailment by administering a therapeutically effective amount of a first receptor agonist, inverse agonist or antagonist, wherein the first and second receptors form a hetero-dimer/-oligomer identified by any one of the systems, methods or kits of the invention.

In one embodiment, the first receptor agonist, inverse agonist or antagonist is co-administered with a second receptor agonist, inverse agonist or antagonist.

In a tenth aspect of the invention, there is provided a method for the manufacture of a medicament for the treatment of a patient suffering from an first receptor-related ailment comprising use of a therapeutically effective amount of a second receptor agonist, inverse agonist or antagonist, wherein the first and second receptors form a hetero-dimer/-oligomer identified by any one of the systems, methods or kits of the invention.

The medicament may also contain a first receptor agonist, inverse agonist or antagonist.

In an eleventh aspect of the invention, there is provided a method for the manufacture of a medicament for the treatment of a patient suffering from a second receptor-related ailment comprising use of a therapeutically effective amount of an first receptor agonist, inverse agonist or antagonist, wherein the first and second receptors form a hetero-dimer/-oligomer identified by any one of the systems, methods or kits of the invention.

The medicament may also contain a second receptor agonist, inverse agonist or antagonist.

In a twelfth aspect of the invention, there is provided a method for the treatment of a patient suffering from a first receptor-related ailment by administering a therapeutically effective amount of a selective second receptor agonist, antagonist or inverse agonist binding agent, or fragment thereof, wherein the first and second receptors form a hetero-dimer/-oligomer identified by any one of the systems, methods or kits of the preceding claims.

The selective second receptor agonist, antagonist or inverse agonist binding agent may be an antibody, including a humanised antibody, a polyclonal antibody, a monoclonal antibody, a chimeric antibody, a CDR-grafted antibody and/or an anti-idiotypic antibody.

In a thirteenth aspect of the invention, there is provided a method for the treatment of a patient suffering from a second receptor-related ailment by administering a therapeutically effective amount of a selective first receptor agonist, antagonist or inverse agonist binding agent, or fragment thereof, wherein the first and second receptors form a hetero-dimer/-oligomer identified by any one of the systems, methods or kits of the preceding claims.

The selective first receptor agonist, antagonist or inverse agonist binding agent may be an antibody, including a humanised antibody, a polyclonal antibody, a monoclonal antibody, a chimeric antibody, a CDR-grafted antibody and/or an anti-idiotypic antibody.

In a fourteenth aspect of the invention, there is provided a method for the treatment of a patient suffering from a second receptor-related ailment by administering a therapeutically effective amount of a selective first receptor agonist, antagonist or inverse agonist binding agent, or fragment thereof, wherein the first and second receptors form a hetero-dimer/-oligomer identified by any one of the systems, methods or kits of the preceding claims.

The selective first receptor agonist, antagonist or inverse agonist binding agent may be an antibody, including a humanised antibody, a polyclonal antibody, a monoclonal antibody, a chimeric antibody, a CDR-grafted antibody and/or an anti-idiotypic antibody.

In a fifteenth aspect of the invention, there is provided an agonist of the second protein, when the second protein is associated with the first protein, identified by the methods of the invention.

In a sixteenth aspect of the invention, there is provided an antagonist or partial agonist of the second protein, when the second protein is associated with the first protein, identified by the methods of the invention.

In a seventeenth aspect of the invention, there is provided an inverse agonist of the second protein, when the second protein is associated with the first protein, identified by the methods of the invention.

In a eighteenth aspect of the invention, there are provided selective agonists and/or antagonists and/or inverse agonists of the first protein-second protein hetero-dimer/-oligomer identified by the methods of the invention.

eBRET measurements at 37C were carried out on HEK293 cells transiently co-expressing TRHR/Rluc and barr2/Venus with either pcDNA3, orexin receptor 2 (OxR2), CXC chemokine receptor 2 (CXCR2), hemagglutin epitope-tagged melanocortin receptor 3 or 4 (HA-MC3R or HA-MC4R), or dopamine D2 receptor long form (D2LR) or short form (D2SR) following the treatment of each with their respective ligands. The different ligand treatment ($10^{-6}$M) for each receptor was thyrotropin releasing hormone (TRH) for TRHR/Rluc (with pcDNA3); orexin A (OxA) for OxR2; interleukin-8 (IL-8) for CXCR2; alpha-melanocyte-stimulating hormone (a-MSH) for HA-MC3R, HA-MC4R; and bromocriptine (BROM) for D2LR and D2SR.

Figure 5:
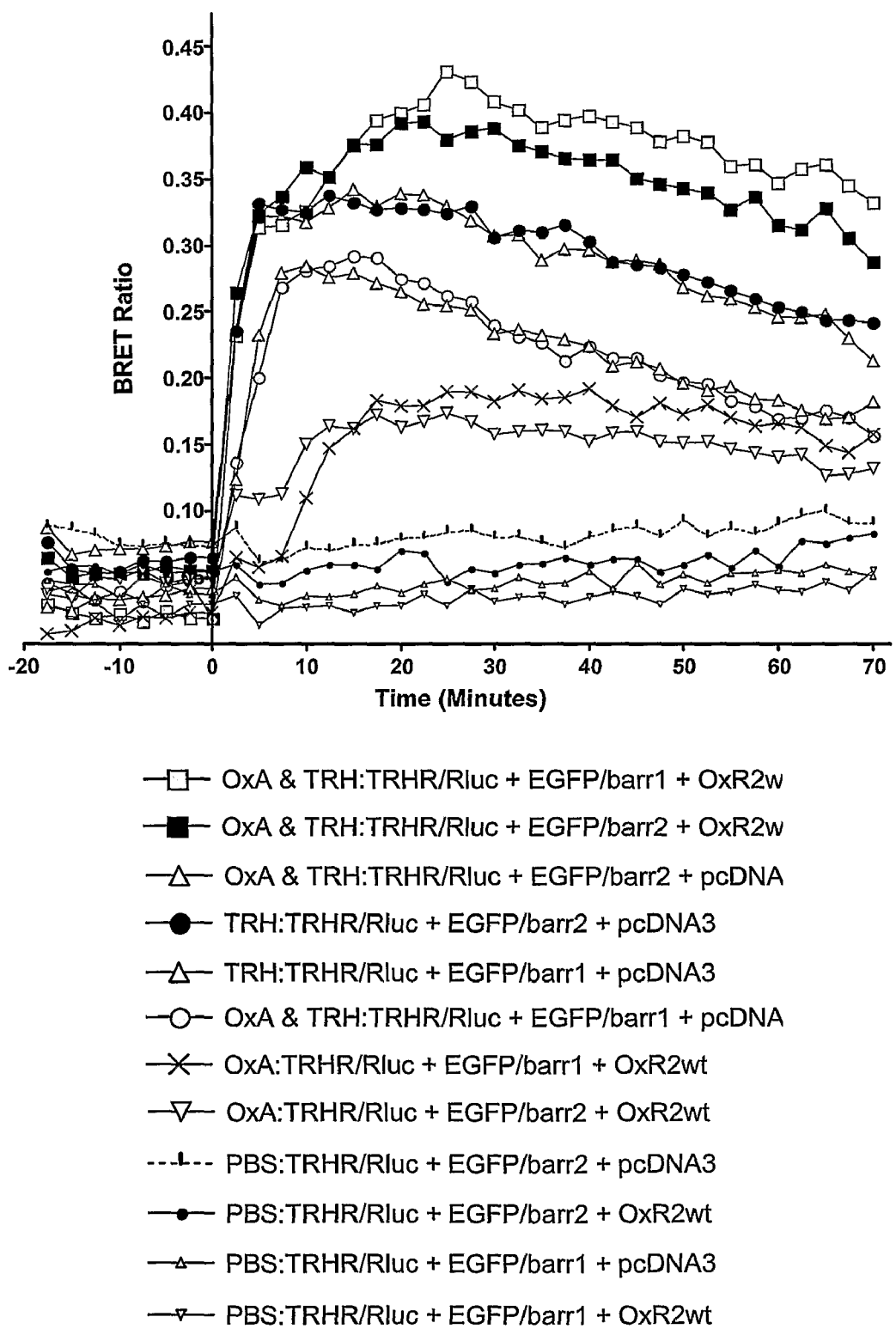

FIG. 5 shows the thyrotropin releasing hormone receptor (TRHR) as IG1, Rluc as RC1, either beta-arrestin 1 (barr1) or beta-arrestin 2 (barr2) as IG2, EGFP as RC2 and OxR2 as IG3. eBRET measurements at 37C were carried out on HEK293 cells transiently co-expressing TRHR/Rluc and EGFP/barr1 or EGFP/barr2 with either pcDNA3 or OxR2. Ligand treatments were either OxA or TRH only or both OxA and TRH combined. Phosphate-buffered saline (PBS) was used as a vehicle control.

Figure 6:
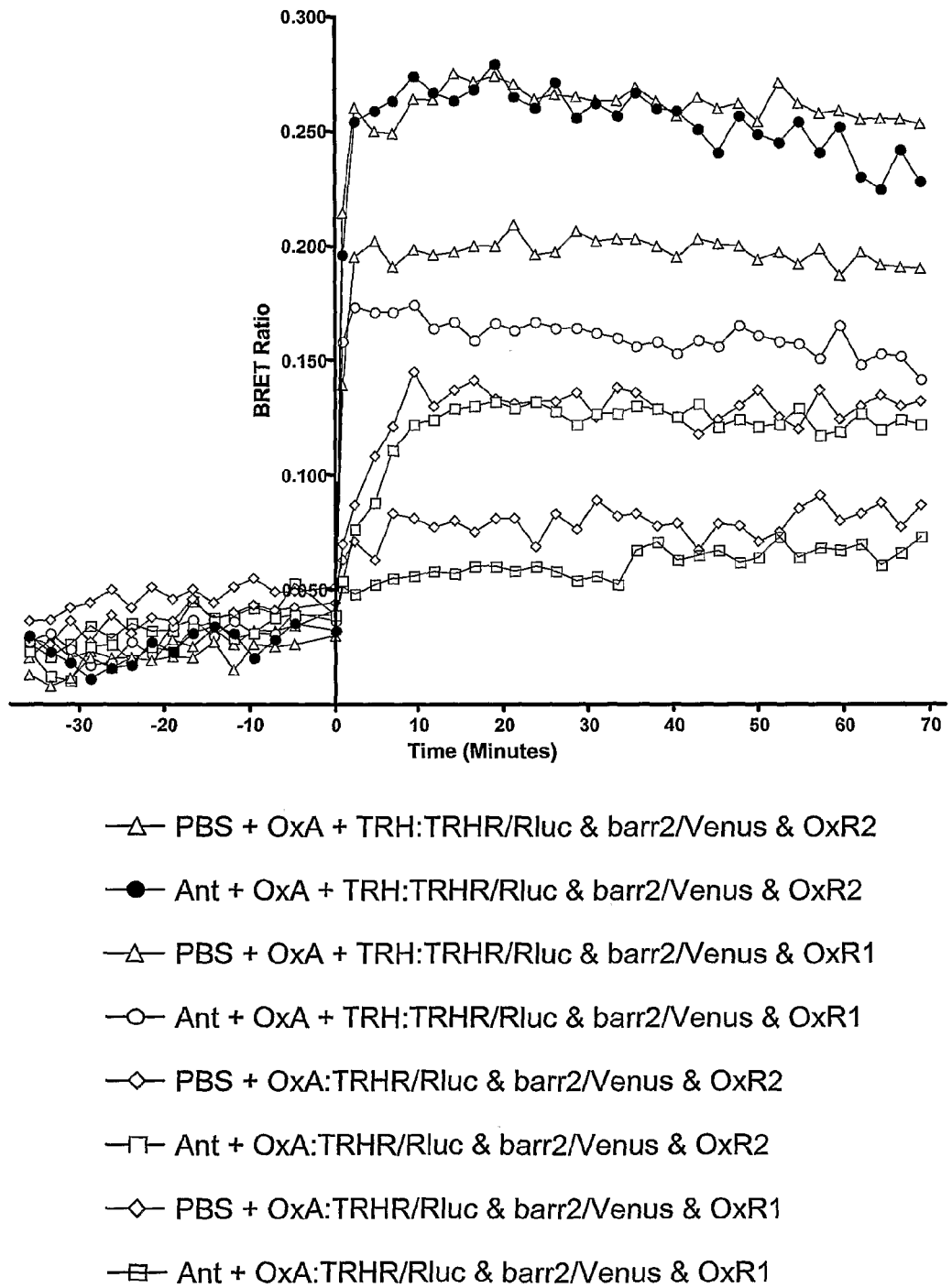

FIG. 6 shows the thyrotropin releasing hormone receptor (TRHR) as IG1, Rluc as RC1, beta-arrestin 2 (barr2) as IG2, Venus as RC2 and OxR1 or OxR2 as IG3. eBRET measurements were carried out at 37C on HEK293 cells transiently co-expressing TRHR/Rluc and barr2/Venus with either pcDNA3, OxR1 or OxR2 following pretreatment with $10^{-6}$M OxR1-selective antagonist, SB-334867-A, for approximately 40 minutes and then $10^{-6}$M OxA (IG3 ligand; modulator) or $10^{-6}$M TRH (IG1 ligand), or both, was added. Where antagonist was not preincubated, cells were treated with PBS instead for the same amount of time.

Figure 7:
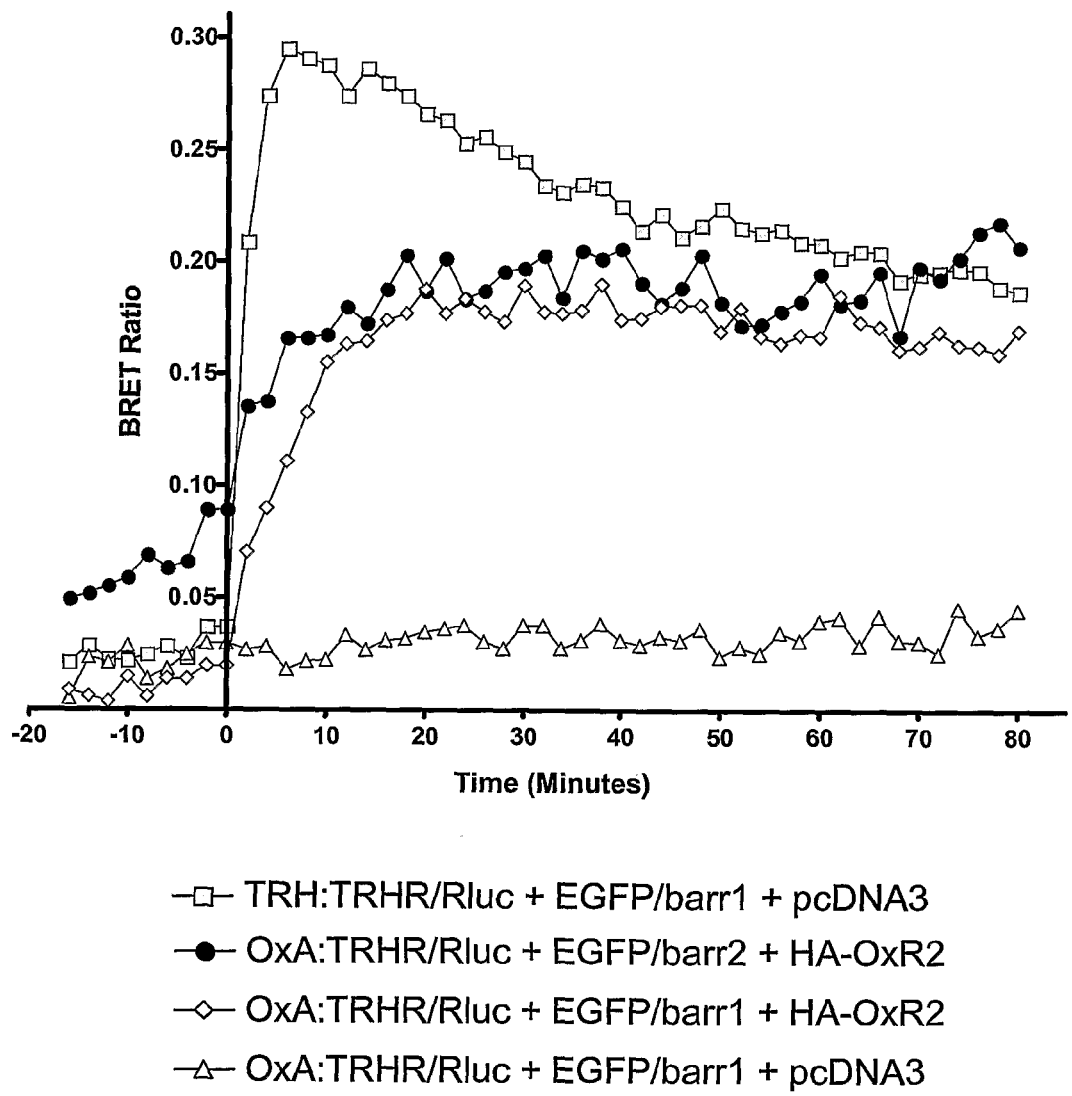

FIG. 7 shows the thyrotropin releasing hormone receptor (TRHR) as IG1, Rluc as RC1, beta-arrestin 1 (barr1) or beta-arrestin 2 (barr2) as IG2, EGFP as RC2 and hemagglutin epitope-tagged OxR2 (HA-OxR2) as IG3. eBRET measurements at 37C were carried out on HEK293 cells transiently co-expressing TRHR/Rluc and EGFP/barr1 or EGFP/barr2 with either pcDNA3 or HA-OxR2. Ligand treatments were either OxA or TRH only. Phosphate-buffered saline (PBS) was used as a vehicle control.

Figure 8:
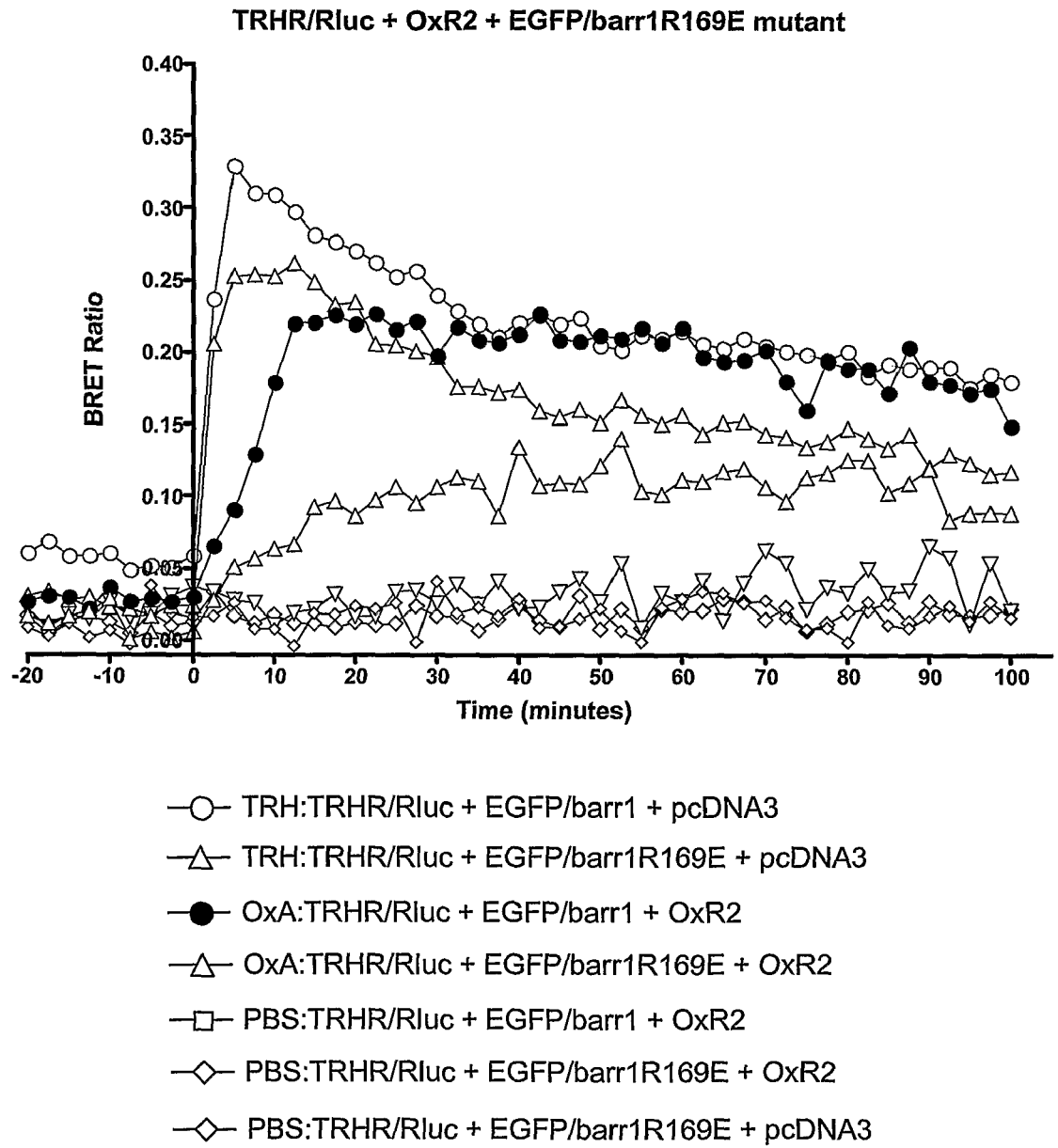

FIG. 8 shows the thyrotropin releasing hormone receptor (TRHR) as IG1, Rluc as RC1, beta-arrestin 1 (barr1) or beta-arrestin 1 phosphorylation-independent mutant R169E (barr1R169E) as IG2, EGFP as RC2 and OxR2 as IG3. eBRET measurements at 37C were carried out on HEK293 cells transiently co-expressing TRHR/Rluc and EGFP/barr1 or EGFP/barr1R169E with either pcDNA3 or OxR2. Ligand treatments were either OxA or TRH only. Phosphate-buffered saline (PBS) was used as a vehicle control.

Figure 9:
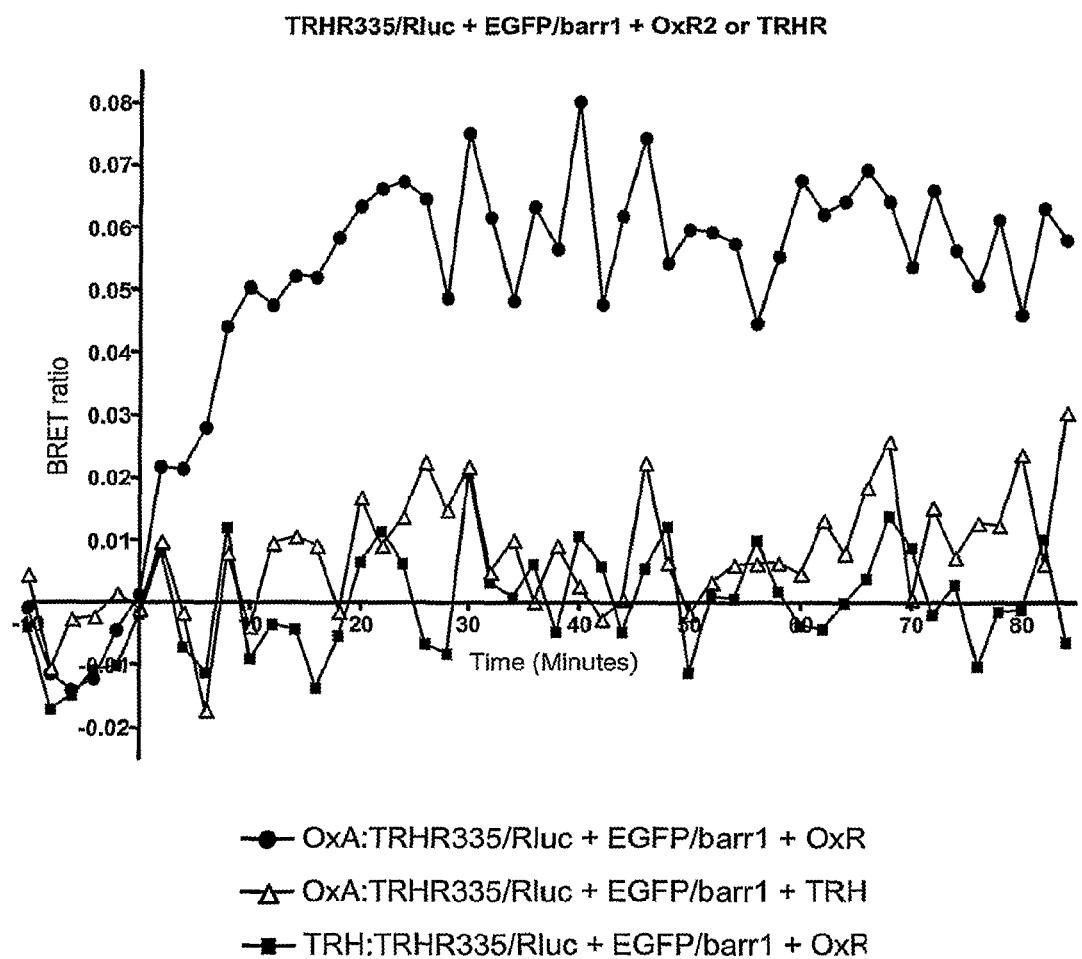

FIG. 9 shows the thyrotropin releasing hormone receptor truncated at amino acid 335 (TRHR335) as IG1, Rluc as RC1, beta-arrestin 1 (barr1) as IG2, EGFP as RC2 and OxR2 or TRHR as IG3. eBRET measurements at 37C were carried out on HEK293 cells transiently co-expressing TRHR335/Rluc and EGFP/barr1 with either OxR2 or TRHR. Ligand treatments were either OxA or TRH only.

Figure 10:
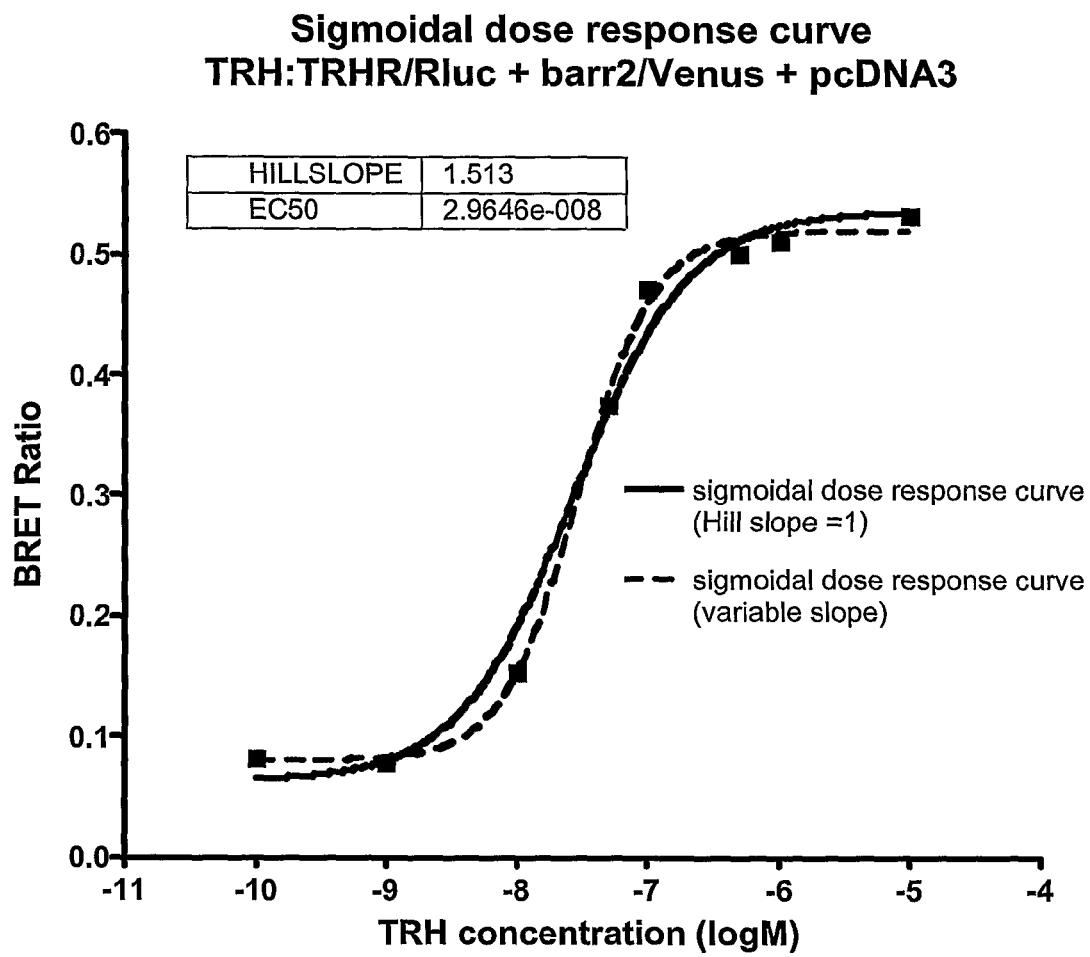

FIG. 10 shows a dose-response curve for the thyrotropin releasing hormone receptor (TRHR) as IG1, Rluc as RC1, beta-arrestin 2 (barr2) as IG2, Venus as RC2 and in the absence of IG3. BRET measurements at 37C were carried out on HEK293 cells transiently co-expressing TRHR/Rluc, barr2/Venus and pcDNA3 with increasing doses of TRH. Sigmoidal dose response curves were plotted using Prism (GraphPad), either assuming a Hill slope of 1 or allowing for variable slope. The $EC_{50}$ and Hill slope values for the variable slope curve are included in a table in the graph.

Figure 11:
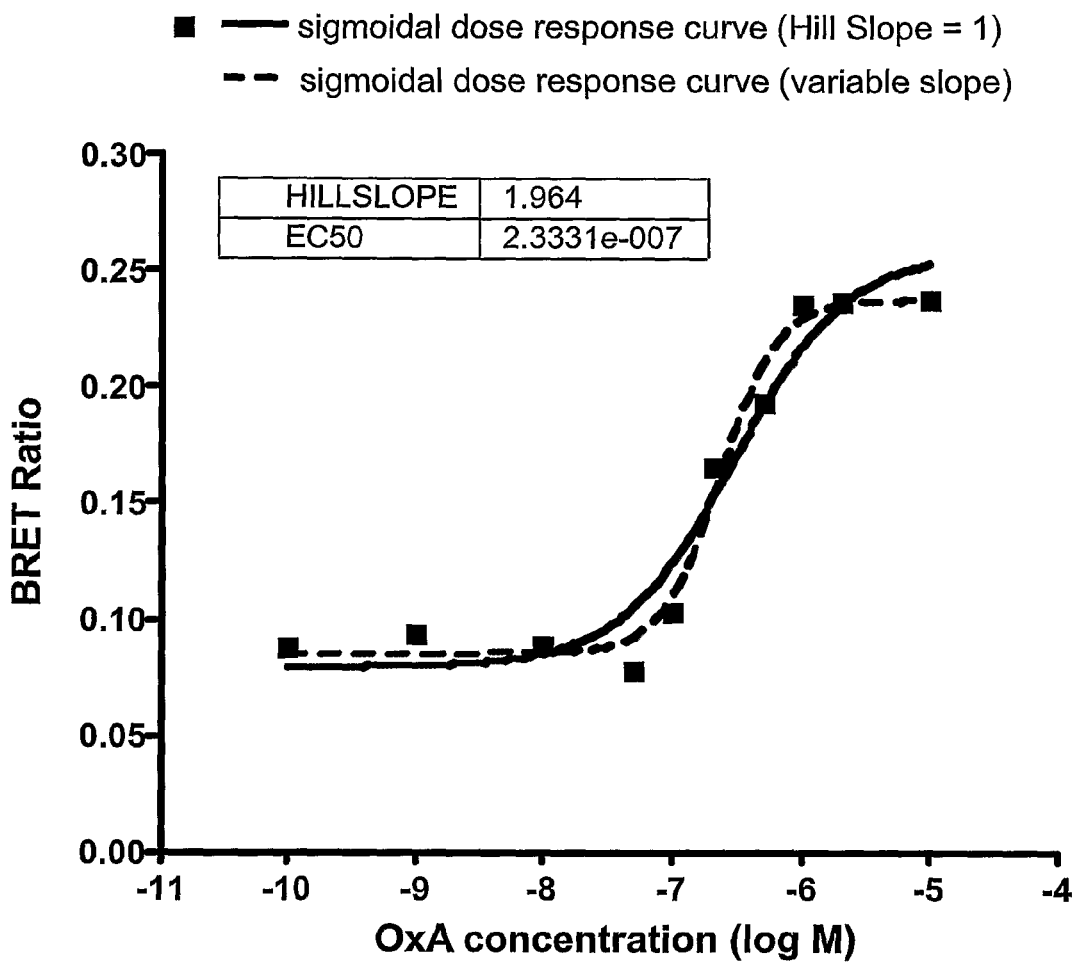

FIG. 11 shows a dose-response curve for OxR2 as IG1, Rluc as RC1, barr2 as IG2, Venus as RC2 and in the absence of IG3. BRET measurements at 37C were carried out on HEK293 cells transiently co-expressing OxR2/Rluc, barr2/Venus and pcDNA3 with increasing doses of OxA. Sigmoidal dose response curves were plotted using Prism (GraphPad), either assuming a Hill slope of 1 or allowing for variable slope. The $EC_{50}$ and Hill slope values for the variable slope curve are included in a table in the graph.

Figure 12:
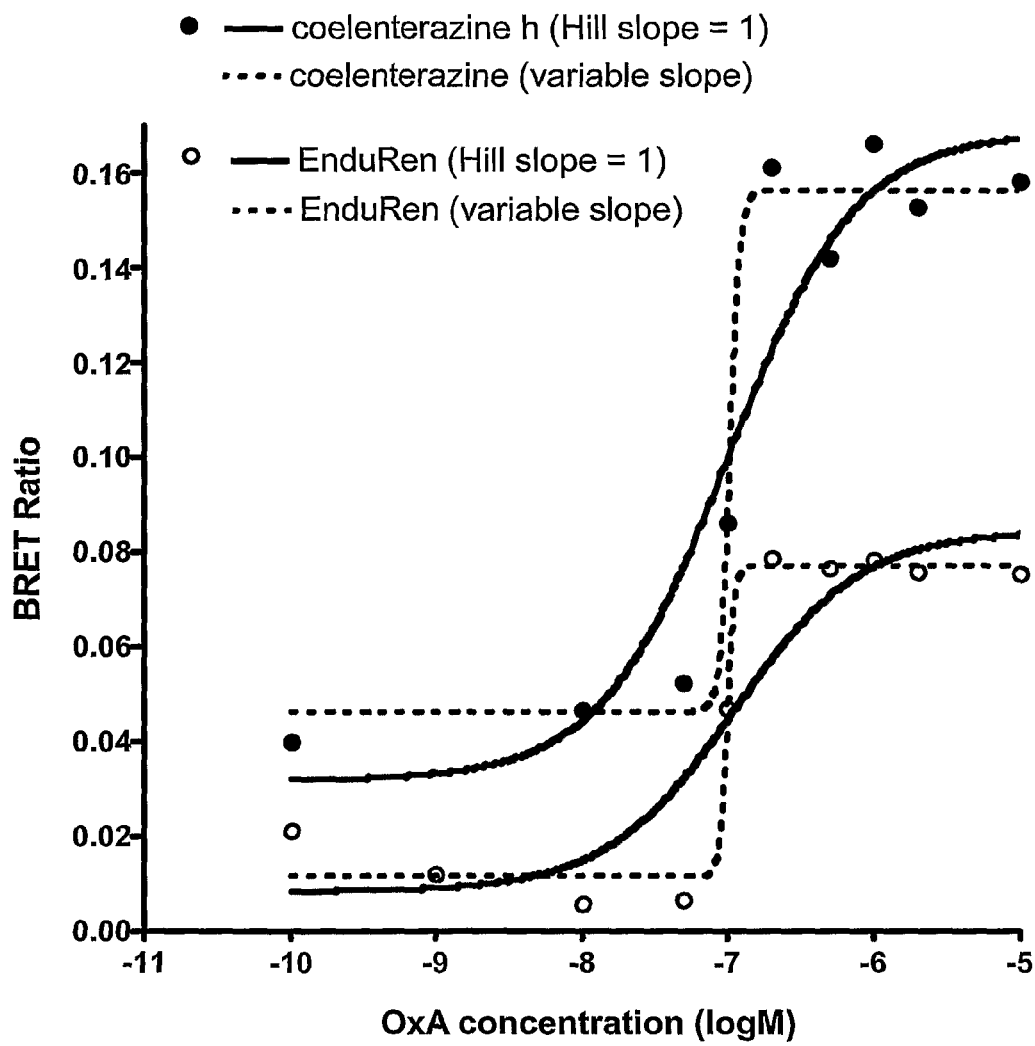

FIG. 12 shows dose-response curves for the thyrotropin releasing hormone receptor (TRHR) as IG1, Rluc as RC1, beta-arrestin 2 (barr2) as IG2, Venus as RC2 and OxR2 as IG3. BRET measurements at 37C were carried out on HEK293 cells transiently co-expressing TRHR/Rluc, barr2/Venus and OxR2 with increasing doses of OxA. Sigmoidal dose response curves were plotted using Prism (GraphPad), either assuming a Hill slope of 1 or allowing for variable slope. The $EC_{50}$ and Hill slope values for the variable slope curves are included in a table in the graph. Curves generated using coelenterazine h and EnduRen as two forms of Rluc substrate (reporter component initiator) are shown.

Figure 13:
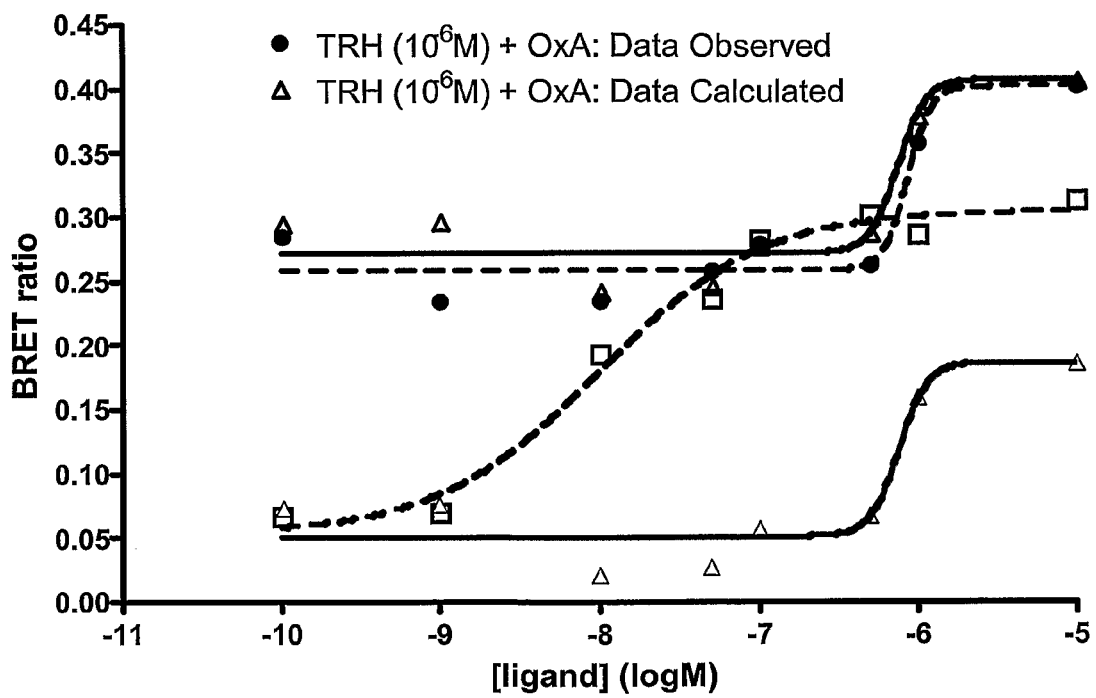

FIG. 13 shows dose-response curves for TRHR as IG1, Rluc as RC1, barr1 as IG2, EGFP as RC2 in the presence or absence of OxR2 as IG3. BRET measurements at 37C were carried out on HEK293 cells transiently co-expressing TRHR/Rluc and EGFP/barr1 in the absence of OxR2 with increasing doses of TRH, as well as HEK293 cells transiently co-expressing TRHR/Rluc and EGFP/barr1 with OxR2 with increasing doses of OxA with and without $10^{-6}$M TRH. A curve mathematically generated by addition of the ligand-induced signal generated with $10^{-6}$M TRH (from the TRH: TRHR/Rluc+EGFP/barr1 curve) to each of the points generated for the OxA: TRHR/Rluc+EGFP/barr1+OxR2 curve is also plotted (TRHR/Rluc+EGFP/barr1+OxR2: TRH ($10^{-6}$ M)+OxA: Data calculated).

Figure 14:
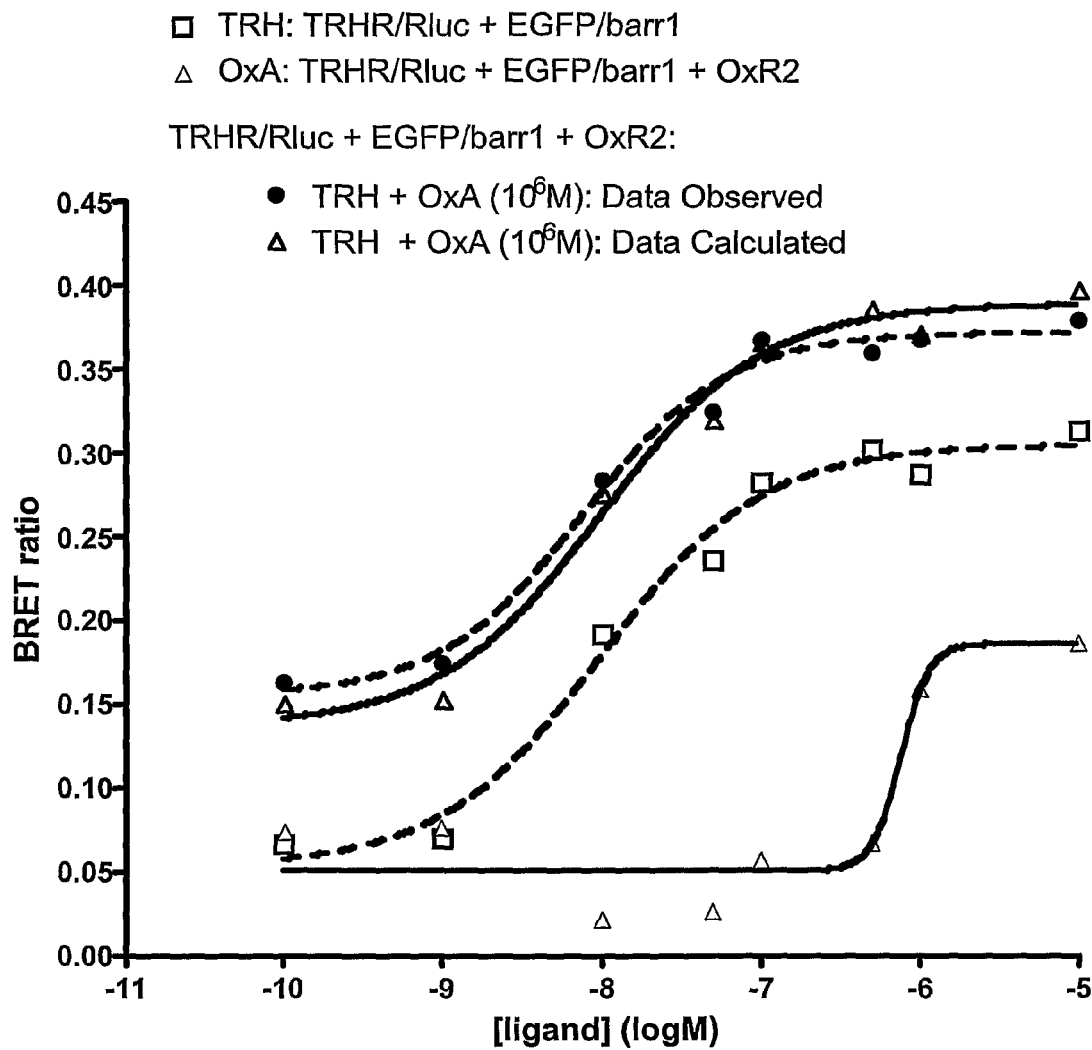

FIG. 14 shows dose-response curves for TRHR as IG1, Rluc as RC1, barr1 as IG2, EGFP as RC2 in the presence or absence of OxR2 as IG3. BRET measurements at 37C were carried out on HEK293 cells transiently co-expressing TRHR/Rluc and EGFP/barr1 in the absence of OxR2 with increasing doses of TRH, as well as HEK293 cells transiently co-expressing TRHR/Rluc and EGFP/barr1 with OxR2 with increasing doses of OxA, or increasing doses of TRH with $10^{-6}$M OxA. A curve mathematically generated by addition of the ligand-induced signal generated with $10^{-6}$M OxA (from the OxA: TRHR/Rluc+EGFP/barr1+OxR2 curve) to each of the points generated for the TRH: TRHR/Rluc+EGFP/barr1 curve is also plotted (TRHR/Rluc+EGFP/barr1+OxR2: TRH+OxA ($10^{-6}$M): Data calculated).

Figure 15:
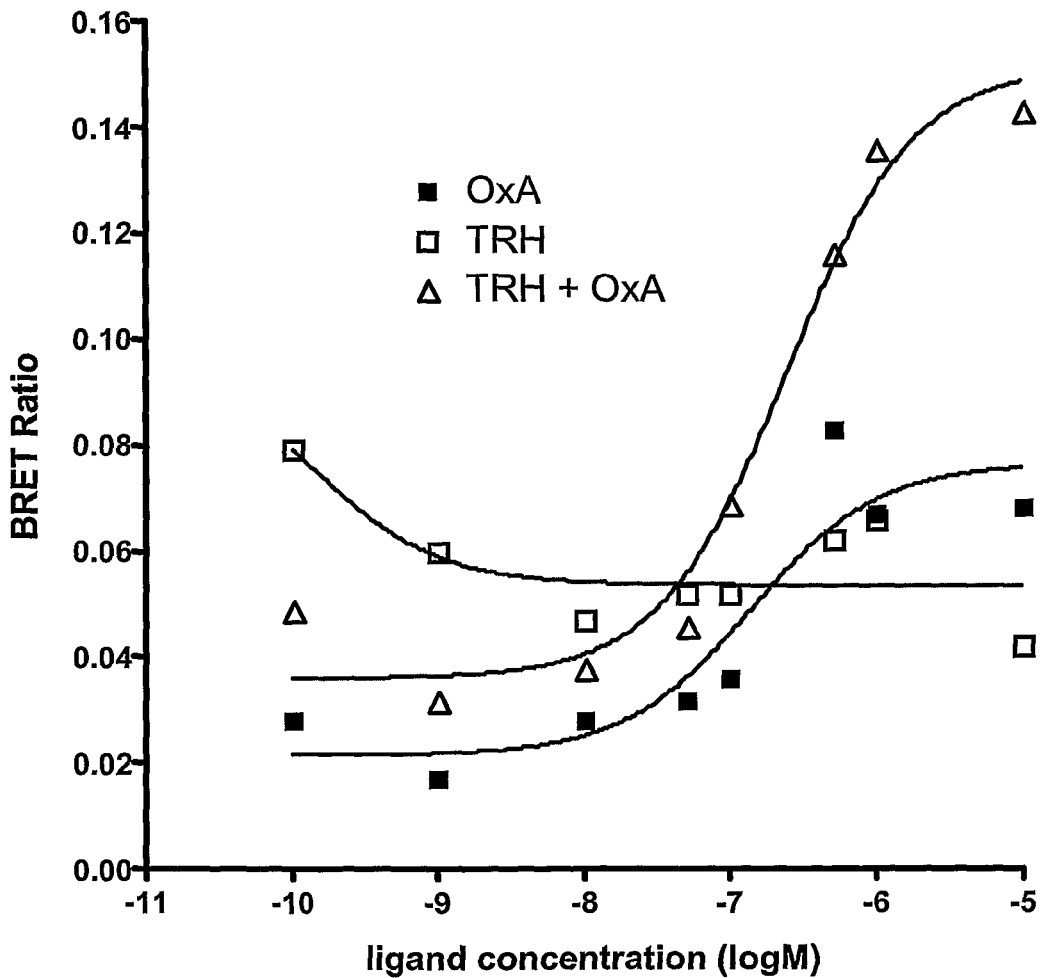

FIG. 15 shows dose response curves for TRHR335 as IG1, Rluc as RC1, barr2 as IG2, Venus as RC2 and OxR2 as IG3. BRET measurements at 37C were carried out on HEK293 cells transiently co-expressing TRHR335/Rluc, barr2/Venus and OxR2 with increasing doses of TRH and OxA alone or in combination.

Figure 16:
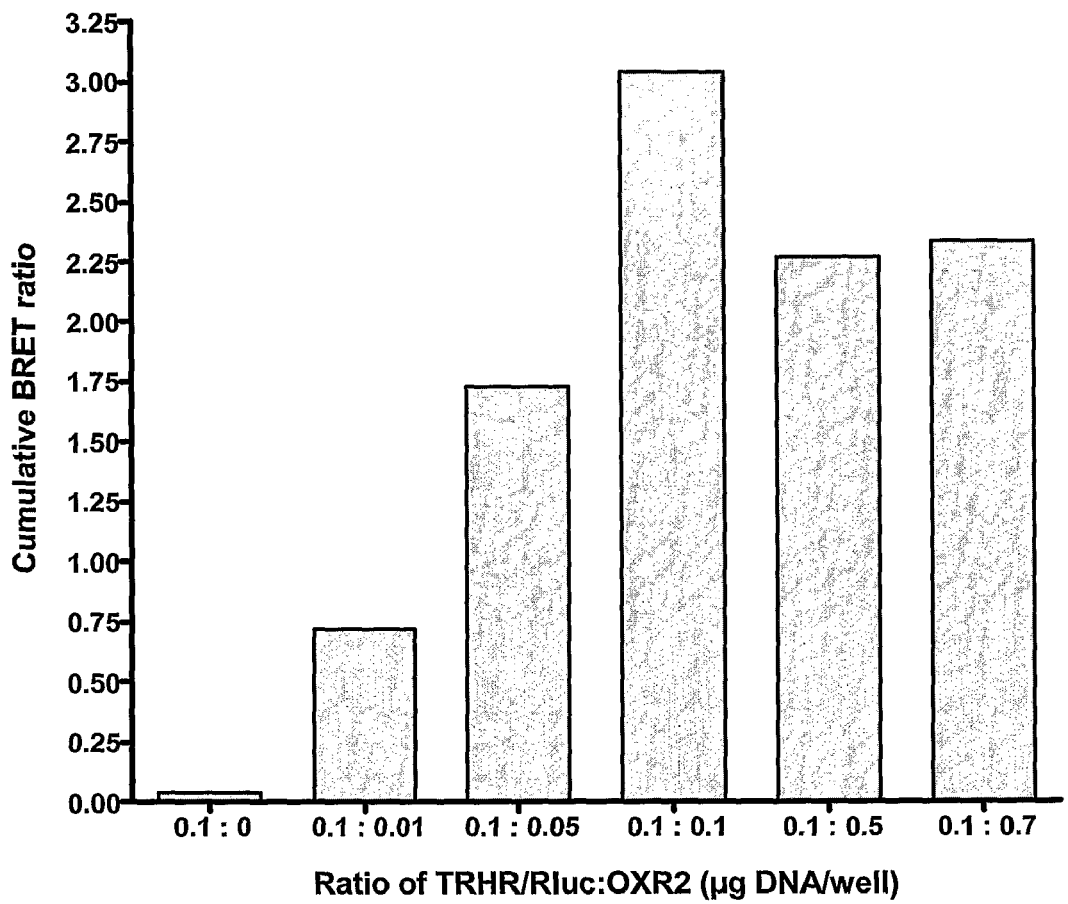

FIG. 16 shows cumulative eBRET reads over time for each combination of receptors (IG1 and IG3; data captured over 83 mins). TRHR is IG1, Rluc is RC1, barr1 is IG2, EGFP is RC2 and OxR2 is IG3. The same amount of EGFP/barr1 (IG2-RC2) is transfected for each experiment. TRHR/Rluc (IG1-RC1) is transfected at a constant amount (0.1 μg DNA/well) while OxR2 (IG3) is transfected at varying amounts of DNA (0, 0.01, 0.05, 0.1, 0.5, 0.7 μg DNA/well). eBRET measurements at 37C were carried out on HEK293 cells following addition of $10^{-6}$M OxA (modulator) to each well. The signal is only detected when OxR2 (IG3) is expressed (no signal was recorded at 0 μg OxR2).

Figure 17:
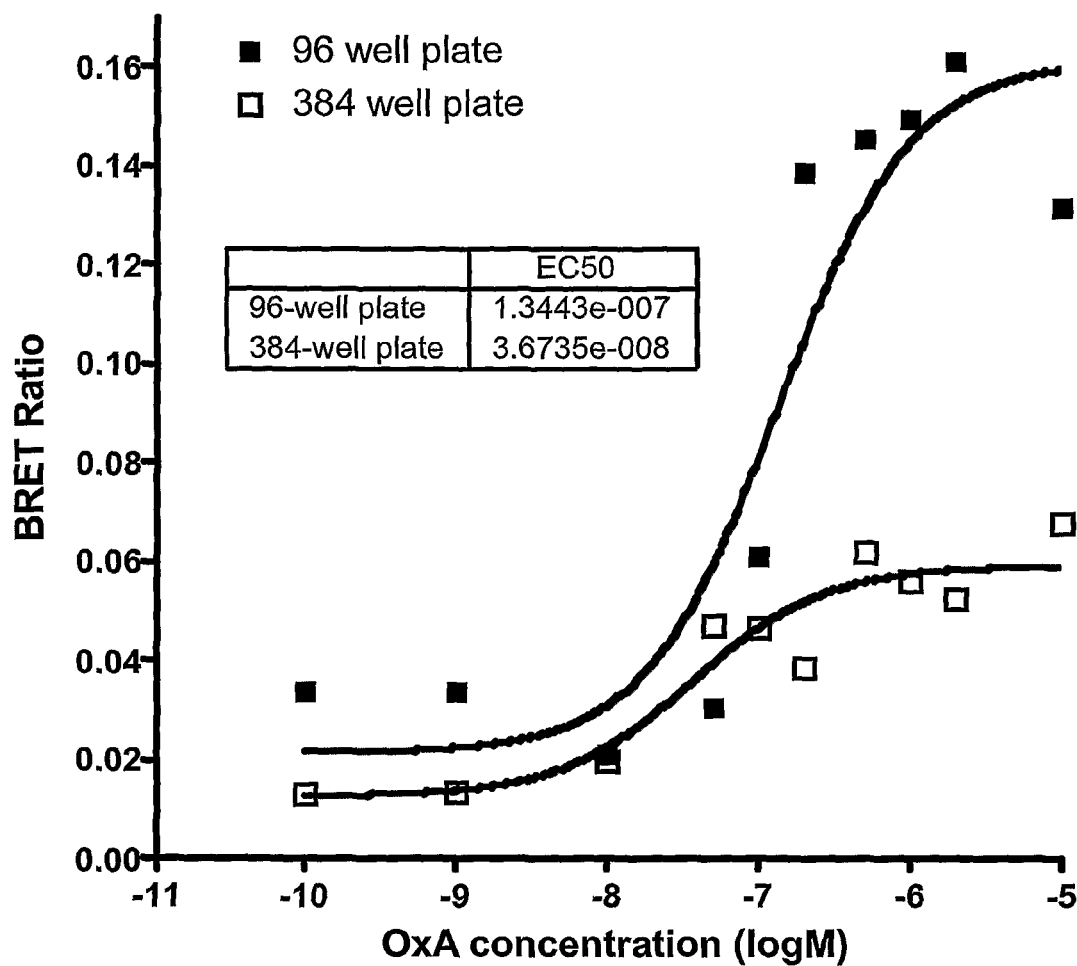

FIG. 17 shows dose response curves for TRHR as IG1, Rluc as RC1, barr2 as IG2, Venus as RC2 and OxR2 as IG3. BRET measurements at 37C were carried out on HEK293 cells transiently co-expressing TRHR/Rluc, barr2/Venus and OxR2 with increasing doses of OxA in either 96-well or 384-well microplates.

Figure 18:
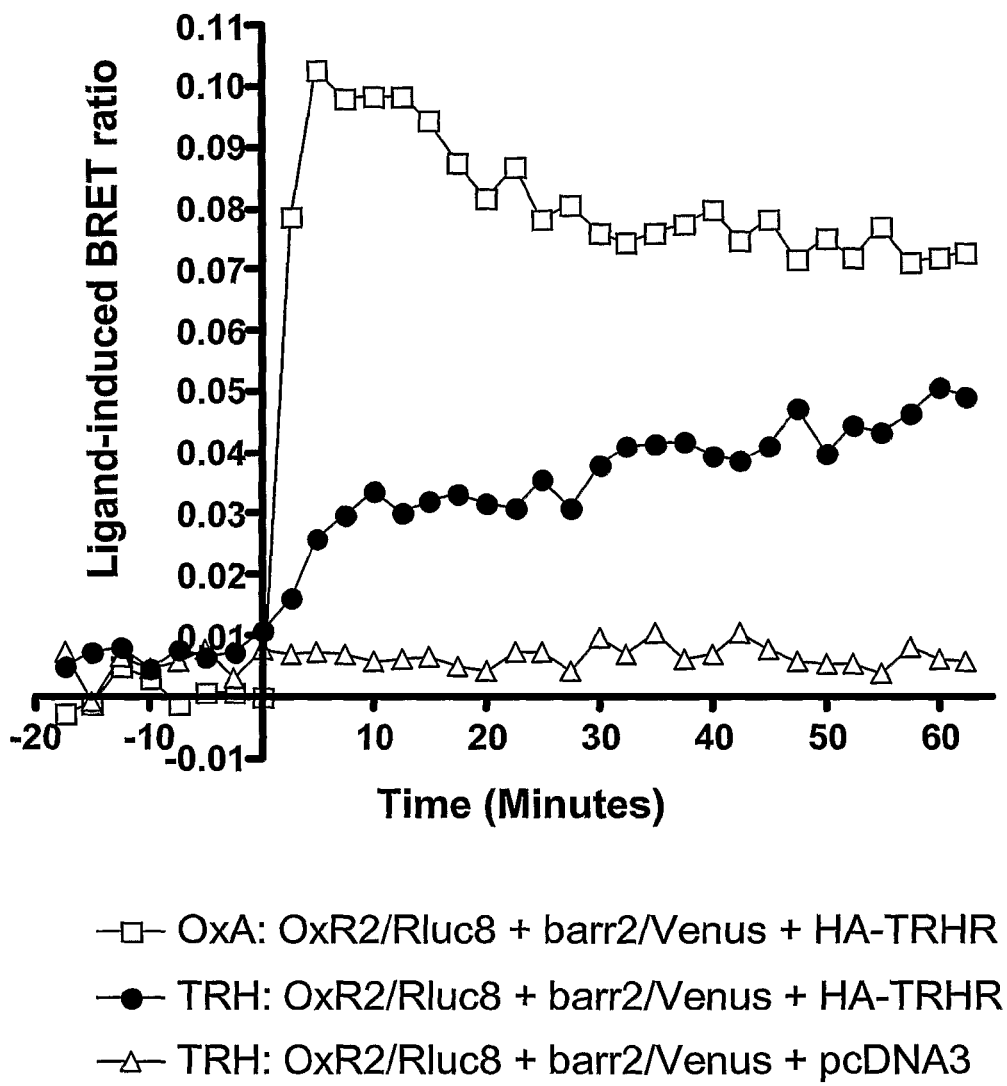

FIG. 18 shows OxR2 as IG1, Rluc8 as RC1, beta-arrestin 2 (barr2) as IG2, Venus as RC2 and hemagglutin epitope-tagged TRHR (HA-TRHR) as IG3. eBRET measurements at 37C were carried out on HEK293 cells transiently co-expressing OxR2/Rluc8 and barr2/Venus with either pcDNA3 or HA-TRHR. Ligand treatments were either OxA or TRH only. Phosphate-buffered saline (PBS) was used as a vehicle control. Data presented as ligand-induced BRET ratios.

Figure 19:
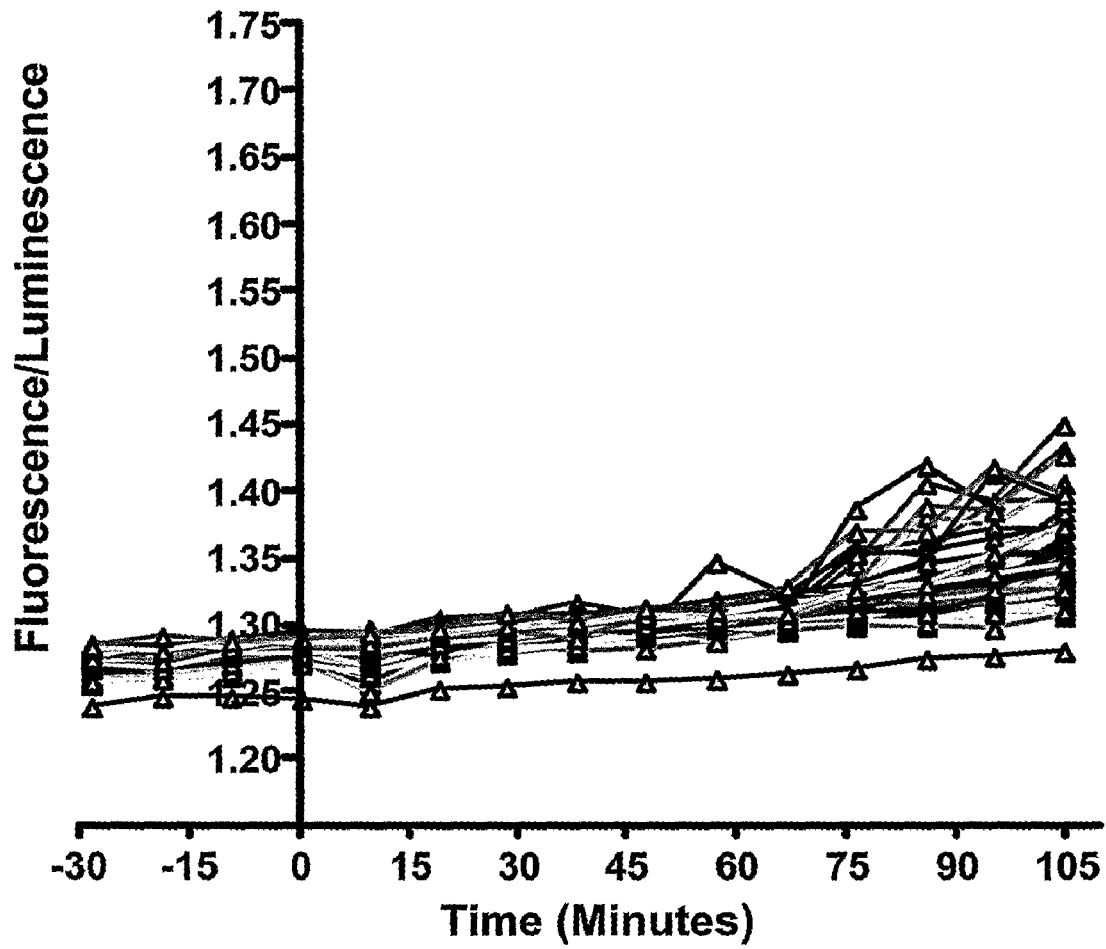

FIG. 19 shows the thyrotropin releasing hormone receptor (TRHR) as IG1, Rluc8 as RC1, beta-arrestin 2 (barr2) as IG2, Venus as RC2 and hemagglutin epitope-tagged OxR2 (HA-OxR2) as IG3. eBRET measurements at 37C were carried out on HEK293 cells transiently co-expressing TRHR/Rluc8 and barr2/Venus with HA-OxR2 aliquoted into all wells of a 96-well plate. Phosphate-buffered saline (PBS) was added to the first two rows and the last two rows of the 96-well plate (48 wells in total) as a vehicle control. Data presented as fluorescence/luminescence.

Figure 20:
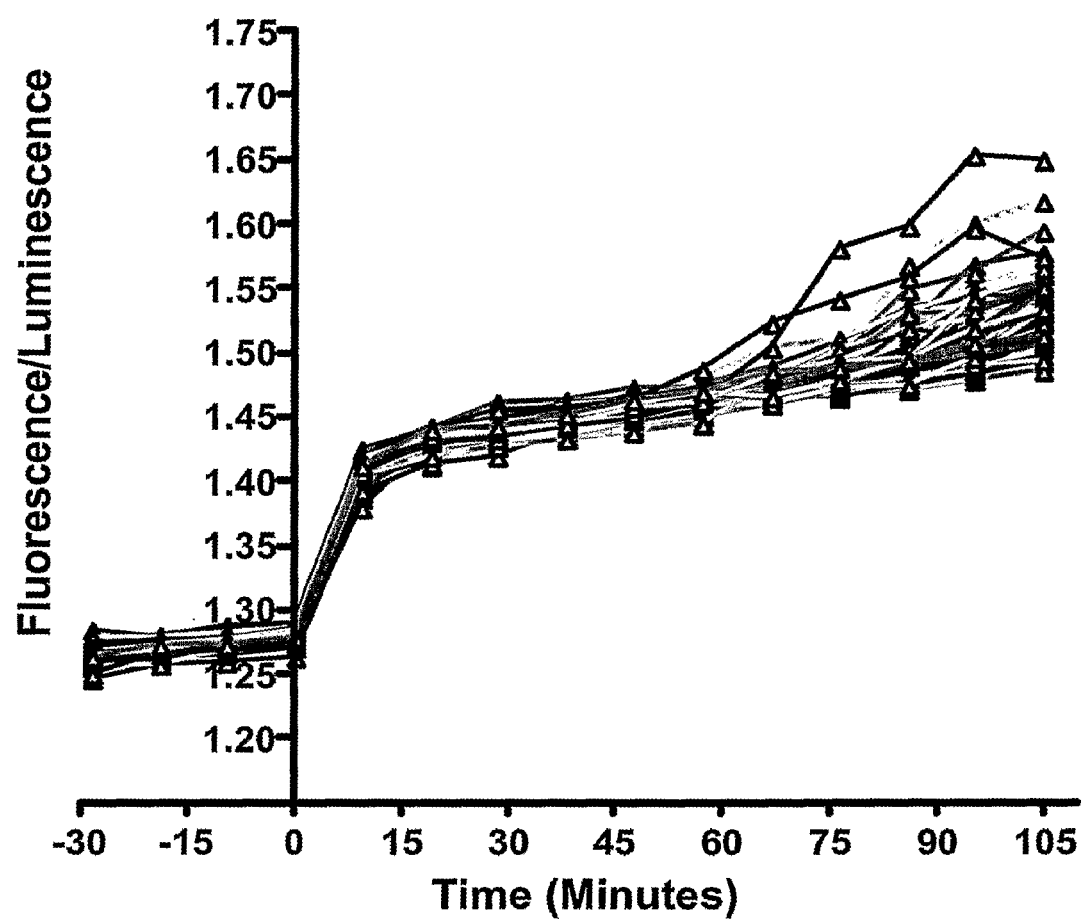

FIG. 20 shows the thyrotropin releasing hormone receptor (TRHR) as IG1, Rluc8 as RC1, beta-arrestin 2 (barr2) as IG2, Venus as RC2 and hemagglutin epitope-tagged OxR2 (HA-OxR2) as IG3. eBRET measurements at 37C were carried out on HEK293 cells transiently co-expressing TRHR/Rluc8 and barr2/Venus with HA-OxR2 aliquoted into all wells of a 96-well plate. OxA was added to the middle four rows of the 96-well plate (48 wells in total). Data presented as fluorescence/luminescence.

Figure 21:
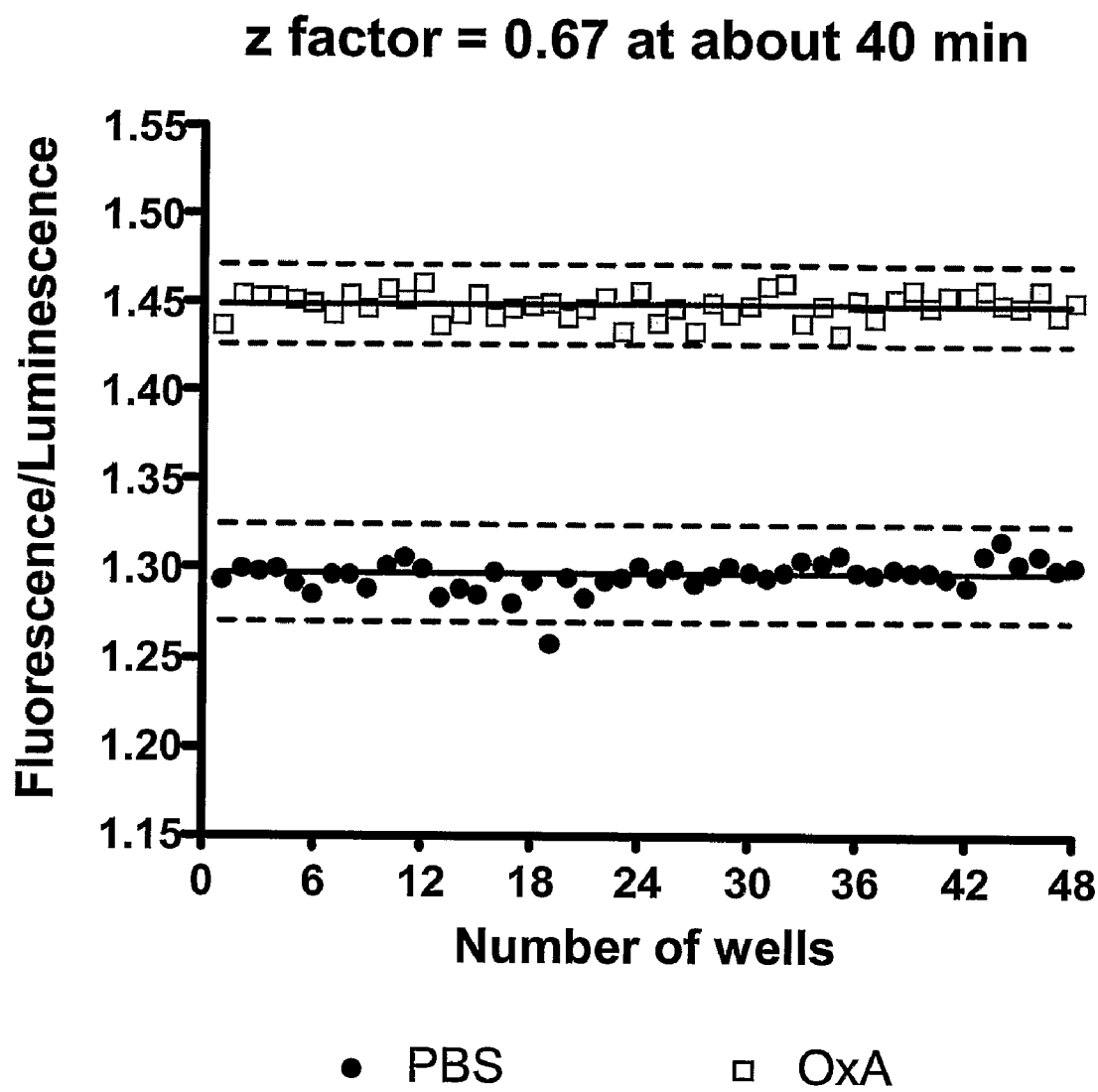

FIG. 21 shows z-factor data for the thyrotropin releasing hormone receptor (TRHR) as IG1, Rluc8 as RC1, beta-arrestin 2 (barr2) as IG2, Venus as RC2 and hemagglutin epitope-tagged OxR2 (HA-OxR2) as IG3. As shown in FIGS. 19 and 20, eBRET measurements at 37C were carried out on HEK293 cells transiently co-expressing TRHR/Rluc8 and barr2/Venus with HA-OxR2 aliquoted into all wells of a 96-well plate. Phosphate-buffered saline (PBS) was added to the first two rows and the last two rows of the 96-well plate (48 wells in total) as a vehicle control. OxA was added to the middle four rows of the 96-well plate (48 wells in total). Data presented as fluorescence/luminescence.

Figure 22:
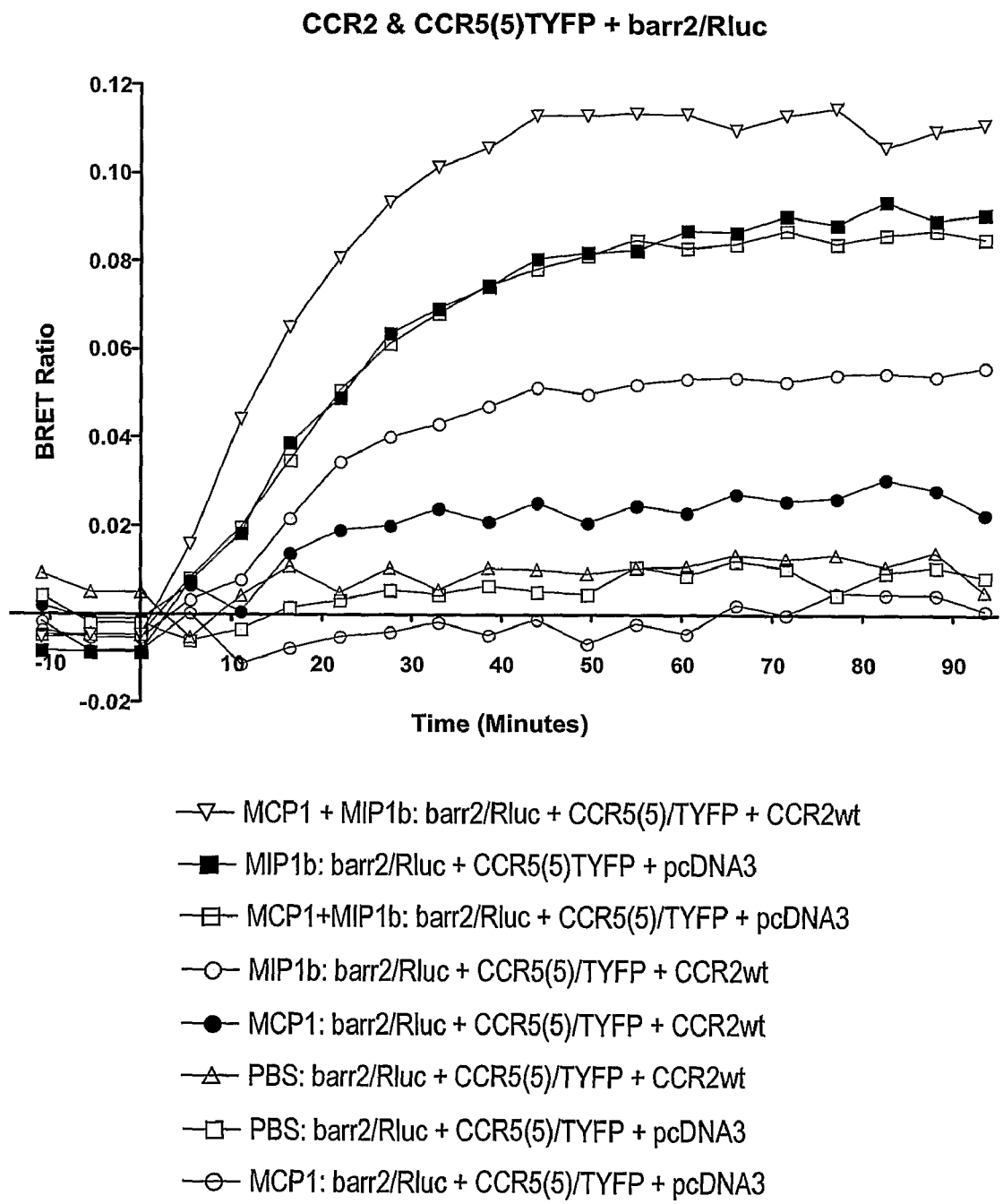

FIG. 22 shows CC chemokine receptor 5 (CCR5) as IG1, Topaz (TYFP) as RC1, beta-arrestin 2 (barr2) as IG2, Rluc as RC2 and CC chemokine receptor 2 (CCR2) as IG3. eBRET measurements at 37C were carried out on HEK293 cells transiently co-expressing CCR5(5)TYFP (contains a 5 amino acid linker between CCR5 and TYFP) and barr2/Rluc either with CCR2 or pcDNA3. Ligand treatments were either monocyte chemoattractant protein 1 (MCP1; CCR2 selective ligand), macrophage inflammatory protein 1b (MIP1b; CCR5 selective ligand), or both MCP1 and MIP1b combined. Phosphate-buffered saline (PBS) was used as a vehicle control.

Figure 23:
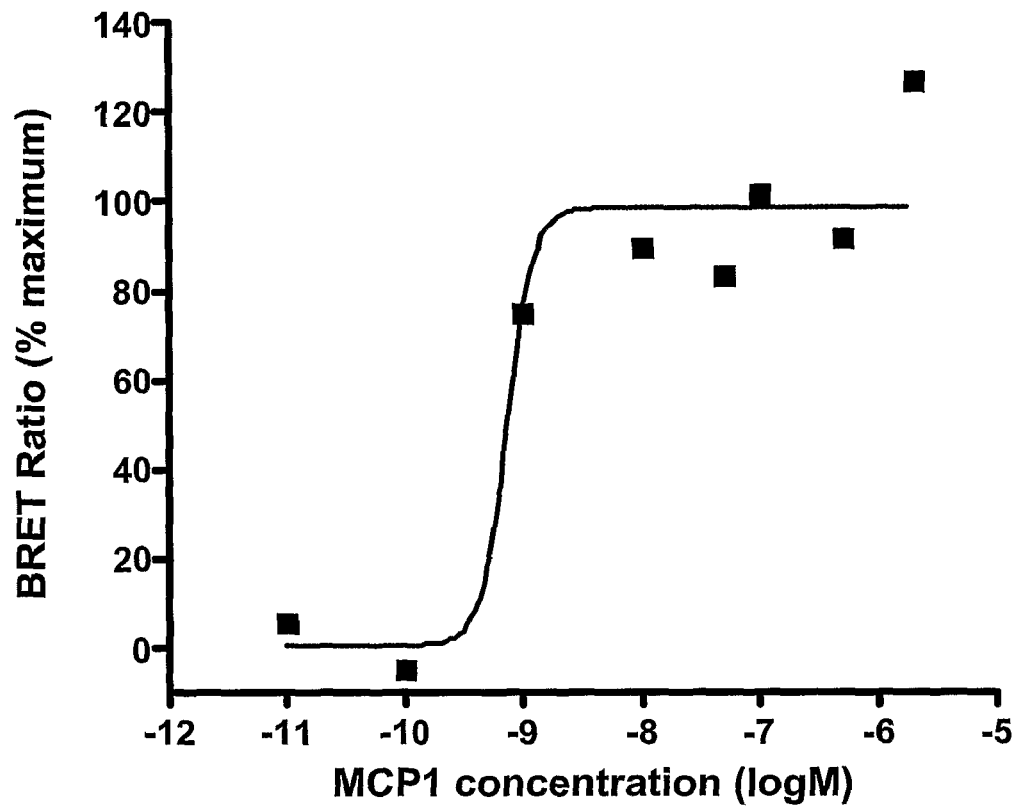

FIG. 23 shows a dose-response curve for the CC chemokine receptor 5 (CCR5) as IG1, Topaz (TYFP) as RC1, beta-arrestin 2 (barr2) as IG2, Rluc as RC2 and CC chemokine receptor 2 (CCR2) as IG3. BRET measurements at 37C were carried out on HEK293 cells transiently co-expressing CCR5 (5)TYFP (contains a 5 amino acid linker between CCR5 and TYFP), barr2/Rluc and CCR2 treated with increasing doses of monocyte chemoattractant protein 1 (MCP1; CCR2 selective ligand). A sigmoidal dose response curve was plotted using Prism (GraphPad) allowing for variable slope.

Figure 24:
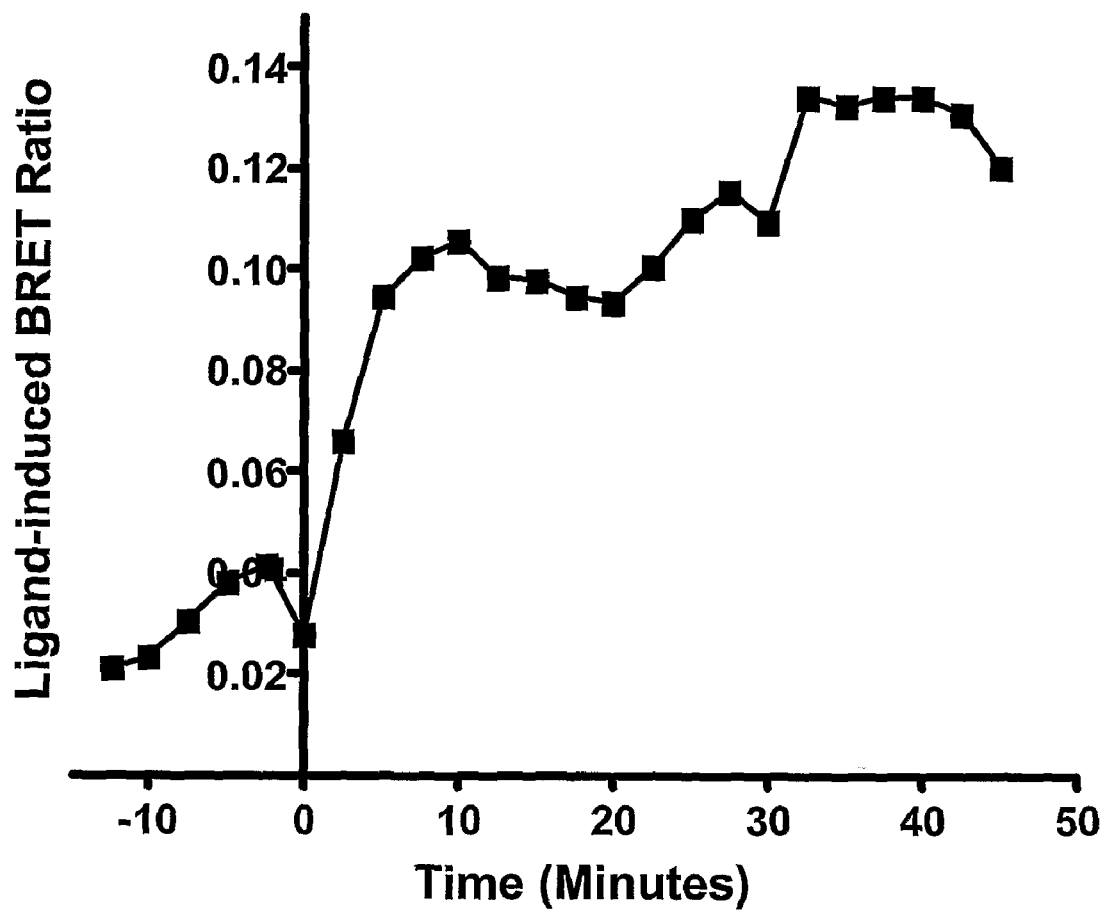

FIG. 24 shows bradykinin B2 receptor (B2R) as IG1, Rluc8 as RC1, beta-arrestin 2 (barr2) as IG2, Venus as RC2 and hemagglutin epitope-tagged angiotensin 11 receptor type 1 (HA-AT1R) as IG3. eBRET measurements at 37C were carried out on HEK293 cells transiently co-expressing B2R/Rluc8, barr2/Venus and HA-AT1R treated with Angiotensin II (AngII). Phosphate-buffered saline (PBS) was used as a vehicle control. Data presented as ligand-induced BRET ratio.

Figure 25:
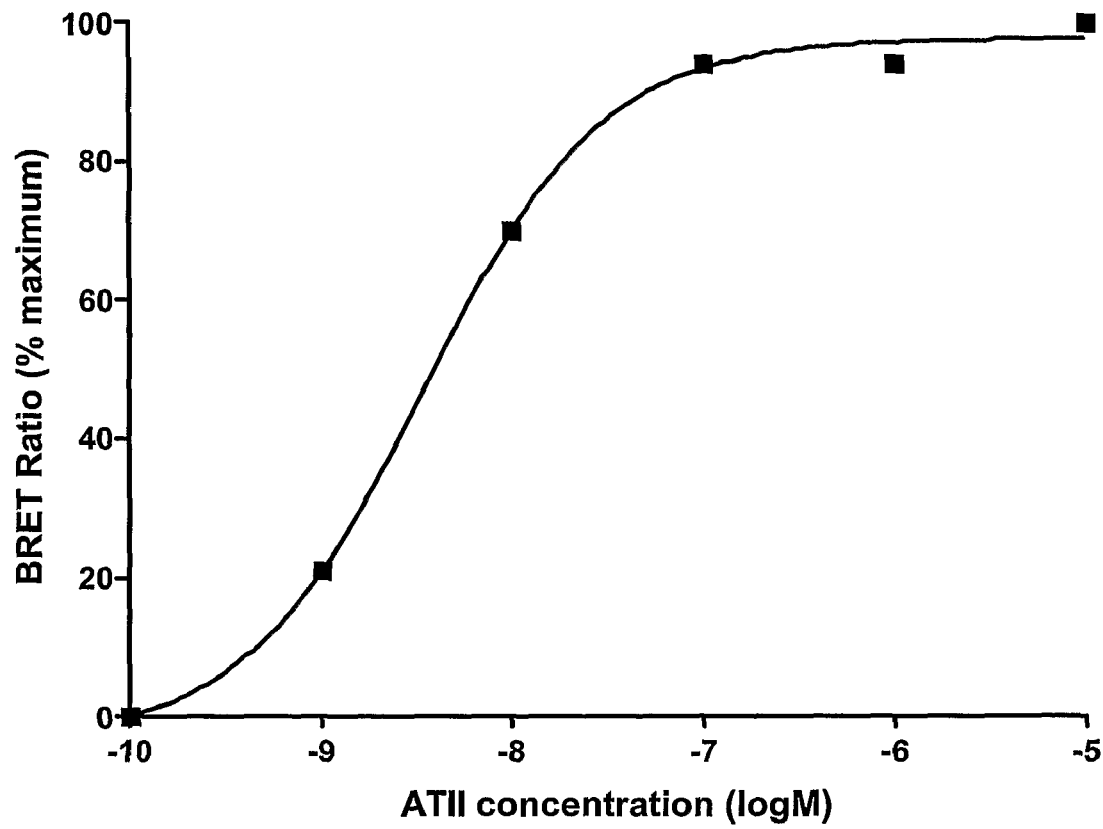

FIG. 25 shows a dose-response curve for the bradykinin B2 receptor (B2R) as IG1, Rluc8 as RC1, beta-arrestin 2 (barr2) as IG2, Venus as RC2 and hemagglutin epitope-tagged angiotensin 11 receptor type 1 (HA-AT1R) as IG3. BRET measurements at 37C were carried out on HEK293 cells transiently co-expressing B2R/Rluc8, barr2/Venus and HA-AT1R treated with increasing doses of Angiotensin II (AngII). A sigmoidal dose response curve was plotted using Prism (GraphPad) allowing for variable slope.

ABBREVIATIONS

ACE angiotensin-converting enzyme.
a-MSH alpha-melanocyte-stimulating hormone.
AngII angiotensin II.
AT1R angiotensin II receptor type 1.
B2R bradykinin B2 receptor.
barr beta-arrestin.
BK bradykinin.
BRET Bioluminescence resonance energy transfer.
BROM Bromocriptine.
CB Cannabinoid receptor.
CCR CC chemokine receptor.
CCR5(5)TYFP CCR5 linked to TYFP via a 5 amino acid linker region.
CSF Cerebrospinal fluid.
CXCR CXC chemokine receptor.
D2LR Dopamine D2 receptor (long-form).
D2SR Dopamine D2 receptor (short-form).
DOP Delta opioid.
eBRET extended BRET: BRET monitored over extended time periods.
ECFP Enhanced Cyan Fluorescent Protein, which is a variant of the *Aequorea victoria* green fluorescent protein gene (GFP).
EGFP Enhanced Green Fluorescent Protein is a red-shifted variant of wild-type GFP.
EYFP Enhanced Yellow Fluorescent Protein.
FRET Fluorescence resonance energy transfer.
GPCRs G-protein coupled receptors.
HA Hemagglutin epitope-tag.
hES cells human embryonic stem cells.
His(6) Histidine tag consisting of 6 consecutive histidine residues.
IG Interacting group.
IL-8 Interleukin-8.
KOP Kappa opioid.
MCP1 Monocyte chemoattractant protein 1 (CCR2 selective ligand).
MCR Melanocortin receptor.
MIP1b Macrophage inflammatory protein 1b (CCR5 selective ligand).
mRFP1 Monomeric red fluorescent protein.
OR Opioid receptor.
OxA Orexin A.
OxB Orexin B.
OxR Orexin receptor.
PBS Phosphate-buffered saline.
pcDNA3 Eukaryotic expression vector.
RC Reporter component.
REM Rapid eye movement.
RET Resonance energy-transfer.
Rluc *Renilla* luciferase.
Rluc8 An improved *Renilla* luciferase.
SWS Slow wave sleep.
TRH Thyrotropin releasing hormone.
TRHR Thyrotropin releasing hormone receptor.
TYFP Topaz Yellow Fluorescent Protein.
Venus An improved Yellow Fluorescent Protein.
wt Wild type.

BEST MODE(S) FOR CARRYING OUT THE INVENTION

General

Before describing the present invention in detail, it is to be understood that this invention is not limited to particularly exemplified bioluminescent or fluorescent proteins, analytes, or methods disclosed herein. It is also to be understood that the terminology used herein is for the purpose of describing particular embodiments of the invention only, and is not intended to be limiting.

All publications, including patents and patent applications, cited herein, whether supra or infra, are hereby incorporated by reference in their entirety. However, publications mentioned herein are cited for the purpose of describing and disclosing the protocols, reagents and vectors that are reported in the publications and which may be used in connection with the invention. Nothing herein is to be construed as an admission that the invention is not entitled to antedate such disclosure by virtue of prior invention.

Furthermore, the practice of the present invention employs, unless otherwise indicated, conventional molecular biology, chemistry and fluorescence techniques, within the skill of the art. Such techniques are well known to the skilled worker, and are explained fully in the literature. See, e.g., Coligan, Dunn, Ploegh, Speicher and Wingfield "Current protocols in Protein Science" (1999) Volume I and II (John Wiley & Sons Inc.); and Bailey, J. E. and Ollis, D. F., Biochemical Engineering Fundamentals, McGraw-Hill Book Company, NY, 1986; Lakowicz, J. R. Principles of Fluorescence Spectroscopy, New York: Plenum Press (1983) for fluorescence techniques.

As used herein and in the appended claims, the singular forms "a," "an," and "the" include the plural unless the context clearly dictates otherwise. Thus, for example, a reference to "a protein" includes a plurality of such proteins, and a reference to "an analyte" is a reference to one or more analytes, and so forth.

Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

The invention described herein may include one or more ranges of values (e.g. size, concentration etc). A range of values will be understood to include all values within the range, including the values defining the range, and values adjacent to the range that lead to the same or substantially the same outcome as the values immediately adjacent to that value which defines the boundary to the range.

Throughout this specification, unless the context requires otherwise, the word "comprise" or variations, such as "comprises" or "comprising" will be understood to imply the inclusion of a stated integer, or group of integers, but not the exclusion of any other integers or group of integers.

Specific

As is apparent from the preceding summary of the invention, the invention relates to systems, methods and kits for detecting the association of two agents. The term "association", as used herein, refers to a combination of interacting groups associated via any known direct or indirect stabilising atomic or molecular level interaction or any combination thereof, where the interactions include, without limitation, bonding interactions such as covalent bonding, ionic bonding, hydrogen bonding, co-ordinate bonding, or any other molecular bonding interaction, electrostatic interactions, polar or hydrophobic interactions, or any other classical or quantum mechanical stabilising atomic or molecular interaction.

The term "association" also encompasses any interaction or conformational change involving interacting groups that brings the reporter components into sufficient proximity to generate the signal. In a preferred embodiment of the invention, the distance between the RCs is preferably in the range of between 1 and 10 nm. Direct physical contact between either the IG or the RC of the agents is not required and may be mediated by one or more linkage molecule(s).

As is also apparent from the preceding summary of the invention, the association of primary interest is the association of the first and third agents, detected by way of the association of the second and third agents. More specifically, the association of interest is the association of the interacting groups of the first and third agents, detected by way of the association of the interacting groups of the second and third agents, which is itself detected by the signal produced by proximity of the first and second reporter components. The association of the second and third agents is of interest to the extent that it is modulated by the modulator and thus indicative of the potentially constitutive nature of the association of the first and third agents.

The First, Second and Third Agents

The first and second agents each comprise an interacting group (IG), wherein the IG is coupled directly or indirectly to a reporter component (RC). The third agent comprises an IG.

Agents may advantageously be engineered or modified to contain chemical groups, peptide sequences, proteins or nucleic acid molecules that may (i) facilitate their purification and/or (ii) target them to a subcellular compartment of a eukaryotic host cell and/or (iii) enable them to penetrate the cell membrane of a eukaryotic cell when added to the medium surrounding the cell and/or (iv) enable their expression levels to be assessed by the use of antibodies or otherwise.

Interacting Groups

The term "interacting group" or "IG" as used herein refers to a molecule or complex of molecules that interacts directly or indirectly with another IG. Thus, the interacting group or IG of the first, second and third agents may be a compound, a protein, a protein domain, a protein loop, a protein-terminus, a peptide, a hormone, a protein-lipid complex, a lipid, a carbohydrate, a carbohydrate-containing compound, a nucleic acid, an oligonucleotide, a pharmaceutical agent, a pharmaceutical drug target, an antibody, an antigenic substance, a virus, a bacterium, and a cell or any complex thereof.

Further or alternately, each interacting group may be a receptor of any type, an ion channel, an enzyme, a carrier, a transporter, an integral membrane protein, a cytoskeletal protein, an adhesion molecule, a signalling protein, a scaffolding protein, an accessory protein, a trafficking protein, a transcription factor, a nuclear co-factor or a nucleic acid molecule, as defined below.

When any or each of the first, second and third interacting groups is a nucleic acid molecule then any form of nucleic acid molecule may be used. For example, the nucleic acid molecule might include genomic deoxynucleic acid (DNA), recombinant DNA, complimentary DNA (cDNA), peptide nucleic acid (PNA), ribonucleic acid (RNA), RNA including hetero-nuclear RNA (hnRNA), transfer RNA (tRNA), small interfering RNA (siRNA), messenger RNA (mRNA), or ribosomal RNA (rRNA) and hybrid molecules thereof.

Essentially, the interacting group is an entity capable of forming a complex with one or more other entities. For example, an antibody in context with the present invention would be a first IG in that it is capable of forming a complex with an antigen, wherein the antigen would be the second IG (see infra). Another example of an IG of the present invention would be a ligand, which is capable of forming a complex with a receptor. A further example is the interaction of an enzyme with its substrate.

Additionally, the IGs may be part of the same molecule. Accordingly, for example, the third intracellular loop of a G-protein coupled receptor (GPCR) could be a first IG and the C-terminus of the same receptor could be a second IG which would associate when the receptor is activated or inactivated.

Modulator

The modulator modulates the association of the second interacting group with the third interacting group either directly (such as a ligand) or indirectly (such as by changing pH or temperature).

The modulator may modulate the association of the second interacting group with the third interacting group by interacting with one or more of the first, second or third interacting groups. However, in preferred forms of the invention, the modulator may modulate the association of the second interacting group with the third interacting group by interacting with the third interacting group, either alone, or simultaneously with the first interacting group.

In another advantageous form of the invention, more than one modulator is added in combination. This may include adding a modulator that modulates the association of the second interacting group with the third interacting group by interacting with the third interacting group, in combination with a modulator that modulates the association of the second interacting group with the third interacting group by interacting with the first interacting group.

Reporter Components: Coupling to IGs

As is apparent from the summary of the invention, the first and second agents comprise reporter components coupled to interacting groups. The terms "coupled", "coupled directly" and "coupled indirectly" as used herein means that the reporter component is attached to or associated with the IG to form an agent that is capable of being analysed or detected. The preferred method of coupling is determined by the nature of the IGs and RCs.

The first and second reporter components can be any known compound, organic or inorganic, proteinaceous or non-proteinaceous or complex thereof, capable of emitting a detectable signal. In some embodiments, the reporter component is selected from the group consisting of an enzyme, a luminescent molecule or part thereof, a fluorescent molecule or part thereof and a transcription factor or other molecule coupled to the interacting group.

The direct or indirect coupling of the first and second reporter components to the first and second interacting groups, respectively, may be by any known covalent or non-covalent means of coupling two molecules, including chemical cross-linking, chemical modification of proteins, chemical modification of amino acids, chemical modification of nucleic acids, chemical modification of carbohydrates, chemical modification of lipids, chemical modification of any other organic or inorganic molecule, biotin-avidin interactions, antigen-antibody interaction and nucleic acid hybridisation.

In one form of the invention, the first and/or second reporter component is coupled indirectly to the first and/or second interacting group respectively by a linker. In some embodiments, the linker comprises an enzyme cleavage site.

An example of a direct method of coupling a proteinaceous IG and a proteinaceous RC is genetic fusion, wherein the genes encoding the IG and the bioluminescent or fluorescent protein are fused to produce a single polypeptide chain.

Another example of a direct coupling method is conjugation, wherein the coupling of the IG with the fluorophore uses enzymes such as ligases, hydrolases, particularly phosphatases, esterases and glycosidases, or oxidoreductases, particularly peroxidases.

In a particularly preferred embodiment of the invention, the first and/or second interacting group(s) and the first and/or second reporter component(s), respectively, each respectively form part of single polypeptide chains. Additional functionality may form part of the same polypeptide chain. For example, the first and/or second interacting group(s) and the first and/or second reporter component(s) respectively form part of a single polypeptide chain additionally comprising:

(i) a sequence coding for a peptide sequence used for affinity purification of a fusion construct; and/or (ii) a sequence coding for a peptide sequence which directs the fusion construct to a subcellular compartment of a eukaryotic cell; and/or (iii) a sequence coding for a peptide sequence that facilitates the penetration of a eukaryotic cell membrane; and/or (iv) a sequence enabling expression levels to be assessed by the use of antibodies or otherwise;

to produce a fusion protein of the interacting group, the reporter component and said additional peptide.

Suitable Reporter Components

Proximity of the first and second reporter components generates a signal capable of detection by the detector. The first and second RCs constitute a complementary pair, in the sense that the first RC may be interchanged with the second RC (i.e. the first RC coupled to the second IG, and the second RC coupled to the first IG) without appreciably affecting the functioning of the invention.

Thus, reporter components can include enzymes, luminescent or bioluminescent molecules, fluorescent molecules, and transcription factors or other molecules coupled to the interacting group by linkers incorporating enzyme cleavage sites. In short any known molecule, organic or inorganic, proteinaceous or non-proteinaceous or complexes thereof, capable of emitting a detectable signal as a result of their spatial proximity.

In a preferred form of the invention, the third agent does not comprise a reporter component capable of generating a signal that substantially interferes with and/or contributes to the signal generated by the proximity of the first and second reporter components. Thus, in this form, detection of the signal generated by the proximity of the first and second reporter components is facilitated.

Preferably, signal generated by the proximity of the first and second reporter components in the presence of the reporter component initiator is selected from the group consisting of: luminescence, fluorescence and colorimetric change.

In some embodiments, the luminescence is produced by a bioluminescent protein selected from the group consisting of luciferase, galactosidase, lactamase, peroxidase, or any protein capable of luminescence in the presence of a suitable substrate.

Preferable combinations of first and second reporter components include a luminescent reporter component with a fluorescent reporter component, a luminescent reporter component with a non-fluorescent quencher, a fluorescent reporter component with a non-fluorescent quencher, first and second fluorescent reporter components capable of resonance energy transfer.

However, useful combinations of first and second reporter components are by no means limited to such.

Alternate combinations of first and second reporter components that may be utilised by the present invention include those exemplified in U.S. Pat. No. 6,893,827 (Applera Corporation); U.S. Pat. No. 6,800,445 (Applera Corporation); U.S. Pat. No. 7,049,076 (Sentigen Biosciences, Inc., and The Trustees of Columbia University of the City of New York); U.S. Pat. No. 6,110,693 (Duke University); U.S. Pat. No. 5,891,646 (Duke University); and WO/2005/031309 (ODYSSEY THERA INC.).

In some aspects of the present invention, the detection system involves combinations of pairs of RCs, capable of being a donor and/or acceptor molecule. Accordingly, the RCs that can be used according to the present invention can be selected based on the physical properties thereof, as is known in the art of resonance energy transfer (RET), the two being selected so that they together comprise the donor and acceptor molecules of a RET pair. If one of the RCs within a RET pair is a bioluminescent protein, the RET is known as bioluminescence RET (BRET). If both RCs forming a RET pair are fluorophores the resulting RET is known as fluorescence RET (FRET). Examples of known suitable donor and acceptor pairs include:

Renilla luciferase and yellow fluorescent protein;
Renilla luciferase and green fluorescent protein;
Cyan fluorescent protein and yellow fluorescent protein;
fluorescein and tetramethylrhodamine;
5-(2'-aminoethyl)aminonaphthalene-1-sulfonic acid (EDANS) and fluorescein;

See generally R. Haugland, Handbook of Fluorescent Probes and Research Chemicals (Sixth Ed. 1995). One or both of the fluorophores can be a fluorescent protein such as green fluorescent protein, and it is particularly advantageous to employ a fluorescent protein as the fluorophore when the IG is a protein or peptide by preparing a fusion protein of the IG and a fluorescent protein.

The complementary first and second reporter components may be provided in the form of complementary portions of a single protein, such as an enzyme, or a fluorophore, whose function is restored when the complementary portions are brought into proximity. For example, Split-Rluc complementation (Paulmurugan, R. & Gambhir, S. S. Monitoring protein-protein interactions using split synthetic Renilla luciferase protein-fragment-assisted complementation. Anal. Chem. 75, 1584-1589 (2003)) and split GFP complementation (Hu, C. D. & Kerrpola, T. K. Simultaneous visualisation of multiple protein interactions in living cells using multicolour fluorescence complementation analysis Nat. Biotechnol. 21, 539-545 (2003)).

In one embodiment, one of the first and/or second reporter components is a non-fluorescent quencher. The non-fluorescent quencher can be any known non-fluorescent chromophore with the ability to absorb light and to quench fluorescence and/or luminescence. The non-fluorescent quencher can therefore be any known molecule, whether proteinaceous or non-proteinaceous. Preferably, the non-fluorescent quencher is selected from the group consisting of dabcy; non-fluorescent pocilloporins, QSY-7, QSY-9, QSY-21, QSY-35, BHq-1, BHQ-2 and BHQ-3.

The term "luminescent molecule" as used herein refers to any molecule capable of generating luminescence. Bioluminescent proteins include luciferases, which have been found in bacteria, fungi, insects and marine creatures. They catalyse the oxidation of a specific substrate (generally known as luciferins) under light emission (Hastings (1996) Gene 173, 5-11). The most widely known substrate is coelenterazine which occurs in cnidarians, copepods, chaetgnaths, ctenophores, decapod shrimps, mysid shrimps, radiolarians and some fish taxa (Greer & Szalay, (2002), Luminescence, 17, 43-74). Two of the most widely used luciferases are:

(i) Renilla luciferase (from R. reniformis), a 35 kDa protein, which uses coelenterazine as a substrate and emits light at 480 nm (Lorenz et al., (1991), PNAS. USA, 88, 4438-4442); and
(ii) Firefly luciferase (from Photinus pyralis), a 61 kDa protein, which uses luciferin as a substrate and emits light at 560 nm (de Wet et al., (1987), Mol. Cell. Biol., 2987, 725-737).

Mutant forms of Renilla luciferase have been developed to improve performance in assays involving bioluminescence. Humanised codon usage has been used to render the luciferase DNA "less foreign" to mammalian transcriptional machinery and ensure maximal gene expression. Examples of point-mutated codon-humanized Renilla luciferases are Rluc2 (C124A/M185V) and Rluc8 (A55T/C124A/S130A/K136R/A143M/M185V/M253L/S287L), which exhibit significantly improved properties compared to non-mutated luciferases, including increased light output when used with coelenterazine analogues and better stability in serum at 37° C. (Loening et al. (2006) Protein Eng Des Sel 19, 391-400; Loening et al. (2007) Nat Methods 4, 641-643; De et al. (2007) Cancer Res 67, 7175-7183).

Gaussia luciferase (from Gaussia princeps) has also been used in biochemical assays (Verhaegen et al., (2002), Anal. Chem., 74: 4378-4385). Gaussia luciferase is a 20 kDa protein that oxidises coelenterazine in a rapid reaction resulting in a bright light emission at 470 nm.

Desirably, the bioluminescent proteins used with the present invention exhibit an intense and constant light emission as long as the substrate is present.

As the bioluminescent proteins are coupled to IGs, it is preferable to use bioluminescent proteins with a small molecular weight to reduce the possibility of inhibition of the interaction between the IGs due to steric hindrance.

Additionally, the bioluminescent proteins preferably consist of a single polypeptide chain to facilitate an easy production of the first and second agents.

Additionally, the bioluminescent proteins preferably do not form oligomers or aggregates, which could otherwise inhibit the function of the IG coupled thereto.

The bioluminescent proteins Renilla luciferase, Gaussia luciferase and Firefly luciferase meet all or most of these criteria.

Fluorescent RCs

The term "fluorescent molecule" as used herein refers to any molecule capable of fluorescence or phosphorescence, including proteins. There are a number of fluorescent proteins that can be employed in this invention. For example, the most widely used fluorescent protein in molecular and cell biology are the green fluorescent protein (GFP) from the jellyfish Aequorea victoria (Tsien, (1998), Annu. Rev. Biochem., 67, 509-544) and the variants derived from its sequence. 'Enhanced' fluorescent proteins (e.g. EGFP) were developed by point mutations that increase the solubility and fluorescence and accelerate protein folding (Zernicka-Goetz et al., (1997), Development, 124, 1133-1137). A Phe to Leu point mutation at position 64 has increased stability of the protein at 37°C and a Ser to Thr mutation at position 65 resulting in an increased fluorescence (Okabe et al., (1997), FEBS Letters, 407, 313-319; Clontech Palo Alto, Calif.). The EGFP which is commercially available from Clontech incorporates a humanised codon usage rendering it "less foreign" to mammalian transcriptional machinery and ensuring maximal gene expression. Additionally, the spectral properties of the green fluorescent protein can be altered by site-directed mutagenesis of specific amino acids, for example blue (EBFP), cyan (ECFP) and yellow (EYFP) mutants of EGFP have been produced (Zhang et al., (2002), Nat. Rev. Mol. Cell Biol., 3, 906-918). Another important class of fluorescent proteins is the red fluorescent proteins (RFP) from the coral species Discosoma (DsRed) (Matz et al., (1999), Nat. Biotechnol. 17, 969-973) and Heteractis crispa (HcRed) (Gurskaya et al., (2001), FEBS Lett. 507, 16-20).

In some embodiments, fluorescent proteins with a high fluorescence quantum yield are used with the present invention.

In some embodiments, the molecular weight of fluorescent proteins used with the present invention will be small enough to avoid steric hindrance between the IGs.

Preferably, monomeric proteins are used to avoid aggregation and interference with the function of a coupled IG. GFP forms a weak dimer but its tendency to dimerise can be minimised by the mutation of hydrophobic amino acids in the dimerisation interface (Zacharias et al., (2002), *Science,* 296, 913-916). The red fluorescent protein DsRed is an obligate tetrameric protein. Recently, 17 point mutations of the DsRed sequence have been described that render DsRed a dimeric protein (dimer2). The subunits of the dimer can be connected via a peptide linker to form a tethered dimer (t-dimer2(12)) that physically acts as a monomer. Additional 16 point mutations convert the dimer2 into a monomeric variant (mRFP1) (Campbell et al., (2002), *PNAS. USA,* 99, 7877-7882). The red fluorescent protein HcRed is a dimeric protein and is not fluorescent as a monomer. However, the two subunits can be fused by a short peptide linker connecting the C-terminus of the first subunit with the N-terminus of the second. This fusion protein (t-HcRed) acts effectively as a monomeric unit, similar to t-dimer2(12) (Fradkov et al., (2002), *Biochem. J.,* 368, 17-21).

Preferably, fluorescent proteins used with the present invention exhibit short maturation times for the formation of their fluorophores. The fluorophore in these molecules is formed by specific re-arrangements of the polypeptide chain. This process can take from less than 1 h to more than 24 h (Zhang et al., (2002), *Nat. Rev. Mol. Cell. Biol.,* 3, 906-918). As a slow maturation process limits the availability and concentration of functional RC, the use of rapidly maturing proteins is preferred. Rapidly maturing fluorescent proteins are for example the green fluorescent protein EGFP and its colour variants and the red fluorescent proteins t-dimer2 and mRFP1. Slow maturing proteins are for example DsRed and HcRed.

In some embodiments, the fluorescence is produced by a fluorescent protein selected from the group consisting of green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilised EGFP (dEGFP), destabilised ECFP (dECFP), destabilised EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, *Renilla* GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrape1, mRaspberry, mGrape2, mPlum (Shaner et al. (2005) *Nat. Methods,* 2, 905-909) and any other proteins named after fruits generated by Tsien R et al., and any fluorescent molecules expressed in corals or derivatives thereof.

A particularly advantageous fluorescent protein useful as a complementary reporter component to a luciferase is Venus (Nagai, T et al., A variant of yellow fluorescent protein with efficient maturation for cell-biological applications, *Nat.* Biotechnol. (2002) 20, 87-90; and Hamdan, F. et al. (2005) High-Throughput Screening of G Protein-Coupled Receptor Antagonists Using a Bioluminescence Resonance Energy Transfer 1-Based Beta-Arrestin2 Recruitment Assay, *Journal of Biomolecular Screening* 10, 463-475).

The terms "fluorescent moiety" or "fluorescent moieties" are used herein interchangeably and refer to non-proteinaceous molecules that are capable of generating fluorescence. Non-proteinaceous fluorescent molecules are usually small molecules that can be attached to other molecules. Each non-proteinaceous fluorescent molecule has specific spectral characteristics. There are a number of different fluorescent moieties that can be employed in this invention. Non-limiting examples include rhodamine, rhodamine derivatives, dansyl, umbelliferone, fluorescein, fluorescein derivatives, Oregon green, Texas Red, Alexa Fluor dyes and Cy dyes. A very attractive class of fluorescent moiety with regards to this invention are fluorescent nanocrystals (Bruchez et al., (1998), *Science,* 281, 2013-2016). Fluorescent nanocrystals exhibit a strong fluorescence and their fluorescence emission can be adjusted by the crystal size over a wavelength range of more than 1000 nm. The excitation of all nanocrystals occurs at the same wavelength independent of their fluorescence emission. Therefore, various nanocrystals can be excited by the same light source or via RET from the same bioluminescent protein or fluorescent molecule.

Preferably fluorescent moieties with high fluorescence quantum yields are used.

In some embodiments, the fluorescence is produced by a fluorescent moiety selected from the group consisting of Alexa Fluor dyes and derivatives, Bodipy dyes and derivatives, Cy dyes and derivatives, fluorescein and derivatives, dansyl, umbelliferone, fluorescent and luminescent microspheres, fluorescent nanocrystals, Marina Blue, Cascade Blue, Cascade Yellow, Pacific Blue, Oregon Green and derivatives, Tetramethylrhodamine and derivatives, Rhodamine and derivatives, Texas Red and derivatives, rare earth element chelates or any combination or derivative thereof or any other molecule with fluorescent properties.

A new type of fluorescent moiety was reported recently and involves both proteinaceous and non-proteinaceous components (Griffin et al., (1998), *Science,* 281, 269-272; Adams et al., (2002), *J. Am. Chem. Soc.,* 124, 6063-6076). The biarsenical-tetracysteine system fuses a short tetracysteine containing peptide to a target protein. This peptide forms a stable, fluorescent complex with a cell-permeable, non-fluorigenic biarsenical dye. Depending on the molecular structure of the dye, different fluorophores are obtained.

Reporter Component Initiator

In some embodiments, at least one reporter component initiator will be utilised to generate a signal from the reporter component. The term "reporter component initiator" as used herein refers to a molecule, a condition and/or source of energy that enables the combination of the first and second reporter components, if in close proximity, to produce a detectable signal.

In some embodiments, the reporter component initiator acts directly, while in other embodiments the action is indirect.

Preferably, the reporter component initiator is a reagent including any known compound, organic or inorganic, proteinaceous or non-proteinaceous, substrate, ligand, antibody, enzyme, nucleic acid, carbohydrate, lipid, drug compound, agonist, antagonist, inverse agonist or compound or complex thereof or a change of conditions including temperature, ionic strength or pH or an energy source including light. The reporter component initiator may be a reporter gene.

In some embodiments, the reporter component initiator is any molecule that can be used in conjunction with an enzyme, transcription factor, fluorescent or bioluminescent molecule to generate a signal.

Examples of reporter component initiators include substrates for bioluminescent reactions, excitation light for fluorophores, reporter genes to respond to reporter components incorporating transcription factors, buffers, appropriate media, conditions required for the uncaging of caged molecules such as UV radiation or live cells to utilise endogenous enzyme activity, suitable temperature, ionic strength and pH to enable the suitable functioning of proteins including enzymes and fluorophores, and suitable conditions to maintain preparation viability including the use of buffers and/or $CO_2$ perfusion.

In the context of bioluminescence, the reporter component initiator will be a substrate. With respect to bioluminescence, the choice of the substrate can impact on the wavelength, intensity and duration of the light generated by the bioluminescent protein. For *Renilla* luciferase for example, coelenterazine analogues are available that result in light emission between 418 and 512 nm (Inouye et al., (1997), *Biochem. J.*, 233, 349-353). A coelenterazine analogue (400A, 'DeepBlueC') has been described emitting light at 400 nm with *Renilla* luciferase (PCT application WO01/46691).

Desirably, the half-life of the substrate is such as to enable light emission for a sufficient period within which to measure such. Particularly desirable is a substrate that provides a sufficient half-life to enable a steady state to be established prior to the addition of the modulator. EnduRen (see Pfleger et al., Extended bioluminescence resonance energy transfer (eBRET) for monitoring prolonged protein-protein interactions in live cells (2006) *Cellular Signalling*, 18, 1664-1670) has been found to be a highly preferable alternative, particularly from the perspective of high throughput screening.

Recently generated protected derivatives of bisdeoxycoelenterazine (DeepBlueC) may be preferable to DeepBlueC in situations where the spectral properties of this substrate are advantageous but the decay kinetics limit effective use (Levi et al. (2007) *J Am Chem Soc* 129, 11900-11901).

Substrates used with this invention are preferably cell-permeable and are able to pass through the cellular membrane to become available to intracellular molecules. Coelenterazine and most of its derivatives are highly cell permeable (Shimomura et al., (1997), *Biochem. J.*, 326: 297-298), whereas luciferin does not efficiently cross the membrane of mammalian cells. However, a caged luciferin compound has been developed that passes through the cell membrane and is released by cellular enzymes or UV light once inside the cytoplasm (Yang et al., (1993), *Biotechniques*, 15, 848-850.

The term "energy source" as used herein refers to any energy source capable of activating a specific fluorophore. In some embodiments, the energy source is light. Non-limiting examples of light sources include lasers, Hg-lamps or Xe-lamps. The light source further has a means of limiting the emitted light to a specific wavelength or a specific range of wavelengths. This can be, for example, a suitable filter mounted to a filter wheel or a filter slide, a monochromator, a dichroic mirror or lasers that only produce light of a single wavelength.

As discussed above, interacting groups may be coupled to reporter components in the first and second agents either directly or indirectly. Where the reporter components are bioluminescent or fluorescent proteins, the bioluminescent or fluorescent proteins may be coupled (e.g., covalently bonded) to a suitable IG either directly or indirectly (e.g., via a linker group). Means of coupling bioluminescent or fluorescent protein to an agent are well known in the art. An example of a direct method of coupling a proteinaceous IG and a proteinaceous RC is genetic fusion, wherein the genes encoding the IG and the bioluminescent or fluorescent protein are fused to produce a single polypeptide chain.

Another example of a direct coupling method is conjugation, wherein the coupling of the IG with the fluorophore uses enzymes such as ligases, hydrolases, particularly phosphatases, esterases and glycosidases, or oxidoreductases, particularly peroxidases.

Fluorescent moieties and non-proteinaceous, non-fluorescent quenchers have the disadvantage that their attachment to proteinaceous IGs is more difficult and often cannot occur inside live cells, in contrast to proteinaceous fluorescent moieties that can be genetically fused to proteinaceous IGs. An example of direct coupling of non-proteinaceous fluorescent moieties and non-fluorescent quenchers to IGs involves moieties covalently linked to reactive groups, which are able to form a covalent bond with specific chemical groups of the IG. Examples are iodoacetamides and maleimides reacting with SH-groups of cysteine residues, and succinimidyl esters, carboxylic acids and sulfonyl chlorides reacting with $NH^{3+}$-groups of lysine residues (Ishii et al., (1986), *Biophys. J.* 50, 75-89; Staros et al., (1986), *Anal. Biochem.* 156, 220-222; Lefevre et al., (1996), *Bioconjug. Chem.* 7, 482-489).

Another known way to attach a fluorescent moiety to an IG typically involves grafting a fluorescent moiety onto the IG or by incorporating the fluorescent moiety into the IG during its synthesis. It is important that the labelled IG retains the critical properties of the unlabelled IG such as selective binding to a receptor or nucleic acid, activation or inhibition of a particular enzyme, or ability to incorporate into a biological membrane. There are a wide variety of fluorescent moieties available, including for example, dipyrromethenboron difluoride dyes, rhodamine, rhodamine derivatives, Texas Red, dansyl, umbelliferone, etc. For a review of various labelling or signal producing systems that may be used, see U.S. Pat. No. 4,391,904.

One example of an indirect method of coupling a fluorescent moiety to an IG such as a protein or nucleic acid, involves the covalent bonding of the fluorescent moiety to a protein such as avidin, which is capable of binding biotin, wherein the biotin is covalently bound to the IG such that the IG and the fluorescent moiety are coupled indirectly together via the interaction between biotin and avidin.

Another example of an indirect method of coupling the IG and bioluminescent or fluorescent protein is via a linker group. A linker group can function as a spacer to distance the bioluminescent or fluorescent protein from the agent in order to avoid interference with binding capabilities. A linker group can also serve to increase the chemical reactivity of a substituent on an agent, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalogue of the Pierce Chemical Co., Rockford, Ill.), may be employed as the linker group. Coupling may be effected, for example, through amino groups, carboxyl groups, sulfhydryl groups or oxidised carbohydrate residues. There are numerous references describing such methodology, e.g., U.S. Pat. No. 4,671,958.

In some embodiments, a proteinaceous RC or a proteinaceous IG is produced recombinantly by inserting a DNA sequence that encodes a RC or IG into an expression vector by standard molecular biology techniques well known to those skilled in the art. The DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide. The polypeptide of the fused RC and IG is expressed in an appropriate host.

Any of a variety of expression vectors known to those of ordinary skill in the art may be employed to express recombinant polypeptides of this invention.

Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are E. coli, yeast or a mammalian cell line, such as CHO, HEK293 or COS-7 cells.

In another embodiment a proteinaceous IG-RC agent is produced recombinantly as a fusion construct. A DNA sequence encoding a fusion protein of the present invention is constructed using known recombinant DNA techniques to assemble separate DNA sequences encoding the proteinaceous RC polypeptide and the IG polypeptide into an appropriate expression vector. The 3' end of the first DNA sequence is ligated, with or without a peptide linker, to the 5' end of the second DNA sequence so that the reading frames of both sequences are in frame to permit mRNA translation of the two DNA sequences into a single fusion protein that retains the biological activity of both the RC and IG. The orientation of RC and the IG within the fusion construct may be swapped to increase its functionality or expression.

A peptide linker sequence may be employed to separate the bioluminescent protein and IG polypeptide by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the bioluminescent protein or IG; and (3) the lack of hydrophobic or charged residues that might react with the polypeptide functional epitopes or decrease the solubility of the fusion protein. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., (1985), *Gene*, 40, 39-46; Murphy et al., (1986), *PNAS. USA*, 83, 8258-8262; U.S. Pat. Nos. 4,935,233 and 4,751,180. The linker sequence may be from 1 to about 50 amino acids in length. Peptide sequences are not required when the bioluminescent protein or IG have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons that are required to end translation and transcription termination signals are only present 3' to the DNA sequence encoding the second polypeptide.

In some embodiments, the sequence encoding the recombinant polypeptide is further genetically fused to a sequence encoding a peptide that facilitates the purification of the fusion construct via affinity chromatography. Examples include histidine tags, maltose-binding protein tags, cellulose-binding protein tags, intein tags, S-tags and GST tags.

In another embodiment, the sequence encoding the recombinant polypeptide is genetically fused to a sequence encoding a peptide that facilitates the targeting of the fusion construct to a specific subcellular compartment of a eukaryotic host cell or for secretion into the surrounding medium. Examples include nuclear localisation signals, mitochondrial import sequences, KDEL sequences to target the endoplasmic reticulum and export signals.

In yet another embodiment the sequence encoding the recombinant polypeptide is genetically fused to a sequence encoding a peptide that facilitates the penetration of eukaryotic cell membranes and thus the uptake of the fusion construct into the cell (Schwartz et al., (2000), *Curr. Opin. Mol. Ther.*, 2, 162-167). Examples include peptide sequences derived from the HIV Tat protein, Herpes simplex virus VP22 and Kaposi FGF-4.

As an alternative to recombinant methods, polypeptides and oligopeptides can be chemically synthesised. Such methods typically include solid-state approaches, but can also utilise solution based chemistries and combinations or combinations of solid-state and solution approaches. Examples of solid-state methodologies for synthesising proteins are described by Merrifield, (1964), *J. Am. Chem. Soc.*, 85, 2149; and Houghton, (1985), *PNAS. USA.*, 82, 5132.

Once the interacting groups and reporter components have been formed as described above they can be utilised in the methods of the present invention.

In some embodiments, each of the first, second and third agents is proteinaceous, with the first and second agents being coupled by genetic fusion to express IG-RC fusion constructs, together with the IG third agent in a suitable host cell. The activation and detection of the RCs as well as an association of the IGs occurs inside the living host cell, inside cellular organelles, inside its cell membrane or at its surface.

In another embodiment a subset of IG-RC agents is proteinaceous and coupled by genetic fusion to express IG-RC fusion constructs in a suitable host cell. Another subset of IG-RC agents, proteinaceous, non-proteinaceous or combinations thereof, is added to the host cell with the optional ability of penetrating the host cell membrane. The activation and detection of the RCs as well as an association of the IGs occurs inside the living host cell, inside cellular organelles, inside its cell membrane or at its surface.

In yet another embodiment the IG-RC agents, regardless of their nature and of the method of preparations, are provided in solutions that may also contain suitable buffer substances. The IG-RC agents may be part of a cell extract, a cell fraction or a synthesis mixture, or may be at least about 90% pure, more preferably at least about 95% pure and most preferably at least about 99% pure. Purification occurs according to standard procedures of the art, including ammonium sulphate precipitation, affinity columns, ion exchange and/or size exclusion and/or hydrophobic interaction chromatography, HPLC, FPLC, gel electrophoresis, capillary electrophoresis and the like (see, generally, Scopes, (1982), *Protein Purification*, Springer-Overflag, N.Y., Deutsche, Methods in Enzymology Vol. 182: Guide to Protein Purification, Academic Press, Inc. N.Y. (1990)).

Signal

The term "signal" as used herein includes luminescence, fluorescence and calorimetric change measured as a change in absorbance. This may result from the enzymatic activity of reporter components and/or up- or down-regulation of reporter genes that are modulated by transcription factors acting as reporter components. The signal may also be dependent upon energy transfer between reporter components.

In some embodiments, the signal will be "emitted light", wherein the step of detecting the signal will be the detection of photons of specific wavelengths of light by photo detector.

Example photo detectors include photomultiplier tubes or CCD cameras. The detector further comprises a means of restricting the detected light to a specific wavelength or a specific range of wavelengths. This can be for example suitable filters mounted to a filter wheel or a filter slide or a monochromator or a dichroic mirror.

In some embodiments the first RC is activated by excitation light specific for this RC and the light emitted by this RC is absorbed by the second RC. Resultant fluorescence from the second RC is then detected, or if the second RC is a quencher, a reduction in fluorescence from the first RC is then detected.

In some embodiments, the first RC is activated by addition of a substrate specific for this RC and the light emitted by this RC is absorbed by the second RC. Resultant fluorescence from the second RC is then detected, or if the second RC is a quencher, a reduction in luminescence from the first RC is then detected.

It should be apparent that the application of the present invention is not limited to the interaction of receptors modulated by ligands. In one embodiment of the invention, the second interacting group is coupled to the third interacting group by way of an enzyme cleavage site, and the modulator is an enzyme adapted to act on the enzyme cleavage site, such that detection of a reduction in the signal generated by proximity of the first and second reporter components by the detector constitutes detection of the dissociation of the second and third agents and consequently constitutes monitoring the association of the first and third agents.

Examples of Systems Amenable to Analysis by the Present Invention

An example of an application for the invention is the analysis of cytokine receptor signalling. Cytokine receptors form hetero-dimers of membrane-bound subunits when activated by binding of their ligand. One subunit is usually specific for the ligand whereas the other one is responsible for signal transduction and is shared by other ligand-specific subunits. The activated receptors interact with intracellular proteins like signal transducer and activator of transcription (STAT) proteins (Ishihara et al. (2002), *Biochim. Biophys. Acta*, 1592, 281-296). Thus cytokine receptor signalling involves a network of signal transducing molecules and receptor molecules with many overlapping and redundant functions. It is often difficult to attribute a particular effect to the actions of specific molecules or receptors. A first agent may be derived from the signal transduction receptor subunit (RC1-IG1), a second agent from the signal transducing protein (RC2-IG2) forming a suitable RET pair (RC1-IG1:IG2-RC2) and a third agent from a ligand-specific receptor subunit.

When the ligand interacts with the third agent in the form of the ligand-specific receptor subunit, the second interacting group, in the form of the signal transducing protein associates with the third agent. If the signal transduction receptor subunit is associated with the ligand-specific receptor subunit, the first and second reporter components will be proximate and generate a detectable signal.

Another example is the analysis of G-protein coupled receptors (GPCRs) that form homo or hetero-dimers. Recent studies have shown that GPCRs may not only act as monomers but also as homo- and hetero-dimers which causes altered ligand binding, signalling and endocytosis (Rios et al. (2000) Pharmacol. Ther. 92, 71-87). The effect of drugs acting as agonists or antagonists of a specific receptor may therefore depend on the binding partners of this receptor. It may be desirable to limit the effect of a drug to a cellular response mediated by a specific receptor dimer. The system provided by this invention is capable of monitoring the activity of a specific GPCR hetero-dimer.

The GPCRs themselves act as IGs. One GPCR is attached to an RC (IG1-RC1, IG3). A second IG (IG2-RC2) is derived from a molecule that interacts with GPCRs upon ligand binding (e.g. beta-arrestin, or a mutant thereof). The detection system not only detects the formation of the receptor heterodimer but can distinguish whether a ligand or drug acts as an agonist, partial agonist, antagonist, inverse agonist or partial inverse agonist at the receptor hetero-dimer.

Another example is the transcriptional regulation of gene expression. Transcription factors act in multiprotein-DNA complexes and the composition of these complexes determines their specificity and activity (Wolberger et al. (1999) Ann. Rev. Biophys. Biomol. Struct. 28, 29-56). For example the transcription factor Fos is only active as a hetero-dimer with a member of the Jun transcription factor family (Chinenov et al. (2001) Oncogene 20, 2438-2452). The Fos/Jun dimer can activate or repress the transcription of numerous genes. The specificity and activity of the complex is regulated by additional proteins interacting with the dimer, like ETS transcription factors, NF-AT or Smad proteins (Wang et al. (1994) Mol. Cell. Biol. 14, 1153-1159; Stranick et al. (1994) J. Biol. Chem. 272, 16453-16465; Zhang et al. (1998) Nature 394, 909-913). IGs can be derived from Fos and Jun proteins with one being attached to a reporter component. A further IG is derived from a transcriptional regulator interacting with the Fos/Jun complex. This IG is attached to a second RC that emits or quenches light transferred from the RC attached to the Fos or Jun protein. This signal is specific for the activity of the trimeric complex involving a particular combination of Fos/Jun proteins. Activation of Fos/Jun by interaction with other regulators or activation of different Fos/Jun complexes with the same regulator will result in different signals depending on whether they occur due to first and second IG association, or due to first and second RC proximity resulting from second and third IG association, or due to a combination of both.

Another example is the development of novel antiviral drugs. A major problem of therapies for HIV and other viruses is the adaptability of the virus by point mutations of viral proteins to gradually become resistant to all drugs being developed so far. Therapies that target multiple events in the viral life cycle are therefore more successful, and mixtures of different drugs, so-called combination therapies have found wide clinical use. Promising, novel anti-retroviral drugs are virus entry inhibitors (Starr-Spires et al. (2002), *Clin. Lab. Med.* 22, 681-701). The entry of HIV virions is mediated via two cellular receptors: CD4 and CXCR4 or CCR5, depending on the virus strain. Antibodies or drugs only blocking the virus-CD4 interaction rapidly loose their efficiency as the viral surface changes. The system provided by this invention allows the simultaneous detection of the viral binding to both receptors. One of the two receptors can be labelled with an RC, as is the viral surface protein, yielding a specific signal when the trimeric complex is formed. Thus, compounds can be identified that efficiently block both interactions or inhibit required conformational changes of the viral protein to bind to both receptors. As two vital interactions are targeted simultaneously the emergence of resistant viruses is less likely.

In another example, the invention is used to analyse the composition, conformation, assembly or dissociation of a large, stable molecular complex. The presence or absence of a RET signal indicates the assembly and functionality of the complex or of conformational changes/movements within the complex or components of the complex. Examples of complexes include transcription factor complexes, ribosomes, proteasomes, chaperones, oligomeric receptors, ion channels etc.

It is likely that repertoires of hetero-dimers in different tissues are unique and that they represent 'novel' drug targets. For example, 6'guanidinoaltrindole, an analogue of a well-known KOP receptor ligand, has been identified as a DOP-KOP hetero-dimer selective agonist, with efficacy as a spinally selective analgesic, leading to the conclusion that DOP-KOP heterodimers are expressed in the spinal cord, but not in the brain (Waldhoer, M. et al. (2005) A hetero-dimer selective agonist shows in vivo relevance of G-protein coupled receptor dimers. *Proc. Natl. Acad. Sci. USA* 102, 9050-9055). Thus, the present invention enables the identification of novel drug targets.

In many cases unexplained observations in the literature may be unmasked by the hetero-dimer pairs revealed by the present invention. For example, the following variants of the opioid receptor are known: 2 mu OR, 2 delta OR and 3 kappa OR. However, there is only one gene for each. It has been suggested that hetero-dimer formation within and outside the family may explain these results.

Other examples where the pharmacology suggests more targets than genes include the Beta-AR4 receptor, calcitonin-gene related peptide 1 and 2, C5A receptor subtypes, ETB receptor subtypes, galanin receptor subtypes, neuropeptide Y3 subtype and platelet activating factor receptor subtypes. In many cases the additional receptor/s could be explained by the presence of a hetero-dimer pair, the identification of which is enabled by the present invention.

Turning specifically to GPCRs, top selling GPCR-targeted medications include Claritin (Histamine Receptor/Allergy indication); Cozarr, Teveten (Angiotensin Receptor/Hypertension indication) and Clozapine (Dopamine/Schizophrenia)—and others highlighted in the following table (GPCR Drugs).

| Trade Name | Entity | Indication | Receptor Target |
| --- | --- | --- | --- |
| Coreg | Carvedilol | Congestive heart failure | Alpha-1A Adrenergic Receptor/Beta 1 adrenergic receptor |
| Toprol-XL | Metoprolol succinate | Hypertension and angina | Beta-1 adrenergic receptor |
| Zoladex | Goserelin acetate | Breast cancer | Luteinizing Hormone Releasing Hormone (LHRH) Receptor |
| Cozaar | Losartan potassium | High blood pressure | Type-1 angiotensin II Receptor (AT1) |
| Claritin Clarinex | Loratadine | Allergic rhinitis | Histamine H1 Receptor |
| Buspar | Buspirone | Anxiety | 5-HT-1A Receptor/D(2) Dopamine Receptor |
| Clozaril | Clozapine | Schizophrenia | D(4) Dopamine Receptor/ Histamine H1 Receptor/D(2) Dopamine Receptor/D1 dopamine receptor-interacting protein calcyon/ Histamine H4 Receptor/ 5-HT-2A Receptor |
| Allegra Telfast | Fexofenidine | Allergic rhinitis | Histamine H1 Receptor |
| Seroquel | Quetiapine | Bipolar disease | 5-hydroxytryptamine 2A receptor/5-hydroxy-tryptamine 2C receptor/ D(2) dopamine receptor/5-hydroxytryptamine 2B receptor |
| Zyprexa | Olanzapine | Schizophrenia & Bipolar disease | Muscarinic acetylcholine receptor M5/D(1A) dopamine receptor/ Muscarinic acetylcholine receptor M1/Muscarinic acetylcholine receptor M3/ 5-HT-2A Receptor/D(4) dopamine receptor/ Histamine H1 receptor/ Muscarinic acetylcholine receptor M4/Muscarinic acetylcholine receptor M2/ D(2) Dopamine Receptor/5-hydroxytryptamine 2C receptor/ |
| Risperdal | Risperidone | Schizophrenia | Histamine H1 receptor/D(2) Dopamine Receptor/Alpha-1A adrenergic receptor/ Beta-1 adrenergic receptor/ 5-HT-2A Receptor |
| Zyrtec | Cetirizine | Allergic rhinitis | Histamine H1 Receptor |
| Singulair | Montelukast | Asthma & Allergies | Cysteinyl leukotriene Receptor 1 |
| Diovan | Valsartan | Hypertension | Type-1 angiotensin II Receptor (AT1) |
| Duragesic | Fentanyl | Pain | Opioid mu Receptor (OP3) |
| Blopress | Candesartan | Hypertension | Type-1 angiotensin II Receptor (AT1) |

| Trade Name | Entity | Indication | Receptor Target |
|---|---|---|---|
| Zantac | Ranitidine | Ulcers | Histamine H2 receptor |
| Tagamet | Cimetidine | Ulcers | Histamine H2 Receptor |
| Teveten | Eprosartan | Hypertension | Type-1 angiotensin II Receptor (AT1) |
| Neurontin | Gabapentin | Seizures | [Voltage-gated sodium channel]/Adenosine A1 receptor/[NMDA receptor]/alpha2-adrenergic receptor |
| Plavix | Clopidogrel | Thrombotic events | P2Y12 platelet ADP Receptor |

Many of these drugs interact with multiple GPCRs, with some of the effects likely to include hetero-dimer targets. The present invention allows a systematic approach to confirm effects elicited through hetero-dimers and allows deduction of explanation for actions, and/or side effects, which in turn allow development of strategies to optimise a pharmaceutical compounds' therapeutic benefit.

As is the case with 6'guanidinoaltrindole, known ligands may exhibit differing abilities to trigger a hetero-dimeric receptor, which may uncover new applications for pre-existing molecules:

Hilairet et al. 2003 (*J. Biol. Chem.* 278, 23731-23737) have recently shown that CB1 antagonists suppress appetite by acting through a CB1/OxR1 hetero-dimer pair.

It has been shown that somatostatin SSTR5 receptor will hetero-dimerise with a dopamine D2 receptor (Rocheville et al. (2000) *Science* 288, 154-157).

An angiotensin AT1 receptor (AT1R)/bradykinin B2 receptor (B2R) hetero-dimer is believed to be responsible for pre-eclampsia in pregnant women. Evidence suggests that the hetero-dimer is more sensitive to Angiotensin II (AngII; AbdAlla et al. (2001) *Nat. Med.* 7, 1003-1009). Angiotensin II and bradykinin (BK) play counter-regulatory roles, with AngII acting as the primary vasoconstrictor in the cardiovascular system and BK antagonising these effects by eliciting vasodilation. Using transiently transfected HEK293 cells it was shown that heterodimerisation of B2R and AT1R occurred and was dependent on the relative amount of receptors present (AbdAlla et al. (2000) *Nature* 407, 94-98). In addition, the degree of Gi- and Gq-mediated signalling was augmented and internalisation profiles of the receptors were altered in conditions where the receptors were coupled. The enhanced signalling efficacy was attributed to increased activation of AT1R, as it predominantly couples to Gi and Gq proteins. Sensitisation of AT1R when associated with B2R led the authors to carry out a successive study to investigate the potential effects this may have in vivo. As previous data had suggested that increased expression of AT1R was not correlated with preeclampsia (Masse et al. (1998) *Clin Biochem* 31, 251-255; Pouliot et al. (1998) *Obstet Gynecol* 91, 591-595) and that circulating levels of angiotensin II were not significantly different compared to control subjects (de Jong et al. (1991) *Clin Perinatol* 8, 683-711), Abdalla et al. (2001, *Nat. Med.* 7, 1003-1009) hypothesised that hypersensitivity to AngII seen in preeclamptic women (Abdul-Karim & Assalin (1961) *Am J Obstet Gynecol* 13, 421-424; Oney & Kaulhausen (1982) *Am J Obstet Gynecol* 142, 17-20) may somehow be related to heterodimerisation between AT1R and B2R. Indeed, the study was able to illustrate that hypersensitive preeclamptic symptoms were strongly correlated with an increased level of B2R expression on platelets, which in turn resulted in increased heterodimerisation with AT1R and elevated sensitivity to circulating levels of AngII (AbdAlla et al. (2001) *Nat. Med.* 7, 1003-1009). Furthermore, they were able to show that heterodimerisation rendered AT1R resistant to free-radical inactivation that exacerbated AngII sensitivity, establishing the first disease model associated with irregular GPCR heterodimerisation (for recent reviews see Quitterer et al. (2004) *Semin Nephrol* 24, 115-119; Shah (2005) *Am J Physiol Renal Physiol* 288, F614-625).

Data supporting the co-expression of AT1R and B2R in the same tissue type is not limited to work by Abdalla and colleagues. Human embryonic stem cells (hES) were treated with specific growth factors in order to commit these cells to an epithelial lineage, then subsequently assessed for expression of GPCRs by RT-PCR (Huang et al. (2007) *J Cell Physiol* 211, 816-825). Intriguingly, differentiated hES and undifferentiated hES (transfected with AT1R and B2R by lentivirus) both expressed these GPCRs, however only the differentiated cells were capable of activating G-protein-mediated signalling pathways in the face of agonist challenge.

A study attempted to determine the mechanisms contributing to the ability of angiotensin-converting enzyme (ACE) inhibitors to enhance liver regeneration in rats following partial hepatectomy (Yayama et al. (2007) *Biol Pharm Bull* 30, 591-594). ACE catalyses the formation of AngII, thus inhibition of this enzyme effectively blocks the synthesis of AT1R agonist. Liver regeneration was significantly greater in animals treated with an ACE inhibitor compared to controls, and in combination with AT1R antagonists further improved the extent of liver regeneration. This effect was partially inhibited by a B2R-specific antagonist, indicating B2R activation and AT1R inhibition by ACE inhibitors may underlie the regenerative properties of such compounds.

One peculiarity of the opioid system is the inability of the receptors to recycle and this results in desensitisation of the opioid effect. This is due to the receptors failing to internalise upon ligand stimulation. The present invention may enable the identification of a receptor that will hetero-dimerize with an opioid receptor, in which case it would be possible that co-administration of a ligand for this partner receptor could trigger internalisation of the receptor hetero-dimer, and thereby avoid opioid receptor de-sensitisation.

Orphan receptors have unknown functions and no information available about their respective ligands. Many GPCRs are orphan receptors. The present invention may be utilised to test whether any orphan receptors can form hetero-dimer pairs with a panel of potential suitor receptors, including GPCRs. The ability to trigger the orphan receptor with known agonist and antagonists can then be tested by co-expression studies. A recent example of this is with the MrgE orphan receptor, which was found to hetero-dimerise with the MrgD receptor and to enhance the potency of the MrgD agonist B-alanine. These receptors are potentially involved in pain control.

Generally, for high-throughput screening and drug discovery, this type of assay can be used to find compounds inhibiting or activating the function of a molecule in its environment within a specific multi-component molecular associate. The function of the same molecule within another associate may not be affected.

It will be clear to those skilled in the art that the aspects of molecular interaction as described above play an important role in numerous cellular functions and are not limited to those described in the examples.

Thyrotropin Releasing Hormone Receptor/Orexin Receptor Hetero-Dimer/-Oligomer

As will be apparent from the following examples, the inventors herein have applied the system of the invention to identify and characterize the molecular association of the thyrotropin releasing hormone receptor with the orexin receptor.

The phrase "thyrotropin releasing hormone receptor" or "TRHR" is to be understood to at least include the G protein-coupled receptor analogous to that activated by the thyrotropin releasing hormone (TRH) in the thyrotrope cells of the anterior pituitary gland, as well as a number of structures in the central nervous system (Riehl et al. (2000) *Neuropsychopharmacology* 23, 34-45), that has, among other roles, a major regulatory role in stimulating the synthesis and secretion of thyrotropin (thyroid-stimulating hormone; TSH) and is synonymous with thyrotropin releasing hormone receptor 1 (TRHR1) (Gershengorn (2003) Thyrotropin-releasing hormone receptor signaling, in *Encyclopedia of hormones*. Eds Henry H L and Norman A W. Academic Press. Vol 3; 502-510). The phrase "thyrotropin releasing hormone receptor" or "TRHR" is also to be understood to mean thyrotropin releasing hormone receptor 2 or TRHR2, a second subtype of thyrotropin releasing hormone receptor known to be expressed at least in the rat and mouse and whose function is yet to be clearly elucidated (Gershengorn (2003) Thyrotropin-releasing hormone receptor signaling, in *Encyclopedia of hormones*. Eds Henry H L and Norman A W. Academic Press. Vol 3; 502-510). The phrase "thyrotropin releasing hormone receptor" or "TRHR" is to be further understood to include newly discovered TRHR family members. Throughout the examples, thyrotropin releasing hormone receptor and the acronym TRHR refers to TRHR1.

The phrase "orexin receptor" or "OxR" is to be understood to mean either orexin receptor 1 (OxR1; OXR1; $OX_1R$; hypocretin-1-receptor; hcrtr 1) or orexin receptor 2 (OxR2; OXR2; $OX_2R$; hypocretin-2-receptor; hctr 2) being G protein-coupled receptors analogous to those described by Sakurai et al. to be activated by orexin A (OxA; hypocretin-1; Hcrt-1) and orexin B (OxB; hypocretin-2; Hcrt-2) (Sakurai et al. (1998) *Cell* 92, 573-585). "Orexin receptor" or "OxR" is to be further understood to include newly discovered orexin receptor family members.

It will be apparent to a person skilled in the art that association of the thyrotropin releasing hormone receptor with orexin receptor enables the use of ligands of one receptor (be they agonists, inverse agonists or antagonists) in the treatment of ailments related to the other receptor.

Thus, the present invention encompasses a method for the treatment of a patient suffering from an orexin-related ailment by administering a therapeutically effective amount of a thyrotropin-releasing hormone receptor agonist, inverse agonist or antagonist.

The thyrotropin-releasing hormone receptor agonist, inverse agonist or antagonist may be co-administered with an orexin receptor agonist, inverse agonist or antagonist.

The present invention further encompasses a method for the treatment of a patient suffering from a thyrotropin-releasing hormone-related ailment by administering a therapeutically effective amount of an orexin receptor agonist, inverse agonist or antagonist.

The present invention further encompasses a method for the manufacture of a medicament for the treatment of a patient suffering from an orexin-related ailment by administering a therapeutically effective amount of a thyrotropin releasing hormone receptor agonist, inverse agonist or antagonist.

The medicament may further contain an orexin receptor agonist, inverse agonist or antagonist.

The present invention further encompasses a method for the manufacture of a medicament for the treatment of a patient suffering from a thyrotropin-releasing hormone-related ailment by administering a therapeutically effective amount of an orexin receptor agonist, inverse agonist or antagonist.

The medicament may further contain a thyrotropin-releasing hormone receptor agonist, inverse agonist or antagonist.

Thus, the present invention encompasses a method for the treatment of a patient suffering from an orexin-related ailment by administering a therapeutically effective amount of a thyrotropin-selective binding agent, or fragment thereof.

The thyrotropin-selective binding agent may be an antibody, including a humanised antibody, a polyclonal antibody, a monoclonal antibody, a chimeric antibody, a CDR-grafted antibody and/or an anti-idiotypic antibody.

The present invention further encompasses a method for the treatment of a patient suffering from a thyrotropin-releasing hormone-related ailment by administering a therapeutically effective amount of an orexin-selective binding agent, or fragment thereof.

The orexin-selective binding agent may be an antibody, including a humanised antibody, a polyclonal antibody, a monoclonal antibody, a chimeric antibody, a CDR-grafted antibody and/or an anti-idiotypic antibody.

The functions of thyrotropin-releasing hormone (TRH) in the central nervous system (CNS) are reported by Gary (Gary, Keith A., et al., The Thyrotropin-Releasing Hormone (TRH) Hypothesis of Homeostatic Regulation: Implications for TRH-Based Therapeutics, JPET 305:410-416, 2003) as four anatomically distinct components that together comprise a general TRH homeostatic system, being 1) the hypothalamic-hypophysiotropic neuroendocrine system, 2) the brainstem/midbrain/spinal cord system, 3) the limbic/cortical system, and 4) the chronobiological system.

Gary further notes that "an appreciation of the global function of TRH to modulate and normalize CNS activity, along with an appreciation of the inherent limitations of TRH itself as a therapeutic agent, leads to rational expectations of therapeutic benefit from metabolically stable TRH-mimetic drugs in a remarkably broad spectrum of clinical situations, both as monotherapy and as an adjunct to other therapeutic agents".

Thyrotropin releasing hormone-related ailments include aliments that are related to increased or decreased production of thyrotropin releasing hormone, and/or increased or decreased responsiveness of cells to thyrotropin releasing hormone. The following list (Gary, Keith A., et al., The Thyrotropin-Releasing Hormone (TRH) Hypothesis of Homeostatic Regulation: Implications for TRH-Based Therapeutics, JPET 305:410-416, 2003) provides some examples of TRH-related ailments:

Depression, especially accompanied by hypersomnolence;
Chronic fatigue syndromes;

Excessive daytime sleepiness (including narcolepsy), neurasthenia, and lethargy;

Sedation secondary to drugs, chemotherapy, or radiation therapy;

Sedative intoxication/respiratory distress (ER setting);

Recovery from general anesthesia;

Attention deficit/hyperactive disorder;

Disturbances of circadian rhythm (e.g. jet lag);

Bipolar affective disorder as a mood stabilizer*;

Anxiety disorders*;

Alzheimer's disease and other dementias with cognition deficits*;

Seizure disorders*; and

Motor neuron disorders*.

* May be particularly effective as adjunctive therapy

However, it should be understood that the phrase thyrotropin releasing hormone-related ailment is not limited thereto.

Orexin-related ailments include aliments that are related to increased or decreased production of orexin, and/or increased or decreased responsiveness of cells to orexin. A major example of an orexin-related ailment is narcolepsy with cataplexy. This is associated with low or undetectable levels of cerebrospinal fluid (CSF) orexin A levels in about 90% of patients (Baumann and Bassetti (2005) Sleep Medicine Reviews 9, 253-268). Mutations of the orexin receptor 2 gene lead to familial canine narcolepsy and a loss of orexin neurons and low CSF orexin A were observed with sporadic canine narcolepsy. Neurological disorders arising from acute traumatic brain injury, Guillain-Barre syndrome and advanced Parkinson's syndrome may also be linked with low or undetectable levels of CSF orexin A levels in some instances. Sakurai has postulated a role for the orexin system in feeding and energy homeostasis as the activity of orexin neurons is inhibited by glucose and leptin, and stimulated by ghrelin, a stomach-derived peptide which promotes feeding. This may have implications for the treatment of obesity (Sakurai (2005) Sleep Medicine Reviews 9, 231-241).

However, it should be understood that the phrase orexin-related ailment is not limited thereto.

Known orexin receptor modulators include orexin A (OxA; hypocretin-1; Hcrt-1), orexin B (OxB; hypocretin-2; Hcrt-2) and fragments thereof (Lang et al. (2004) J Med Chem 47, 1153-1160).

Known antagonists for both OxR1 and OxR2 include 6,7-dimethoxy-1,2,3,4-tetrahydroisoquinoline analogues (Hirose M et al. (2003) Bioorg. Med. Chem. Lett 13, 4497-4499), Almorexant ((2R)-2-{(1S)-6,7-dimethoxy-1-[2-(4-trifluoromethylphenyl)-ethyl]-3,4-dihydro-1H-isoquinolin-2-yl}-N-methyl-2-phenyl-acetamide; ACT-078573; Actelion Pharmaceuticals Ltd., Allschwil, Switzerland; Brisbare-Roch et al. (2007) Nature Medicine 13, 150-155).

Known OxR1 antagonists include SB-334867-A (1-(2-methylbenzoxazol-6-yl)-3-[1,5]naphthyridin-4-yl urea hydrochloride), SB-674042 (1-(5-(2-fluoro-phenyl)-2-methyl-thiazol-4-yl)-1-((S)-2-(5-phenyl-(1,3,4)oxadiazol-2ylmethyl)-pyrrolidin-1-yl)-methanone), SB-408124 (1-(6,8-difluoro-2-methyl-quinolin-4-yl)-3-(4-dimethylamino-phenyl)-urea) and SB-410220 (1-(5,8-difluoro-quinolin-4-yl)-3-(4-dimethylamino-phenyl)-urea) (Haynes et al., (2000) Regulatory Peptides 96, 45-51; Langmead et al. (2004) British Journal of Pharmacology 141, 340-346).

Known OxR2 antagonists include N-Arylmethyl tert-leucyl 6,7-dimethoxy-1,2,3,4-tetrahydroiso-quinoline analogues and N-acyl 6,7-dimethoxy-1,2,3,4-tetrahydroisoquinoline analogues (Hirose M et al. (2003) Bioorg. Med. Chem. Lett 13, 4497-4499), and substituted 4-phenyl-[1,3] dioxanes, particularly 1-(2,4-dibromo-phenyl)-3-((4S,5S)-2,2-dimethyl-4-phenyl-[1,3]dioxan-5-yl)-urea (McAtee L C et al., (2004) Bioorg. Med. Chem. Lett 14, 4225-4229).

Known modulators of the thyrotropin releasing hormone receptor include thyrotropin releasing hormone (TRH; thyroliberin; TRF; pGlu-His-Pro-$NH_2$), [Glu2]TRH, [Glu2]TRH with the amino-terminal pyroglutamyl residue replaced with a pyridinium moiety (Prokai-Tatrai et al. (2005) Med. Chem. 1, 141-152), methyl-TRH, (3-methyl-His2)TRH, montirelin ((3R,6R)-6-methyl-5-oxo-3-thiomorpholinyl carbonyl-L-histidyl-L-prolinamide tetrahydrate; CG-3703; Grunenthal GmbH, Aachen, Germany), CNK-602A (N-[(6-methyl-5-oxo-3-thiomorpholinyl) carbonyl]-L-histidyl-L-prolinamide; Renming et al. (1992) Eur. J. Pharmacol. 223, 185-192), taltirelin ((−)—N—[(S)-hexahydro-1-methyl-2,6-dioxo-4-pyrimidinylcarbonyl]-L-histidyl-L-prolinamide tetrahydrate; Ceredist; TA-0910; Tanabe Seiyaku Co., Ltd., Osaka, Japan), JTP-2942 ($N^{alpha}$-[(1S,2R)-2-methyl-4-oxo-cyclopentylcarbonyl]-L-histidyl-L-prolinamide monohydrate; Japan Tobacco, Inc., Tokyo, Japan), azetirelin (YM-14673; Yamanouchi Pharmaceutical Co., Ltd, Tokyo, Japan), DN-1417 (Gamma-butyrolactone-gamma-carbonyl-histidyl-prolinamide citrate; Miyamoto M et al. (1981) Life Sci. 28, 861-869), Rx-77368 (pGlu-His-(3,3'-dimethyl)-Pro-$NH_2$; Ferring Pharmaceuticals, Feltham, Middlesex, UK), CG-3509 (Grunenthal GmBH, Stolberg, Germany), MK-771 (1-pyro-2-aminoadipyl-L-histidyl-L-thiazolidine-4-carboxamide; Merck, Rahway, N.J.), posatirelin (RGH 2202; L-6-ketopiperidine-2-carbonyl-L-leucyl-L-proline amide; Gedeon Richter Pharmaceuticals, Budapest, Hungary), Ro 24-9975 (1S,3R,5(2S),5S)-5-[(5-oxo-1-phenylmethyl)-2-pyrrolidinyl]-methyl]-5-[(1H-imidazol-5-yl)methyl]-cyclohexaneacetamide; Hoffman-La Roche, Basel, Switzerland), protirelin (5-oxo-L-prolyl-L-histidyl-L-proline amide; Thyrel® TRH; Ferring Pharmaceuticals, Tarrytown, N.Y.), midazolam, diazepam and chlordiazepoxide (inverse agonists; Jinsi-Parimoo A and Gershengorn M C (1997) Endocrinology 138, 1471-1475).

A strong association between the orexin system and narcolepsy with cataplexy has been established (Sakurai (2005) Sleep Medicine Reviews 9, 231-241). Furthermore, Nishino et al. suggest that TRH analogs may be useful for the treatment of excessive daytime sleepiness in narcolepsy (Nishino et al. (1997) The Journal of Neuroscience 17, 6401-6408). The TRH analogs CG-3703 and TA-0910 significantly reduced slow wave sleep (SWS) and rapid eye movement (REM) sleep in a dose- and time-dependent manner. Furthermore, the TRH analogs completely suppressed cataplexy in most of the animals studied. Serum $T_3$ and $T_4$ did not change significantly "suggesting that the anticataplectic and alerting effects of TRH and analogs of TRH are mediated by neuromodulatory CNS properties and not by indirect effects on the thyroid axis." (Nishino et al. (1997) The journal of neuroscience 17, 6401-6408). These observations were supported by a further study in 2000 (Riehl et al. (2000) Neuropsychopharmacology 23, 34-45). The mode of action of TRH and orexins (and analogs thereof) in the pathophysiology of narcolepsy remains to be elucidated, however, the hetero-dimer/-oligomer interaction identified in this invention contributes to the integration of these receptor systems. Riehl et al. comment, "The mechanism underlying the involvement of the hypocretin system in the pathophysiology of narcolepsy remains unclear. It is interesting to note, however, that hypocretin [orexin]-containing neurons are exclusively localized in the lateral hypothalamus (Sakurai et al. 1998 [Cell, 92, 573-585]; Peyron et al. 1998 [J. Neurosc. 18, 9996-10015]), an area that is rich in TRH neurons (Kreider et al. 1985 [Peptides 6, 997-1000]). In addition, both hypocretin [orexin] and TRH receptors are G-protein coupled receptors for neuropeptides, and that the TRH receptor exhibits the second highest (25%) homology (with the Y2 neuropeptide Y receptor having the highest homology) to the hypocretin [orexin] receptors (Sakurai et al. 1998 *[Cell,* 92, 573-585]), suggesting that TRH may play an important role in the pathophysiology of narcolepsy through an unknown specific interaction with the hypocretin [orexin] system." (Riehl et al. (2000) *Neuropsychopharmacology* 23, 34-45). The authors have identified the likelihood of TRH and orexin system integration without identifying that such integration could occur as a result of the receptor hetero-dimerization/-oligomerization identified in this invention.

In addition to narcolepsy, the TRH and orexin receptor systems may integrate with regard to the control of feeding and metabolic homeostasis. Thyroid hormone secretion is suppressed during starvation, whereas preprohypocretin (the precursor of orexin peptides) mRNA is upregulated in the lateral hypothalamus. Such observations led Kok et al., to investigate the integration of the TRH and orexin systems as, "although the topography of hypocretin-[orexin-] and thyrotrope neural circuits suggests that TRH neuronal activity is governed by hypocretin [orexin] input, the nature of the signal (i.e. excitatory or inhibitory) remains unclear" (Kok et al. (2005) *AJP—Endocrinology and Metabolism* 288, 892-899). This study demonstrated significantly lower average plasma TSH concentrations in orexin-deficient narcoleptic humans compared to controls. It is important to note that, as well as feedforward signalling, complex feedback pathways involving autocrine and paracrine feedback via receptors expressed on or in the locality of hormone-/neurotransmitter-secreting neurons are likely to be common in such systems and may play a physiological or pathophysiological role in system integration where these receptors form hetero-dimers/-oligomers.

The present invention comprises a method for screening a test compound for thyrotropin releasing hormone receptor/orexin receptor hetero-dimer/-oligomer selective activity, the method comprising the steps of:
  a) determining whether, and/or the extent to which, the test compound interacts with the orexin receptor while the orexin receptor is associated with the thyrotropin releasing hormone receptor; and
  b) if the test compound interacts with the orexin receptor while the orexin receptor is associated with the thyrotropin releasing hormone receptor, determining whether, or the extent to which the test compound interacts with the orexin receptor in the absence of the thyrotropin releasing hormone receptor;
such that a test compound that exhibits greater affinity and/or potency and/or efficacy when interacting with the orexin receptor while the orexin receptor is associated with the thyrotropin releasing hormone receptor is selective for the thyrotropin releasing hormone receptor/orexin receptor hetero-dimer/-oligomer.

The present invention comprises a method for screening a test compound for thyrotropin releasing hormone receptor/orexin receptor hetero-dimer/-oligomer selective activity, the method comprising the steps of:
  a) determining whether, and/or the extent to which, the test compound interacts with the thyrotropin releasing hormone receptor while the thyrotropin releasing hormone receptor is associated with the orexin receptor; and
  b) if the test compound interacts with the thyrotropin releasing hormone receptor while the thyrotropin releasing hormone receptor is associated with the orexin receptor, determining whether, or the extent to which the test compound interacts with the thyrotropin releasing hormone receptor in the absence of the orexin receptor;
such that a test compound that exhibits greater affinity and/or potency and/or efficacy when interacting with the thyrotropin releasing hormone receptor while the thyrotropin releasing hormone receptor is associated with the orexin receptor is selective for the thyrotropin releasing hormone receptor/orexin receptor hetero-dimer/-oligomer.

In a preferred embodiment of the invention, the step of determining whether, and/or the extent to which, the test compound interacts with the thyrotropin releasing hormone receptor while the thyrotropin releasing hormone receptor is associated with the orexin receptor; and/or the step of determining whether, and/or the extent to which, the test compound interacts with the orexin receptor while the orexin receptor is associated with the thyrotropin releasing hormone receptor are performed by way of the methods of the present invention.

The present invention further encompasses a method for the treatment of a patient suffering from a thyrotropin-releasing hormone-related ailment or an orexin-related ailment by administering a therapeutically effective amount of a thyrotropin releasing hormone receptor/orexin receptor hetero-dimer/-oligomer selective agonist, inverse agonist or antagonist.

The present invention further encompasses the use of a therapeutically effective amount of a thyrotropin releasing hormone receptor/orexin receptor hetero-dimer/-oligomer selective agonist, inverse agonist or antagonist for the manufacture of a medicament for the treatment of a patient suffering from a thyrotropin-releasing hormone-related ailment or an orexin-related ailment.

The present invention includes selective agonists and/or antagonists and/or inverse agonists of the thyrotropin releasing hormone receptor/orexin receptor hetero-dimer/-oligomer.

As used herein the term "patient" refers to any animal that may be suffering from one or more of orexin- or thyrotropin releasing hormone-related ailments. Most preferably the animal is a mammal. The term will be understood to include for example human, farm animals (i.e., cattle, horses, goats, sheep and pigs), household pets (i.e., cats and dogs) and the like.

The phrase "therapeutically effective amount" as used herein refers to an amount sufficient to modulate a biological activity associated with the interaction of orexin receptor agonist, inverse agonist or antagonist with the orexin receptor or thyrotropin releasing hormone receptor agonist, inverse agonist or antagonist with the thyrotropin-releasing hormone receptor or of orexin receptor/thyrotropin-releasing hormone receptor hetero-dimer/oligomer-specific agonist, inverse agonist or antagonist with an orexin receptor/thyrotropin-releasing hormone receptor hetero-dimer/oligomer. In the context of aspects of the invention where both a thyrotropin-releasing hormone receptor agonist, inverse agonist or antagonist and a orexin receptor agonist, inverse agonist or antagonist are administered in combination, a therapeutically effective amount of a thyrotropin-releasing hormone receptor agonist, inverse agonist or antagonist or a therapeutically effective amount of an orexin receptor agonist, inverse agonist or antagonist in combination may be lower than therapeutically effective amounts of thyrotropin-releasing hormone receptor agonist, inverse agonist or antagonist or orexin receptor agonist, inverse agonist or antagonist when administered alone. That is, the administration of a thyrotropin-releasing hormone receptor agonist, inverse agonist or antagonist and a orexin receptor agonist, inverse agonist or antagonist in combination may generate a therapeutic effect at what would otherwise be sub-therapeutic doses of either.

Medicaments of the invention may be administered by injection, or prepared for oral, pulmonary, nasal or for any other form of administration. Preferably the medicaments are administered, for example, intravenously, subcutaneously, intramuscularly, intraorbitally, ophthalmically, intraventricularly, intracranially, intracapsularly, intraspinally, intracisternally, intraperitoneally, buccal, rectally, vaginally, intranasally or by aerosol administration.

The mode of administration must, however, be at least suitable for the form in which the medicament has been prepared. The mode of administration for the most effective response may need to be determined empirically and the means of administration described below are given as examples, and do not limit the method of delivery of the composition of the present invention in any way. All the above formulations are commonly used in the pharmaceutical industry and are commonly known to suitably qualified practitioners.

In addition to the agonist(s) and/or inverse agonist(s) and/or antagonist(s), the medicaments of the invention may include pharmaceutically acceptable nontoxic excipients and carriers and administered by any parenteral techniques such as subcutaneous, intravenous and intraperitoneal injections. In addition the formulations may optionally contain one or more adjuvants.

The pharmaceutical forms suitable for injectable use include sterile aqueous solutions (where water-soluble) or dispersions and sterile powders for the extemporaneous preparation of sterile injectable solutions or dispersion. Alternatively, the compounds of the invention may be encapsulated in liposomes and delivered in injectable solutions to assist their transport across cell membrane. Alternatively or in addition such preparations may contain constituents of self-assembling pore structures to facilitate transport across the cellular membrane. The carrier may be a solvent or dispersion medium containing, for example, water, ethanol, polyol (for example, glycerol, propylene glycol and liquid polyethylene glycol, and the like), suitable mixtures thereof, and vegetable oils. Proper fluidity may be maintained, for example, by the use of a coating such as lecithin, by the maintenance of the required particle size in the case of dispersion and by the use of surfactants. Prolonged absorption of the injectable compositions can be brought about by the use in the compositions of agents delaying absorption, for example, aluminum monostearate and gelatin.

Sterile injectable solutions may be prepared by incorporating the active compounds in the required amount in an appropriate solvent with various of the other ingredients enumerated above, as required, followed by filtered sterilisation. Generally, dispersions are prepared by incorporating the various sterilised active ingredient into a sterile vehicle that contains the basic dispersion medium and the required other ingredients from those enumerated above. In the case of sterile powders for the preparation of sterile injectable solutions, the preferred methods of preparation are vacuum drying and freeze-drying techniques that yield a powder of the active ingredient plus any additional desired ingredient from previously sterile-filtered solution thereof.

Contemplated for use herein are oral solid dosage forms, which are described generally in Martin, *Remington's Pharmaceutical Sciences*, 18th Ed. (1990 Mack Publishing Co. Easton Pa. 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatised with various polymers (E.g., U.S. Pat. No. 5,013,556). A description of possible solid dosage forms for the therapeutic is given by Marshall, in *Modern Pharmaceutics*, Chapter 10, Banker and Rhodes ed., (1979), herein incorporated by reference. In general, the formulation will include the compounds described as part of the invention (or a chemically modified form thereof), and inert ingredients which allow for protection against the stomach environment, and release of the biologically active material in the intestine.

For the agonists, antagonists and inverse agonists of the invention the location of release may be the stomach, the small intestine (the duodenum, the jejunem, or the ileum), or the large intestine. One skilled in the art has available formulations that will not dissolve in the stomach, yet will release the material in the duodenum or elsewhere in the intestine. Preferably, the release will avoid the deleterious effects of the stomach environment, either by protection of the composition or by release of the compounds beyond the stomach environment, such as in the intestine.

To ensure full gastric resistance, a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings that make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, moulded tablets or tablet triturates, moist massing techniques can be used.

The therapeutic can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Colourants and flavouring agents may all be included. For example, compounds may be formulated (such as by liposome or microsphere encapsulation) and then further contained within an edible product, such as a refrigerated beverage containing colorants and flavouring agents.

One may dilute or increase the volume of the therapeutic with an inert material. These diluents could include carbohydrates, especially mannitol, alpha-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrants include but are not limited to starch including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic compounds together to form a hard tablet and include materials from natural products such as acacia, tragacanth, starch and gelatin. Others include methylcellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent may be included in the formulation of the therapeutic to prevent sticking during the formulation process. Lubricants may be used as a layer between the therapeutic and the die wall, and these can include but are not limited to: stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, and Carbowax 4000 and 6000.

Glidants that might improve the flow properties of the compound during formulation and to aid rearrangement during compression might be added. The glidants may include starch, talc, pyrogenic silica and hydrated silicoaluminate.

To aid dissolution of the therapeutic into the aqueous environment, a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compounds either alone or as a mixture in different ratios.

Additives which potentially enhance uptake of the compounds are for instance the fatty acids oleic acid, linoleic acid and linolenic acid.

Controlled release formulation may be desirable. The compounds could be incorporated into an inert matrix that permits release by either diffusion or leaching mechanisms i.e., gums. Slowly degenerating matrices may also be incorporated into the formulation. Another form of a controlled release of this therapeutic is by a method based on the Oros therapeutic system (Alza Corp.), i.e. the drug is enclosed in a semipermeable membrane which allows water to enter and push drug out through a single small opening due to osmotic effects. Some enteric coatings also have a delayed release effect.

A mix of materials might be used to provide the optimum film coating. Film coating may be carried out in a pan coater or in a fluidized bed or by compression coating.

Also contemplated herein is pulmonary delivery of the compounds. The compounds may be delivered to the lungs of a mammal while inhaling and traverses across the lung epithelial lining to the blood stream.

Contemplated for use in the practice of this invention are a wide range of mechanical devices designed for pulmonary delivery of therapeutic products, including but not limited to nebulizers, metered-dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, North Carolina; and the Spinhaler powder inhaler, manufactured by Fisons Corp., Bedford, Mass.

All such devices require the use of formulations suitable for the dispensing of the compounds. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated.

Formulations suitable for use with a nebulizer, either jet or ultrasonic, will typically comprise the compounds suspended in water. The formulation may also include a buffer and a simple sugar (e.g., for protein stabilization and regulation of osmotic pressure). The nebulizer formulation may also contain a surfactant, to reduce or prevent surface induced aggregation of the compounds caused by atomization of the solution in forming the aerosol.

Formulations for use with a metered-dose inhaler device will generally comprise a finely divided powder containing the compounds suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing the compound and may also include a bulking agent, such as lactose, sorbitol, sucrose, or mannitol in amounts which facilitate dispersal of the powder from the device, e.g., 50 to 90% by weight of the formulation. The compounds (or derivative) should most advantageously be prepared in particulate form with an average particle size of less than 10 microns, most preferably 0.5 to 5 microns, for most effective delivery to the distal lung.

Nasal delivery of the compounds is also contemplated. Nasal delivery allows the passage of the protein to the blood stream directly after administering the therapeutic product to the nose, without the necessity for deposition of the product in the lung. Formulations for nasal delivery include those with dextran or cyclodextran.

It will be appreciated that the medicaments of the invention may be given as a single dose schedule, or preferably, in a multiple dose schedule. A multiple dose schedule is one in which a primary course of delivery may be with 1 to 10 separate doses, followed by other doses given at subsequent time intervals required to maintain or reinforce the treatment. The dosage regimen will also, at least in part, be determined by the need of the individual and the judgement of the practitioner.

The invention will now be further described by way of reference only to the following non-limiting examples. It should be understood, however, that the examples following are illustrative only, and should not be taken in any way as a restriction on the generality of the invention described above. In particular, while the invention is described in detail in relation to the use of specific interacting groups, it will be clearly understood that the findings herein are not limited to these interacting groups.

EXAMPLES

General Methods

Cells were seeded in 6-well plates at a density of approximately 630,000 cells/well (HEK293FT) or approximately 150,000 cells/well (COS-7) and maintained at 37° C., 5% $CO_2$ in Complete Media (DMEM containing 0.3 mg/ml glutamine, 100 IU/ml penicillin and 100 µg/ml streptomycin (Gibco)) supplemented with 10% fetal calf serum (FCS; Gibco). Transient transfections were carried out 24 h after seeding using GeneJuice (Novagen) or Metafectene (Biontex) according to manufacturer instructions. 24 h post-transfection, cells were washed with PBS, detached using 0.05% trypsin/0.53 mM EDTA, resuspended in HEPES-buffered phenol red free Complete Media containing 5% FCS and added to a poly-L-lysine-coated white microplate (Nunc). 48 h post-transfection, eBRET assays were carried out following pre-incubation of cells with EnduRen™ (Promega) at a final concentration of 30-40 µM, at 37° C., 5% $CO_2$ for 2 h. For original BRET studies, the HEPES-buffered phenol red free Complete Media was replaced with PBS and coelenterazine h (Molecular Probes) added to a final concentration of 5 µM immediately prior to commencing the assay. BRET measurements were taken at 37° C. using the Victor Light plate reader with Wallac 1420 software (Perkin-Elmer). Filtered light emissions were sequentially measured for 3-5 s in each of the 'donor wavelength window' (400-475 nm) and 'acceptor wavelength window' (>500 nm for EGFP or 520-540 nm for EYFP, Topaz (TYFP) or Venus). The BRET signal observed between interacting proteins is normalized by subtracting the background BRET ratio. This can be done in one of two ways (see Pfleger et al. (2006) *Cell Signal* 18, 1664-1670; Pfleger et al. (2006) *Nat Protoc* 1, 336-344): 1) the ratio of light emission through the 'acceptor wavelength window' over the 400-475 nm emission for a cell sample containing only the donor construct is subtracted from the same ratio for a sample containing the interacting acceptor and donor fusion proteins; 2) the ratio of light emission through the 'acceptor wavelength window' over the 400-475 nm emission for a cell sample treated with vehicle is subtracted from the same ratio for a second aliquot of the same cell sample treated with ligand. In the following examples, the first calculation will be used, unless the signal is described as the 'ligand-induced BRET ratio'. Alternatively, and particularly when illustrating z-factor data (Zhang et al. (1999) *J Biomol Screen* 4, 67-73), the BRET signal observed between interacting proteins can be shown in conjunction with (as oppose to being subtracted by) the background BRET ratio to evaluate error associated with the BRET signal observed between interacting proteins and the error associated with the background BRET ratio independently. In this case, data are shown as 'fluorescence/luminescence' being the ratio of light emission through the 'acceptor wavelength window' over the 400-475 nm emission for a particular cell sample. Unless otherwise stated, BRET signals were measured in 96-well microplates.

Example 1

Figure 1:
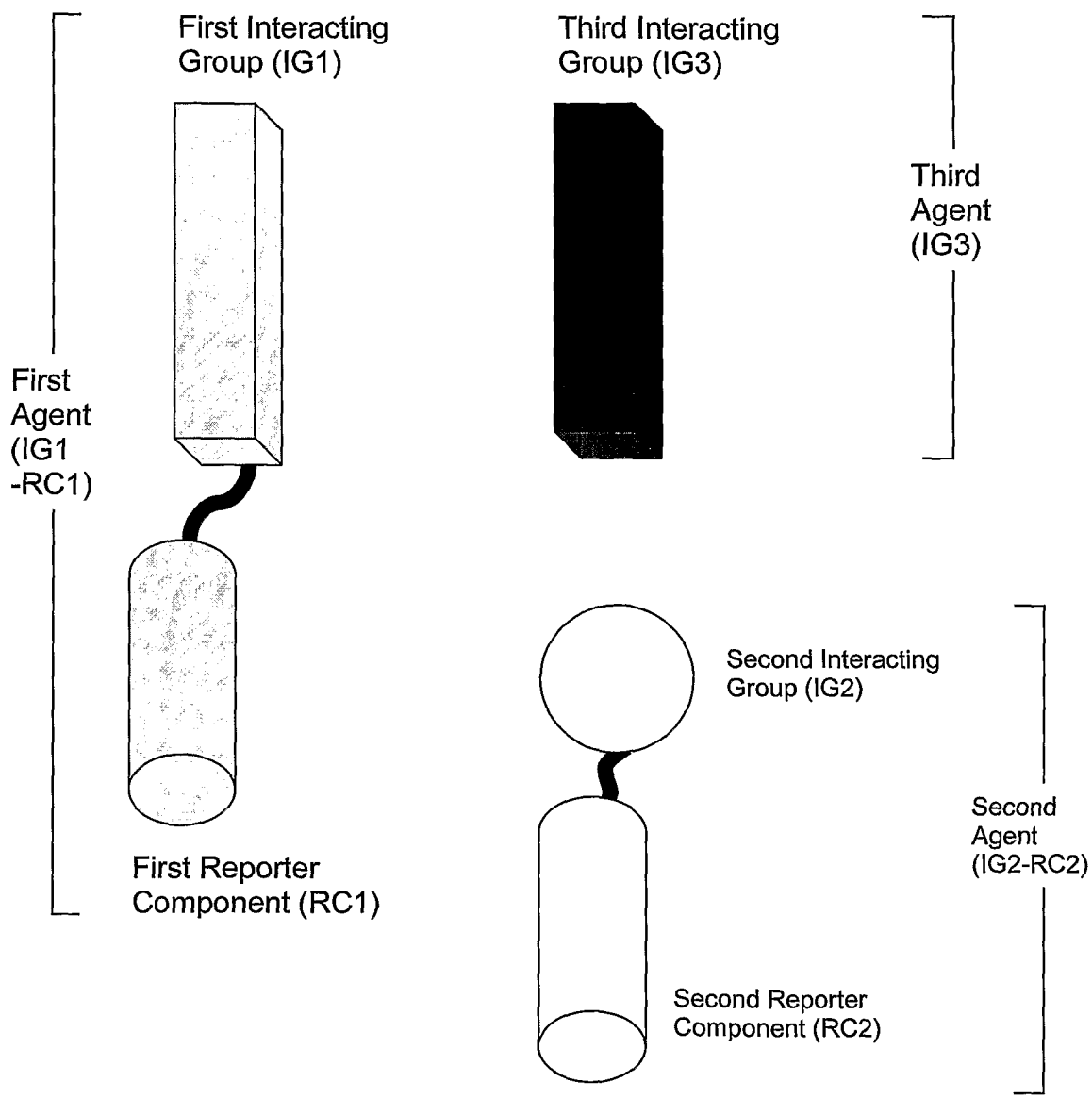
FIG. 1 shows the composition of the agents forming the basis of the system for detecting molecular associations: A first agent comprises a first interacting group coupled to a first reporter component; a second agent comprises a second interacting group coupled to a second reporter component; and a third agent comprises a third interacting group.
Figure 2:
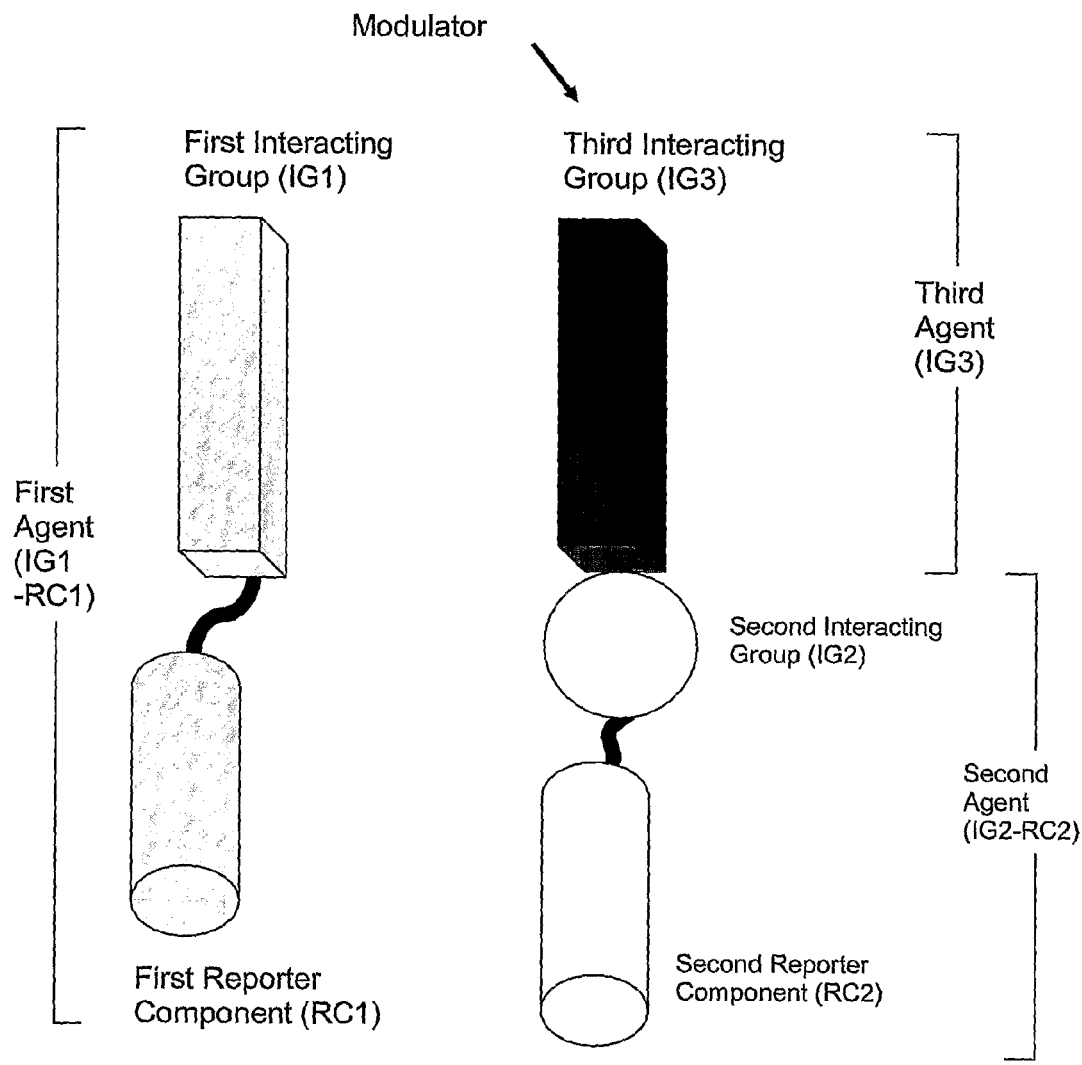
FIG. 2 shows how the administration of the modulator modulates the association of the second interacting group with the third interacting group, preferably by interacting with the third interacting group, either alone, or simultaneously with the first interacting group.
Figure 3:
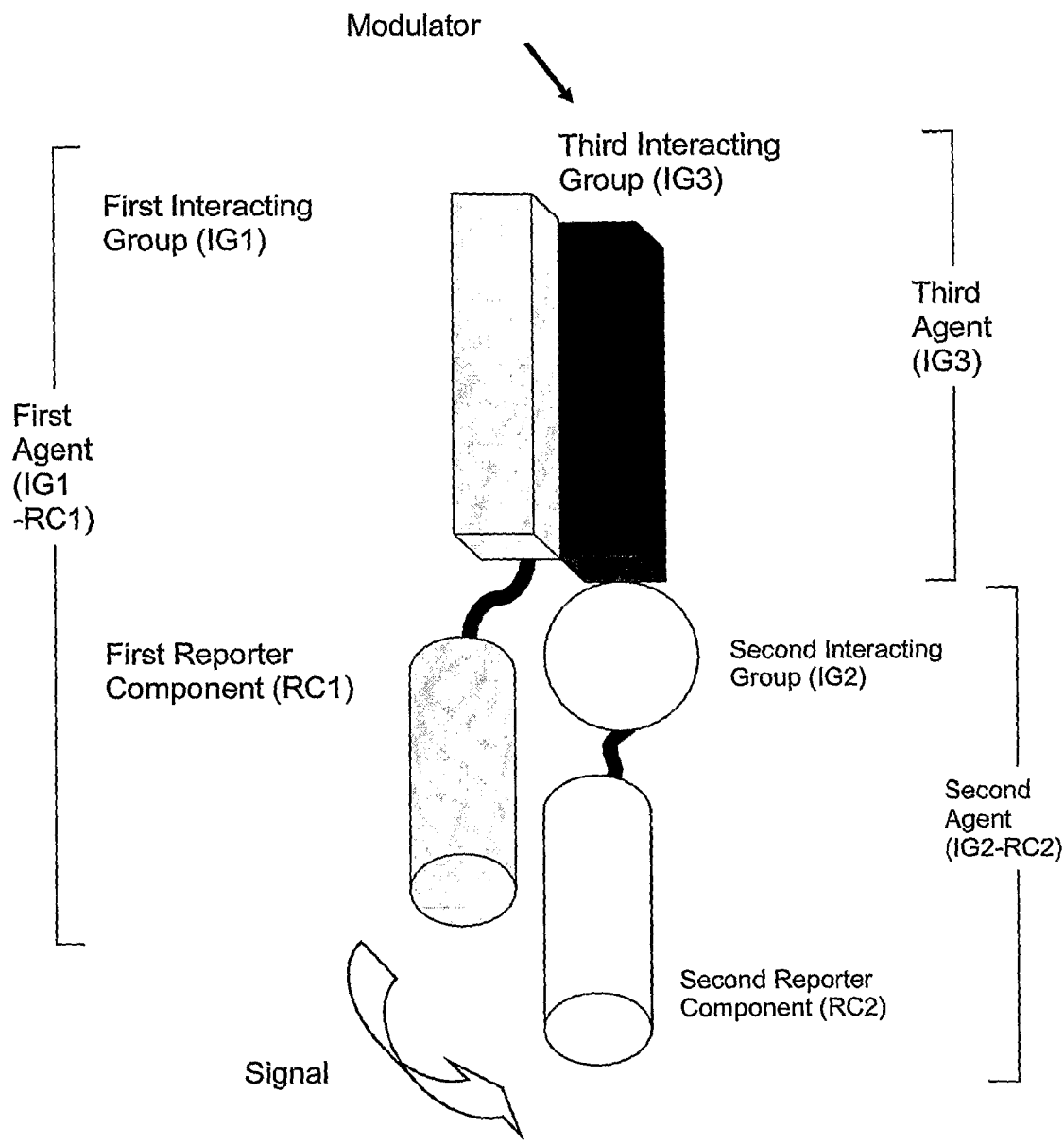
FIG. 3 shows that if the first and third interacting groups are associated, modulation of the association of the second and third interacting groups consequently modulates the proximity of the first and second reporter components thereby modulating the signal that is able to be detected by the detector. Therefore monitoring the signal generated by proximity of the first and second reporter components by the detector constitutes monitoring the association of the first and third agents. If the first and third interacting groups are not associated, the first and second reporter components will remain spatially separated and generation of a detectable signal is unlikely.
Figure 4:
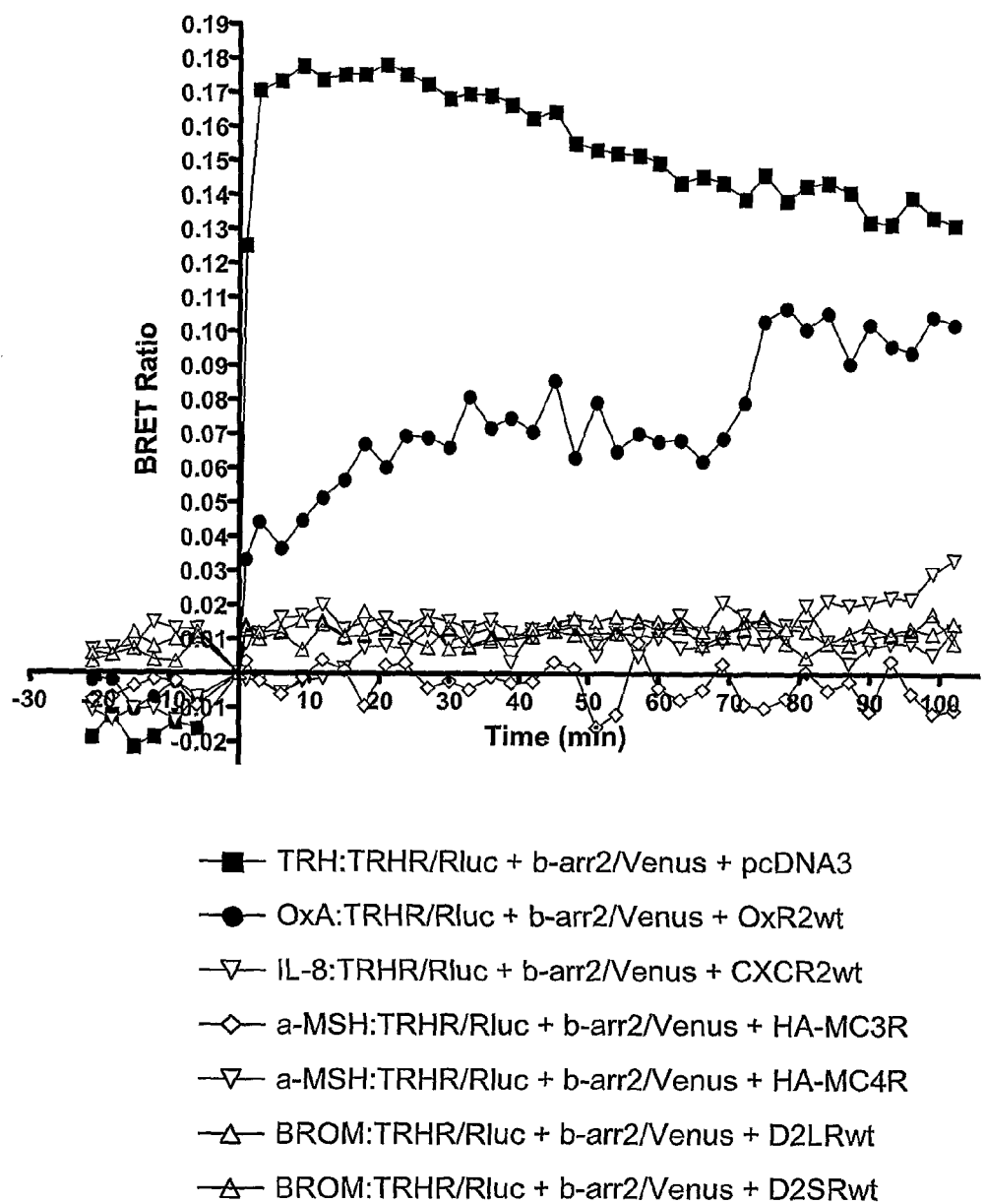
FIG. 4 shows the thyrotropin releasing hormone receptor (TRHR) as IG1, Rluc as RC1, beta-arrestin 2 (barr2) as IG2, Venus as RC2 and a range of different GPCRs as IG3.

Measurement of a Detectable Signal Indicative of the Molecular Association of the Thyrotropin Releasing Hormone Receptor with the Orexin Receptor Referring now to FIG. 4, eBRET signals were measured from cells transiently co-expressing TRHR/Rluc and barr2/Venus with either pcDNA3, OxR2, CXCR2, HA-MC3R, HA-MC4R, D2LR or D2SR following the treatment of each with their respective ligands.

Prior to ligand treatment (added at 0 minutes), a baseline eBRET signal was recorded for each of the receptor combinations. Within the first minute, TRH treatment of cells co-expressing TRHR/Rluc and barr2/Venus with pcDNA3, resulted in the eBRET signal rapidly reaching a peak of greater than 0.17 and this signal remained high for the entire recording period (nearly 2 hours). A signal was also observed following OxA treatment of cells co-expressing TRHR/Rluc, barr2/Venus and OxR2. This signal however took up to 30 minutes to reach approximately 0.07-0.08. No ligand-induced eBRET signals were observed for any of the other receptor combinations.

This example demonstrates that a signal resulting from the proximity of RC1 and RC2 is detected specifically for the combination where the thyrotropin releasing hormone receptor (TRHR) is IG1, Rluc is RC1, beta-arrestin 2 (barr2) is IG2, Venus is RC2 and OxR2 is IG3, and when the modulator, in this case OxA, modulates the association of IG2 and IG3 as a result of interacting specifically with IG3. A signal is not detected when IG3 is CXCR2, HA-MC3R, HA-MC4R, D2LR or D2SR and agonists specific for these IG3s modulate the association of IG2 and IG3, demonstrating the specificity of the signal for the combination with OxR2 as IG3.

More generally, this example demonstrates the ability of the method of the invention to identify and/or monitor specific molecular associations between specific interacting groups, and that the inventors have identified the molecular association of the thyrotropin releasing hormone receptor with the orexin receptor using the method described in this invention.

This example further demonstrates that the kinetic profile observed for the signal resulting from RC1 and RC2 proximity due to modulation of the association of IG2 and IG3 is distinct from the kinetic profile observed for an eBRET signal resulting from RC1 and RC2 proximity due to association of IG1 and IG2 when this IG1-IG2 association is modulated by ligand, in this case TRH, interacting specifically with IG1. The former profile is substantially delayed compared to the latter profile.

Example 2

Measurement of Additive Detectable Signals Indicative of the Molecular Association of the Thyrotropin Releasing Hormone Receptor with the Orexin Receptor Referring now to FIG. 5, eBRET signals were measured from cells transiently co-expressing TRHR/Rluc and EGFP/barr1 or EGFP/barr2 with either pcDNA3 or OXR2. Ligand treatments were either OxA or TRH only or both OxA and TRH combined.

Prior to ligand treatment (added at 0 minutes), baseline eBRET signals were recorded for each of the receptor combinations. PBS treated cells expressing each of the combinations exhibited only baseline eBRET signals for the entire recording period (70 minutes). Following treatment with OxA, cells expressing OxR2 and either EGFP/barr1 (crosses) or EGFP/barr2 (grey inverted triangles) exhibited an eBRET signal reaching a plateau after more than 10 minutes. In cells expressing TRHR/Rluc only (no OxR2) with either of the barrs, TRH treatment resulted in a rapid stimulation of the eBRET signal. The signal with barr2 (black circles) was greater than that for barr1 (grey triangles) however there was no difference for either arrestin if OxA was present (barr2, black triangles; barr1, grey circles). In cells expressing both TRHR/Rluc and OxR2 (barr1, grey squares; barr2, black squares), the addition of both ligands showed an increased eBRET signal over and above that seen following addition of OxA or TRH alone.

This example demonstrates that a signal resulting from the proximity of RC1 and RC2 is detected for the combination where the thyrotropin releasing hormone receptor (TRHR) is IG1, Rluc is RC1, either beta-arrestin 1 (barr1) or beta-arrestin 2 (barr2) is IG2, EGFP is RC2 and OxR2 is IG3 when the modulator, OxA, modulates the association of IG2 and IG3 as a result of interacting specifically with IG3.

Therefore, this example demonstrates signal detection using an alternative combination from that shown in example 1, including use of a different IG2 and RC2.

As in example 1, this example demonstrates the delayed kinetic profile observed for the signal resulting from RC1 and RC2 proximity due to modulation of the association of IG2 and IG3, in this case by OxA, as distinct from the more rapid kinetic profile observed for an eBRET signal resulting from RC1 and RC2 proximity due to association of IG1 and IG2 when this IG1-IG2 association is modulated by ligand, in this case TRH, interacting specifically with IG1. However, in addition to that demonstrated in example 1, this example demonstrates the additive effect of combined treatment with IG1 ligand (TRH) and IG3 ligand (OxA; modulator).

Therefore, this example provides further and distinct demonstration of the ability of the method described in this invention to identify and/or monitor specific molecular associations between specific interacting groups, as well as further and distinct evidence for the molecular association of the thyrotropin releasing hormone receptor with the orexin receptor using the method described in this invention, as this additive effect is indicative of RC1 and RC2 proximity as a result of IG1-IG2 association in addition to IG2-IG3-IG1 association. This provides evidence against signals originating from non-specific IG1-IG2 association in the absence of an IG1-specific ligand. Without wishing to be bound by theory, this additive effect may also be partly due to IG1 ligand acting as a modulator to modulate the association of IG2 and IG3 via allosteric effects on IG3. Furthermore, this additive effect may also be partly due to an active IG conformation (one that is bound to agonist) being more favourable for signal generation, perhaps enabling increased proximity of RC1 and RC2, or more favourable relative orientation of RC1 and RC2.

Example 3

Measurement of the Effect on Signal Generation of an Antagonist that Competes for Modulator Binding Referring now to FIG. 6, eBRET signals were measured from cells transiently co-expressing TRHR/Rluc and barr2/Venus with either pcDNA3, OxR1 or OxR2 following pre-treatment with $10^{-6}$M OxR1-selective antagonist, SB-334867-A, for approximately 40 minutes prior to addition of $10^{-6}$M OxA (IG3 ligand; modulator) or $10^{-6}$M TRH (IG1 ligand), or both. Cells not pretreated with antagonist were pretreated with PBS instead for the same amount of time.

Prior to agonist treatment (added at 0 minutes), baseline eBRET signal was recorded for each of the receptor combinations. A small eBRET signal was observed for OxA-treated TRHR/Rluc and barr2/Venus and OxR1 (grey diamonds). This signal was reduced in the presence of antagonist (open squares). The addition of both TRH and OxA to the OxR1-expressing cells resulted in a much larger signal (white triangles) and the size of this signal was reduced in the presence of the antagonist (grey circles). An eBRET signal was observed following OxA treatment of cells co-expressing TRHR/Rluc, barr2/Venus and OxR2 (black diamonds). This signal was not affected by the pre-treatment of antagonist (white squares). The addition of both TRH and OxA to the OxR2-expressing cells resulted in a signal that did not differ in either the presence (black circles) or the absence (grey triangles) of antagonist.

This example shows a signal resulting from the proximity of RC1 and RC2 detected for the combination where the thyrotropin releasing hormone receptor (TRHR) is IG1, Rluc is RC1, beta-arrestin 2 (barr2) is IG2, Venus is RC2 and OxR1 or OxR2 is IG3 when the modulator, OxA, modulates the association of IG2 and IG3 as a result of interacting specifically with IG3.

This example demonstrates that specific antagonism of modulator binding, in this case the specific antagonism of OxA acting on OxR1 by the OxR1-selective antagonist SB-334867-A, can be detected as a result of its effect on the signal due to the proximity of RC1 and RC2 modulated by the modulator, in this case OxA.

Example 4

Use of a Tag on IG3 that does not Constitute A Reporter Component

Referring now to FIG. 7, eBRET signals were measured from cells transiently co-expressing TRHR/Rluc and EGFP/barr1 or EGFP/barr2 with either pcDNA3 or HA-OxR2. Ligand treatments were either OxA or TRH only.

Prior to ligand treatment (added at 0 minutes), baseline eBRET signals were recorded for each of the receptor combinations. PBS treated cells expressing each of the combinations exhibited only baseline eBRET signals for the entire recording period (80 minutes) (data not shown). Following treatment with OxA, cells expressing HA-OxR2 and either of the EGFP/barrs exhibited an eBRET signal reaching a plateau after more than 10 minutes (EGFP/barr1, black diamonds and EGFP/barr2, black circles). In cells expressing TRHR/Rluc only (no HA-OxR2), TRH stimulated a rapid increase in eBRET signal reaching a peak in the first few minutes, the signal then drifted down slightly over the remainder of the recording period (grey squares). No increase in eBRET signal above baseline was observed following OxA addition to cells lacking HA-OxR2 (grey triangles).

This example shows a signal resulting from the proximity of RC1 and RC2 detected for the combination where the thyrotropin releasing hormone receptor (TRHR) is IG1, Rluc is RC1, beta-arrestin 1 (barr1) or beta-arrestin 2 (barr2) is IG2, EGFP is RC2 and hemagglutin (HA) epitope-tagged OxR2 (HA-OxR2) is IG3 when the modulator, OxA, modulates the association of IG2 and IG3 as a result of interacting specifically with IG3.

This example demonstrates that IG3 can be tagged, such as by the addition of a hemagglutin (HA) epitope-tag, however, this tag does not constitute a reporter component and does not interfere with and/or contribute to the signal generated by the proximity of RC1 and RC2. Such tagging enables additional information to be ascertained, such as the relative expression level of IG3.

Example 5

Use of a Mutant Beta-Arrestin as an Interacting Group

Referring now to FIG. 8, eBRET signals were measured from cells transiently co-expressing TRHR/Rluc and EGFP/barr1 or EGFP/barr1 phosphorylation-independent mutant R169E (EGFP/barr1R169E) with either pcDNA3 or OxR2. Ligand treatments were either OxA or TRH only.

Prior to ligand treatment (added at 0 minutes), baseline eBRET signals were recorded for each of the receptor combinations. PBS treated cells expressing each of the combinations exhibited only baseline eBRET signals for the entire recording period (100 minutes) (white squares, white diamonds and black diamonds). Following treatment with OxA, cells expressing OxR2 and either EGFP/barr1 (black circles) or EGFP/barr1R169E (black triangles) exhibited an eBRET signal with the EGFP/barr1 reaching a plateau after more than 10 minutes while the EGFP/barr1R169E showed a lower signal which reached a plateau by 20 minutes. In cells expressing TRHR/Rluc only (no OxR2) with either of the barrs, TRH stimulated a rapid increase in eBRET signal reaching a peak in the first few minutes, the signal then drifted down slightly over the remainder of the recording period. The signal for the EGFP/barr1R169E (white triangles) was lower than that for EGFP/barr1 (white circles), which may reflect lower expression levels of this protein.

This example shows a signal resulting from the proximity of RC1 and RC2 detected for the combination where the thyrotropin releasing hormone receptor (TRHR) is IG1, Rluc is RC1, barr1 or barr1R169E is IG2, EGFP is RC2 and OxR2 is IG3.

This example demonstrates that a detectable signal can be generated when using a mutant beta-arrestin, such as the beta-arrestin 1 phosphorylation-independent mutant R169E, as one of the interacting groups.

Example 6

Measurement of a Detectable Signal Indicative of the Molecular Association of the C-Terminally Truncated Thyrotropin Releasing Hormone Receptor with the Orexin Receptor Referring now to FIG. 9, eBRET signals were measured from cells transiently co-expressing TRHR335/Rluc and EGFP/barr1 with either OxR2 or TRH. Ligand treatments were either OxA or TRH only.

Prior to ligand treatment (added at 0 minutes), baseline eBRET signals were recorded for each of the receptor combinations. Following treatment with OxA, cells expressing OxR2 (black circles) exhibited an eBRET signal reaching a plateau after about 20 minutes. In contrast, no eBRET signal above baseline was observed from cells expressing TRHR when treated with OxA (white triangles), or from cells expressing OxR2 when treated with TRH (black squares).

This example shows a signal resulting from the proximity of RC1 and RC2 detected for the combination where the thyrotropin releasing hormone receptor truncated at amino acid 335 (TRHR335) is IG1, Rluc is RC1, beta-arrestin 1 (barr1) is IG2, EGFP is RC2 and OxR2 or TRHR is IG3.

This example demonstrates that a detectable signal can be generated when IG1 does not interact with IG2, in this case, a truncated TRHR that does not interact with barr1 (Heding et al. (2000) *Endocrinology* 141, 299-306). The lack of signal observed in FIG. 9 upon treatment of TRHR335/Rluc+EGFP/barr1+OxR2 with TRH confirms that the signal observed upon OxA treatment of this agent combination is not due to IG1-IG2 association.

Therefore, this example provides further and distinct evidence for the molecular association of the thyrotropin releasing hormone receptor with the orexin receptor, as the inability of IG1 to interact with IG2 is indicative of RC1 and RC2 proximity as a result of IG2-IG3-IG1 association and not IG1-IG2 association. This provides further evidence against signals originating from non-specific IG1-IG2 association in the absence of an IG1-specific ligand.

Furthermore, this example demonstrates that the signal results from IG2-IG3-IG1 association as opposed to IG3 activation causing transactivation of IG1, which then associates with IG2, thereby bringing RC1 and RC2 into close proximity without IG2 and IG3 associating.

Example 7

Measurement of a Detectable Signal in a Characteristic Dose-Dependent Manner Indicative of the Molecular Association of TRHR with OXR2

Referring now to FIGS. 10, 11 and 12, BRET signals were measured from cells transiently co-expressing: TRHR/Rluc and barr2/Venus with pcDNA3 (treated with increasing doses of TRH; FIG. 10); OxR2/Rluc and barr2/Venus with pcDNA3 (treated with increasing doses of OxA; FIG. 11); and TRHR/Rluc and barr2/Venus with OxR2 (treated with increasing doses of OxA; FIG. 12).

This example shows: a TRH dose-response curve for TRHR as IG1, Rluc as RC1, barr2 as IG2, Venus as RC2 and in the absence of IG3 (FIG. 10); an OxA dose-response curve for OxR2 as IG1, Rluc as RC1, barr2 as IG2, Venus as RC2 and in the absence of IG3 (FIG. 11); and OxA dose-response curves for the TRHR as IG1, Rluc as RC1, barr2 as IG2, Venus as RC2 and OxR2 as IG3 (FIG. 12).

This example demonstrates that signals can be detected in a dose-dependent manner. Furthermore, the $EC_{50}$ values for signals resulting from the modulator (OxA) acting on IG3 (OxR2) and consequent proximity of IG1-RC1 (TRHR/Rluc) and IG2-RC2 (barr2/Venus; FIG. 12) are comparable to those from OxA activation of IG1 (OxR2) resulting in proximity of IG1-RC1 (OxR2/Rluc) and IG2-RC2 (barr2/Venus; FIG. 11), and distinct from those from TRH activation of IG1 (TRHR) resulting in proximity of IG1-RC1 (TRHR/Rluc) and IG2-RC2 (barr2/Venus; FIG. 10).

Therefore, this example further demonstrates that the signal results from IG2-IG3-IG1 association as opposed to IG1-IG2 association.

The dose-response Hill slopes for OxA activation of IG1 (OxR2) resulting in proximity of IG1-RC1 (OxR2/Rluc) and IG2-RC2 (barr2/Venus; FIG. 11); and TRH activation of IG1 (TRHR) resulting in proximity of IG1-RC1 (TRHR/Rluc) and IG2-RC2 (barr2/Venus; FIG. 10) are both approximately 1. In contrast, the dose-response Hill slopes for modulator (OxA) acting on IG3 (OxR2) resulting in proximity of IG1-RC1 (TRHR/Rluc) and IG2-RC2 (barr2/Venus; FIG. 12) are substantially greater than 1.

Therefore, this example demonstrates the potential for identifying and monitoring specific molecular associations using the Hill slope as an indicator.

This example further demonstrates that different forms of Rluc substrate (reporter component initiator), in this case coelenterazine h and EnduRen, can be used to generate data with similar $EC_{50}$ values (FIG. 12).

Example 8

Measurement of Additive Detectable Signals in a Dose-Dependent Manner Indicative of the Molecular Association of TRHR with OXR2

Referring now to FIGS. 13 and 14, BRET signals were measured from cells transiently co-expressing TRHR/Rluc and EGFP/barr1 in the absence of OxR2 with increasing doses of TRH, as well as cells transiently co-expressing TRHR/Rluc and EGFP/barr1 with OxR2 with increasing doses of OxA with and without $10^{-6}$M TRH, or increasing doses of TRH with $10^{-6}$M OxA.

This example shows a curve mathematically generated by addition of the ligand-induced signal generated with $10^{-6}$M TRH (from the TRH: TRHR/Rluc+EGFP/barr1 curve) to each of the points generated for the OxA: TRHR/Rluc+EGFP/barr1+OxR2 curve (TRHR/Rluc+EGFP/barr1+OxR2: TRH ($10^{-6}$M)+OxA: Data calculated) overlain on a curve generated from data observed for the TRHR/Rluc+EGFP/barr1+OxR2: TRH ($10^{-6}$M)+OxA combination (FIG. 13).

Furthermore, this example shows a curve mathematically generated by addition of the ligand-induced signal generated with $10^{-6}$M OxA (from the OxA: TRHR/Rluc+EGFP/barr1+OxR2 curve) to each of the points generated for the TRH: TRHR/Rluc+EGFP/barr1 curve (TRHR/Rluc+EGFP/barr1+OxR2: TRH+OxA ($10^{-6}$M): Data calculated) overlain on a curve generated from data observed for the TRHR/Rluc+EGFP/barr1+OxR2: TRH+OxA ($10^{-6}$M) combination (FIG. 14).

Therefore, this example clearly demonstrates the additive effect of combined treatment with IG1 ligand (TRH) and IG3 ligand (OxA; modulator) in a dose dependent manner.

Therefore, this example provides further evidence for the molecular association of the thyrotropin releasing hormone receptor with the orexin receptor, as this additive effect is indicative of RC1 and RC2 proximity as a result of IG1-IG2 association in addition to IG2-IG3-IG1 association. This provides further evidence against signals originating from non-specific IG1-IG2 association in the absence of an IG1-specific ligand. Without wishing to be bound by theory, this additive effect may also be partly due to IG1 ligand acting as a modulator to modulate the association of IG2 and IG3 via allosteric effects on IG3. Furthermore, this additive effect may also be partly due to an active IG conformation (one that is bound to agonist) being more favourable for signal generation, perhaps enabling increased proximity of RC1 and RC2, or more favourable relative orientation of RC1 and RC2.

Example 9

Measurement of Additive Detectable Signals in a Dose-Dependent Manner Indicative of the Molecular Association of TRHR335 with OXR2

Referring now to FIG. 15, BRET signals were measured from cells transiently co-expressing TRHR335/Rluc, barr2/Venus and OxR2 with increasing doses of TRH and OxA alone or in combination.

This example demonstrates, using dose response curves, that TRH addition does not result in a BRET signal due to RC1 (Rluc) and RC2 (Venus) proximity as a result of interacting with IG1 (TRHR335) when IG1 (TRHR335) is not able to interact with IG2 (barr2). However, a BRET signal due to RC1 (Rluc) and RC2 (Venus) proximity as a result of interacting with IG3 (OxR2) is observed, indicating an association of IG1 (TRHR335) and IG3 (OxR2). This confirms the data in example 6.

This example further shows that, despite the lack of BRET signal resulting from TRH addition, an increased signal above that observed with OxA addition alone is observed upon addition of both TRH and OxA.

This demonstrates that activation of IG1 (TRHR335) does influence signal generation, despite not being able to contribute to IG1-IG2 (TRHR335-barr2) association. Without wishing to be bound by theory, this may imply that IG1 is influencing IG3 by an allosteric mechanism. This may also imply that an active IG conformation (one that is bound to agonist) is more favourable for signal generation, perhaps enabling increased proximity of RC1 and RC2, or more favourable relative orientation of RC1 and RC2.

Therefore, this example further demonstrates that co-treatment of IG1 and IG3 can result in additional signal generation and/or information compared to treatment of IG3 alone and that such co-treatment is encompassed by the present invention.

Example 10

Measurement of a Detectable Signal Indicative of the Molecular Association of TRHR with OXR2 at Various Expression Levels Referring now to FIG. 16, eBRET signals were measured from cells transiently co-expressing TRHR/Rluc, EGFP/barr1 and OxR2 following addition of $10^{-6}$M OxA.

This example shows cumulative eBRET reads over time for each combination of receptors (IG1 and IG3; data captured over 83 mins). The same amount of EGFP/barr1 (IG2-RC2) is transfected for each experiment. TRHR/Rluc (IG1-RC1) is transfected at a constant amount (0.1 µg DNA/well) while OxR2 (IG3) is transfected at varying amounts of DNA (0, 0.01, 0.05, 0.1, 0.5, 0.7 µg DNA/well). The signal is only detected when OxR2 (IG3) is expressed (no signal was recorded at 0 µg OxR2).

This example demonstrates that signal can be detected when DNA concentrations of OxR2 are as low as 0.01 µg DNA/well.

Furthermore, this example demonstrates that increasing the amounts of OxR2 DNA in each transfection results in increases in the detectable signal. The largest detectable signal is observed at a 1:1 ratio of DNA concentration (0.1:0.1 µg DNA/well). Further increases in the OxR2 DNA concentration (0.5 or 0.7 µg DNA/well) with levels higher than the amount of TRHR/Rluc DNA results in a lower signal being detected.

This example implies that increasing the number of IG3 molecules (OxR2) leads to a point being reached beyond which the number of IG1 molecules (TRHR) becomes limiting for the formation of hetero-dimers/-oligomers. Consequently, there would be increasing propensity for IG3 molecules (OxR2) not associated with IG1 molecules (TRHR) to associate with IG2-RC2 (EGFP/barr1) upon interacting with the modulator (OxA) without a signal being generated. Therefore, signal generation would be inhibited due to the competition for IG2-RC2 (EGFP/barr1) association.

Therefore, this example provides further and distinct evidence for the molecular association of the thyrotropin releasing hormone receptor with the orexin receptor using the method described in this invention, as such decreases in signal with increases in IG3 concentration beyond that of IG1 concentration would not be expected to occur if the signal was not dependent upon specific molecular association of IG1 and IG3.

Example 11

Measurement of a Detectable Signal Indicative of the Molecular Association of TRHR with OXR2 in 384-Well Plates Referring now to FIG. 17, BRET signals were measured from cells transiently co-expressing TRHR/Rluc, barr2/Venus and OxR2 with increasing doses of OxA in 96-well and 384-well microplates.

BRET measurements were carried out using the same concentration of cells expressing the same concentration of agents, the same concentration of Rluc substrate (reporter component initiator) and the same concentration of ligand (modulator). The total volume added to each well of the 384-well plate was approximately half that added to each well of the 96-well plate.

This example demonstrates measurement of a detectable signal indicative of the molecular association of TRHR with OxR2 in a dose-dependent manner in 384-well plates in addition to 96-well plates.

Therefore, this example demonstrates that the method described in the invention is able to be scaled down, thereby making it amenable to high-throughput screening applications.

Example 12

Measurement of a Detectable Signal Indicative of the Molecular Association of the Thyrotropin Releasing Hormone Receptor as IG3 with the Orexin Receptor as IG1

Referring now to FIG. 18, eBRET signals were measured from cells transiently co-expressing OxR2/Rluc8 and barr2/Venus either with HA-TRHR or pcDNA3. Ligand treatments were either OxA or TRH.

Prior to ligand or vehicle treatment (added at 0 minutes), a baseline eBRET signal was recorded for each of the receptor combinations. Within the first 5 minutes, OxA treatment of cells co-expressing OxR2/Rluc8 and barr2/Venus with HA-TRHR, resulted in the eBRET signal rapidly reaching a peak of 0.1 and this signal remained high for the entire recording period (over an hour). A signal was also observed following TRH treatment of cells co-expressing OxR2/Rluc8, barr2/Venus and HA-TRHR. This signal however gradually increased over time to reach 0.05. No ligand-induced eBRET signal was observed following TRH treatment of cells co-expressing OxR2/Rluc8 and barr2/Venus with pcDNA3.

This example demonstrates that a signal resulting from the proximity of RC1 and RC2 is detected specifically for the combination where OxR2 is IG1, Rluc8 is RC1, beta-arrestin 2 (barr2) is IG2, Venus is RC2 and HA-TRHR is IG3, and when the modulator, in this case TRH, modulates the association of IG2 and IG3 as a result of interacting specifically with IG3.

This example demonstrates that the molecular association of the thyrotropin releasing hormone receptor with the orexin receptor is detected with the thyrotropin releasing hormone receptor as IG3 and the orexin receptor as IG1. This demonstrates detection of the molecular association of these receptors using an alternative arrangement of IG's compared to previous examples.

This example also demonstrates the use of a second type of luciferase, Rluc8, which in this case is used as RC1 with Venus as RC2.

This example further demonstrates that the alternative method of calculating the eBRET signal described in Pfleger et al., 2006 (*Cell Signal* 18, 1664-1670) and Pfleger et al., 2006 (*Nat Protoc* 1, 336-344) can be used in the measurement of a detectable signal indicative of the molecular association of the thyrotropin-releasing hormone receptor and the orexin receptor.

As in example 4, this example demonstrates that IG3 can be tagged, such as by the addition of a hemagglutin (HA) epitope-tag, however, this tag does not constitute a reporter component and does not interfere with and/or contribute to the signal generated by the proximity of RC1 and RC2. Such tagging enables additional information to be ascertained, such as the relative expression level of IG3, using the method described in this invention.

Example 13

Measurement of a Detectable Signal Indicative of the Molecular Association of the Thyrotropin Releasing Hormone Receptor with the Orexin Receptor with a Z-Factor in Excess of 0.6

Referring now to FIGS. 19, 20 and 21, eBRET signals were measured from cells transiently co-expressing TRHR/Rluc8 and barr2/Venus with HA-OxR2 aliquoted into all wells of a 96-well plate. Phosphate-buffered saline (PBS) was added to the first two rows and the last two rows of the 96-well plate (48 wells in total) as a vehicle control. OxA was added to the middle four rows of the 96-well plate (48 wells in total). Data are presented as fluorescence/luminescence.

Prior to ligand or vehicle treatment (added at 0 minutes), baseline readings were recorded. OxA treatment of cells co-expressing TRHR/Rluc8 and barr2/Venus with HA-OxR2 resulted in an increase in the fluorescence/luminescence ratio (FIG. 20) that was not observed following treatment with phosphate-buffered saline (PBS) vehicle control (FIG. 19). Analysis of the fluorescence/luminescence ratios comparing 48-wells treated with OxA (defined as 'signal' with respect to z-factor calculation) and 48-wells treated with PBS (defined as 'background' with respect to z-factor calculation) results in a z-factor of 0.67 using the calculation described by Zhang et al., 1999 (*J Biomol Screen* 4, 67-73). Means are shown as solid lines and 3 standard deviations from the mean are shown as dotted lines.

This example demonstrates that a signal resulting from the proximity of RC1 and RC2 is detected specifically for the combination where TRHR is IG1, Rluc8 is RC1, beta-arrestin 2 (barr2) is IG2, Venus is RC2 and HA-OxR2 is IG3, and when the modulator, in this case OxA, modulates the association of IG2 and IG3 as a result of interacting specifically with IG3.

This example demonstrates that the molecular association of the thyrotropin releasing hormone receptor with the orexin receptor is detected in a manner that results in a z-factor in excess of 0.6 and is therefore amenable to high-throughput screening.

This example further demonstrates a third method of representing BRET data that can be used in representing a detectable signal indicative of the molecular association of the thyrotropin-releasing hormone receptor and the orexin receptor.

As in examples 4 and 12, this example demonstrates that IG3 can be tagged, such as by the addition of a hemagglutin (HA) epitope-tag, however, this tag does not constitute a reporter component and does not interfere with and/or contribute to the signal generated by the proximity of RC1 and RC2. Such tagging enables additional information to be ascertained, such as the relative expression level of IG3, using the method described in this invention.

Example 14

Measurement of a Detectable Signal Indicative of the Known Molecular Association of CCR2 and CCR5

Referring now to FIGS. 22 and 23: eBRET signals were measured from cells transiently co-expressing CCR5(5) TYFP and barr2/Rluc either with CCR2 or pcDNA3 (ligand treatments were either MCP1, MIP1b, or both MCP1 and MIP1b combined; FIG. 22); ligand-induced BRET signals were measured from cells transiently co-expressing CCR5(5) TYFP, barr2/Rluc and CCR2 treated with increasing doses of monocyte chemoattractant protein 1 (MCP1; CCR2 selective ligand) and expressed as BRET ratio (% maximum; FIG. 23).

Prior to ligand treatment (added at 0 minutes), baseline eBRET signals were recorded for each of the receptor combinations (FIG. 22). The CCR2 selective ligand, MCP1, elicited no eBRET signal in cells expressing CCR5(5)TYFP with barr2/Rluc and pcDNA3 (open circles), whereas the CCR5 selective ligand MIP1b produced a robust signal (black squares). Addition of MCP1 made no difference to this signal (open squares). MCP1 was able to produce a signal between barr2/Rluc and CCR5(5)TYFP in the presence of CCR2 (black circles). MIP1b treatment of these cells also produced a signal (grey circles). This was lower than the signal produced in the absence of CCR2, which may be due to lower receptor expression levels when co-expressing three proteins and/or may be a consequence of receptor conformational changes upon heterodimerization. Treatment with both ligands in cells expressing both receptors produced the highest eBRET signal (inverted black triangles). PBS treated cells expressing each of the combinations (open triangles and grey squares) exhibited only baseline eBRET signals for the entire recording period (95 minutes).

This example further shows an MCP1 dose-response curve for the CC chemokine receptor 5 (CCR5) as IG1, Topaz (TYFP) as RC1, barr2 as IG2, Rluc as RC2 and CC chemokine receptor 2 (CCR2) as IG3 (FIG. 23).

This example demonstrates that a signal resulting from the proximity of RC1 and RC2 is detected for the combination where CCR5 is IG1, Topaz (TYFP) is RC1, beta-arrestin 2 (barr2) is IG2, Rluc is RC2 and CCR2 is IG3 when the modulator, MCP1 (CCR2 selective ligand), modulates the association of IG2 and IG3 as a result of interacting specifically with IG3.

Therefore, this example demonstrates signal detection using IG1 and IG3 as GPCRs published in the literature as forming a functional hetero-dimer/-oligomer (Mellado et al. (2001) *EMBO Journal* 20, 2497-2507), as distinct from the novel hetero-dimer/-oligomer demonstrated in example 1, thereby providing independent validation of the methods of the invention.

For the barr2/Rluc+CCR(5)TYFP+CCR2 combination, co-treatment with MCP1 and MIP1b resulted in a signal greater than the addition of the signals generated with MCP1 and MIP1b alone (FIG. 22).

Therefore, this example demonstrates that enhanced signals with co-treatment with ligands for both IG1 and IG3 may not be entirely explained by the additive effect of IG1-IG2 association and IG2-IG3-IG1 association. Therefore, without wishing to be bound by theory, this example demonstrates that an IG1 ligand may also act as a modulator to modulate the association of IG2 and IG3 via allosteric effects on IG3. Furthermore, an active IG conformation (one that is bound to agonist) may be more favourable for signal generation, perhaps enabling increased proximity of RC1 and RC2, or more favourable relative orientation of RC1 and RC2.

Therefore, this example demonstrates that co-treatment of IG1 and IG3 can result in additional signal generation and/or information compared to treatment of IG3 alone and that such co-treatment is encompassed by the present invention.

This example also demonstrates the use of a third type of fluorophore, Topaz (TYFP), which in this case is used as RC1 with Rluc as RC2.

Example 15

Measurement of a Detectable Signal Indicative of the Known Molecular Association of B2R and at 1R Referring now to FIGS. 24 and 25: eBRET signals (FIG. 24) and a dose-response curve (FIG. 25) were measured from cells transiently co-expressing B2R/Rluc8, barr2/Venus and HA-AT1R treated with Angiotensin II (AngII).

Prior to ligand treatment (added at 0 minutes), baseline eBRET signals were recorded (FIG. 24). AngII treatment produced a robust increase in the eBRET signal.

This example further shows an AngII dose-response curve for the bradykinin B2 receptor (B2R) as IG1, Rluc8 as RC1, barr2 as IG2, Venus as RC2 and hemagglutin epitope-tagged angiotensin II receptor type 1 (HA-AT1R) as IG3 (FIG. 23).

This example demonstrates that a signal resulting from the proximity of RC1 and RC2 is detected for the combination where B2R is IG1, Rluc8 is RC1, barr2 is IG2, Venus is RC2 and HA-AT1R is IG3 when the modulator, AngII, modulates the association of IG2 and IG3 as a result of interacting specifically with IG3.

Therefore, this example demonstrates signal detection using IG1 and IG3 as a second combination of GPCRs published in the literature as forming a functional hetero-dimer/-oligomer (AbdAlla et al. (2000) *Nature* 407, 94-98; AbdAlla et al. (2001) *Nat. Med.* 7, 1003-1009), as distinct from the novel hetero-dimer/-oligomer demonstrated in example 1, thereby providing further independent validation of the methods of the invention.

The claims defining the invention are as follows:

1. A method for determining whether and/or the extent to which a test compound interacts with a second protein when the second protein is associated with a first protein, the method comprising the steps of:
   a) contacting said test compound with a system comprising:
      i) a first agent, comprising the first protein coupled to a first reporter component;
      ii) a second agent, comprising an interacting group coupled to a second reporter component; and
      iii) a third agent, comprising the second protein;
   wherein proximity of the first and second reporter components generates a signal; and wherein a modulator modulates the association of the interacting group with the second protein; and
   b) determining the signal as a determination of whether and/or the extent to which said test compound interacts with a second protein when the second protein is associated with the first protein.

2. The method according to claim 1 characterised in that the second protein is a receptor, such that the method for determining whether and/or the extent to which a test compound interacts with the second protein when the second protein is associated with the first protein comprises a method for determining whether and/or the extent to which the test compound is an agonist of the second protein when the second protein is associated with the first protein, and the step of determining the signal as a determination of whether and/or the extent to which said test compound interacts with the second protein when the second protein is associated with the first protein more specifically comprises the step of detecting an increase in the signal as a determination of whether the test compound is an agonist of the second protein when the second protein is associated with the first protein.

3. The method according to claim 2 characterised in that the first protein is a receptor.

4. The method according to claim 1 characterised in that the second protein is a receptor, such that the method for determining whether and/or the extent to which a test compound interacts with the second protein when the second protein is associated with the first protein comprises a method for determining whether and/or the extent to which the test compound is an antagonist or partial agonist of the second protein when the second protein is associated with the first protein, the method comprising the steps of:
  a) contacting said test compound with the system comprising:
    i) the first agent, comprising the first protein coupled to the first reporter component;
    ii) the second agent, comprising the interacting group coupled to the second reporter component;
    iii) the third agent, comprising the second protein; and
    iv) an agonist of the second protein;
    wherein proximity of the first and second reporter components generates the signal; and wherein the modulator modulates the association of the interacting group with the second protein; and
  b) detecting a decrease in the signal as a determination of whether and/or the extent to which the test compound is an antagonist or partial agonist of the second protein when the second protein is associated with the first protein.

5. The method according to claim 4 characterised in that the first protein is a receptor.

6. The method according to claim 1 characterised in that the second protein is a constitutively active receptor, such that the method for determining whether and/or the extent to which the test compound interacts with the second protein when the second protein is associated with the first protein comprises a method for determining whether and/or the extent to which the test compound is an inverse agonist of the second protein when the second protein is associated with the first protein, and the step of determining the signal as a determination of whether and/or the extent to which said test compound interacts with the second protein when the second protein is associated with the first protein more specifically comprises the step of detecting a decrease in the signal as a determination of whether and/or the extent to which the test compound is an inverse agonist of the second protein when the second protein is associated with the first protein.

7. The method according to claim 6 characterised in that the first protein is a receptor.

8. The method according to claim 1 characterised in that, the first and second proteins are both receptors, such that the method for determining whether and/or the extent to which the test compound interacts with the second protein when the second protein is associated with the first protein comprises a method for screening the compound for first protein/second protein hetero-dimer/-oligomer selective activity, the method comprising the steps of:
  a) determining whether, and/or the extent to which, the test compound interacts with the second protein while the second protein is associated with the first protein; and
  b) if the test compound interacts with the second protein while the second protein is associated with the first protein, determining whether, and/or the extent to which the test compound interacts with the second protein in the absence of the first protein;
such that the test compound that exhibits greater affinity and/or potency and/or efficacy when interacting with the second protein while the second protein is associated with the first protein is selective for the first protein/second protein hetero-dimer/-oligomer.

9. The method according to claim 1 characterised in that the first and second proteins are both receptors, and the method comprises a method for screening the test compound for first protein/second protein hetero-dimer/-oligomer selective antagonism or partial agonism, the method comprising the steps of:
  a) determining whether, and/or the extent to which, the test compound is an antagonist or partial agonist of the first protein/second protein hetero-dimer/-oligomer, by contacting said test compound with a system comprising:
    i) the first agent, comprising the first protein coupled to the first reporter component;
    ii) the second agent, comprising an interacting group coupled to the second reporter component;
    iii) the third agent, comprising the second protein; and
    iv) an agonist of the first protein, the second protein and/or the first protein/second protein hetero-dimer/-oligomer,
    wherein proximity of the first and second reporter components generates the signal; and wherein the modulator modulates the association of the interacting group with the second protein;
  b) detecting a decrease in the signal as a determination of whether and/or the extent to which the test compound is an antagonist or partial agonist of the first protein/second protein hetero-dimer/-oligomer; and
  c) if the test compound is an antagonist or partial agonist of the first protein/second protein hetero-dimer/-oligomer, determining whether, and/or the extent to which the test compound interacts with the second protein in the absence of the first protein and the first protein in the absence of the second protein; such that the test compound that exhibits greater antagonistic or partial agonistic properties when interacting with the first protein/second protein hetero-dimer/-oligomer is selective for the first protein/second protein hetero-dimer/-oligomer.

10. A method for determining whether and/or the extent to which a test compound interacts with a second protein when the second protein is associated with a first protein, the method characterised in that the first and second proteins are both receptors, and the method comprises a method for screening a test compound for first protein/second protein hetero-dimer/-oligomer selective antagonism or partial agonism, the method comprising the steps of:
  a) determining whether, and/or the extent to which, the test compound is an antagonist or partial agonist of the first protein/second protein hetero-dimer/-oligomer, by contacting said test compound with a system comprising:

i) a first agent, comprising the second protein coupled to a first reporter component;
   ii) a second agent, comprising an interacting group coupled to a second reporter component;
   iii) a third agent, comprising the first protein;
   iv) an agonist of the second protein, the first protein and/or the first protein/second protein hetero-dimer/-oligomer,
   wherein proximity of the first and second reporter components generates a signal, and wherein a modulator modulates association of the interacting group with the first protein;
   b) detecting a decrease in the signal as a determination of whether and/or the extent to which the test compound is an antagonist or partial agonist of the first protein/second protein hetero-dimer/-oligomer; and
   c) if the test compound is an antagonist or partial agonist of the first protein/second protein hetero-dimer/-oligomer, determining whether, and/or the extent to which the test compound is an antagonist or partial agonist of the first protein in the absence of the second protein and the second protein in the absence of the first protein; such that a test compound that exhibits greater antagonistic or partial agonistic properties when interacting with the first protein/second protein hetero-dimer/-oligomer is selective for the first protein/second protein hetero-dimer/-oligomer.

11. The method according to claim 1 characterised in that the first and second proteins are both receptors, and the method comprises a method for screening a test compound for first protein/second protein hetero-dimer/-oligomer selective inverse agonism, the method comprising the steps of:
   a) determining whether, and/or the extent to which, the test compound is an inverse agonist of the first protein/second protein hetero-dimer/-oligomer, by contacting said test compound with a system comprising:
      i) the first agent, comprising the first protein coupled to the first reporter component;
      ii) the second agent, comprising the interacting group coupled to the second reporter component; and
      iii) the third agent, comprising the second protein, wherein the second protein is constitutively active, and
   wherein proximity of the first and second reporter components generates the signal; and wherein the modulator modulates the association of the interacting group with the second protein;
   b) detecting a decrease in the signal as a determination of whether and/or the extent to which the test compound is an inverse agonist of the first protein/second protein hetero-dimer/-oligomer; and
   c) if the test compound is an inverse agonist of the first protein/second protein hetero-dimer/-oligomer, determining whether, and/or the extent to which the test compound is an inverse agonist of the first protein in the absence of the second protein and the second protein in the absence of the first protein; such that a test compound that exhibits greater inverse agonistic properties when interacting with the first protein/second protein hetero-dimer/-oligomer is selective for the first protein/second protein hetero-dimer/-oligomer.

12. A method for determining whether and/or the extent to which a test compound interacts with a second protein when the second protein is associated with a first protein, the method characterised in that the first and second proteins are both receptors, and the method comprises a method for screening a test compound for first protein/second protein hetero-dimer/-oligomer selective inverse agonism, the method comprising the steps of:
   a) determining whether, and/or the extent to which, the test compound is an inverse agonist of the first protein/second protein hetero-dimer/-oligomer, by contacting said test compound with a system comprising:
      i) a first agent, comprising the second protein coupled to a first reporter component;
      ii) a second agent, comprising an interacting group coupled to a second reporter component;
      iii) a third agent, comprising the first protein, wherein the first protein is constitutively active, and wherein proximity of the first and second reporter components generates a signal, and wherein a modulator modulates association of the interacting group with the first protein;
   b) detecting a decrease in the signal as a determination of whether and/or the extent to which the test compound is an inverse agonist of the first protein/second protein hetero-dimer/-oligomer; and
   c) if the test compound is an inverse agonist of the first protein/second protein hetero-dimer/-oligomer, determining whether, and/or the extent to which the test compound is an inverse agonist of the second protein in the absence of the first protein and the first protein in the absence of the second protein; such that the test compound that exhibits greater inverse agonistic properties when interacting with the first protein/second protein hetero-dimer/-oligomer is selective for the first protein/second protein hetero-dimer/-oligomer.

* * * * *